US008796250B2

(12) United States Patent
Wilhelm et al.

(10) Patent No.: US 8,796,250 B2
(45) Date of Patent: Aug. 5, 2014

(54) DIARYL UREAS FOR DISEASES MEDIATED BY PDGFR

(75) Inventors: Scott Wilhelm, Orange, CT (US); Jacques Dumas, Bethany, CT (US); Gaetan Ladouceur, Guilford, CT (US); Mark Lynch, Madison, CT (US); William Scott, Guilford, CT (US)

(73) Assignee: Bayer Healthcare LLC, Whippany, NJ (US)

( * ) Notice: Subject to any disclaimer, the term of this patent is extended or adjusted under 35 U.S.C. 154(b) by 2128 days.

(21) Appl. No.: 10/848,567

(22) Filed: May 19, 2004

(65) Prior Publication Data
US 2005/0059703 A1 Mar. 17, 2005

Related U.S. Application Data

(60) Provisional application No. 60/556,062, filed on Mar. 25, 2004, provisional application No. 60/520,399, filed on Nov. 17, 2003, provisional application No. 60/471,735, filed on May 20, 2003.

(51) Int. Cl.
A01N 43/00 (2006.01)
A61K 31/33 (2006.01)
A61K 31/66 (2006.01)
A61K 45/06 (2006.01)
A61L 31/16 (2006.01)
A61K 31/4418 (2006.01)
A61K 31/165 (2006.01)
A61K 31/4412 (2006.01)
A61K 31/00 (2006.01)
A61K 31/443 (2006.01)
G01N 33/574 (2006.01)
A61K 31/16 (2006.01)
G01N 33/50 (2006.01)

(52) U.S. Cl.
CPC .................. A61K 45/06 (2013.01); A61K 31/66 (2013.01); A61L 31/16 (2013.01); A61K 31/4418 (2013.01); A61L 2300/204 (2013.01); A61L 2300/416 (2013.01); A61K 31/165 (2013.01); A61K 31/4412 (2013.01); A61K 31/00 (2013.01); A61K 31/443 (2013.01); G01N 33/5743 (2013.01); A61K 31/16 (2013.01); G01N 33/5041 (2013.01); G01N 33/57438 (2013.01)
USPC .......................................................... 514/183

(58) Field of Classification Search
CPC ....................................................... A61K 38/00
USPC ............................................................ 514/189
See application file for complete search history.

(56) References Cited

U.S. PATENT DOCUMENTS

| 502,504 A | 8/1893 | Thoms |
|---|---|---|
| 1,792,156 A | 2/1931 | Fitzky |
| 2,046,375 A | 7/1936 | Goldstein et al. |
| 2,093,265 A | 9/1937 | Coffey et al. |
| 2,288,422 A | 6/1942 | Rohm |
| 2,649,476 A | 8/1953 | Martin |
| 2,683,082 A | 7/1954 | Hill et al. |
| 2,722,544 A | 11/1955 | Martin |
| 2,745,874 A | 5/1956 | Schetty et al. |
| 2,781,330 A | 2/1957 | Downey |
| 2,797,214 A | 6/1957 | Bossard |
| 2,867,659 A | 1/1959 | Model et al. |
| 2,877,268 A | 3/1959 | Applegath et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,284,433 A | 11/1966 | Becker et al. |
| 3,424,760 A | 1/1969 | Helsley et al. |
| 3,424,761 A | 1/1969 | Helsley et al. |
| 3,424,762 A | 1/1969 | Helsley |
| 3,547,940 A | 12/1970 | Brantley |
| 3,639,668 A | 2/1972 | Alles et al. |
| 3,646,059 A | 2/1972 | Brantley |
| 3,668,222 A | 6/1972 | Hauser |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |

(Continued)

FOREIGN PATENT DOCUMENTS

CA 2028536 A1 4/1991
CA 2 146 707 A1 10/1995

(Continued)

OTHER PUBLICATIONS

R. Board, G.C. Jayson, Drug Resistance Updates 8 (2005) 75-83.*
Kyriakis et al, (1992) "Raf-1 activates MAP kinase-kinase" in Nature vol. 358, pp. 417-421.*
Kumar et al (Exper Opin. Emerging Drugs 6(2) (2001) 303-315).*
Lyons et al (Endocrine-Related Cancer, 8 (2001) 219-225).*
Leu et al (Proc Am Soc Clin Oncol 21: 2002 (abstr 1774)).*
Arzneimitteltherapie, "Sorafenib" Oct. 6, 2006, Auflage 18498, 7 pages English translation.

(Continued)

Primary Examiner — Benjamin Packard
(74) Attorney, Agent, or Firm — Millen, White, Zelano & Branigan, P.C.

(57) ABSTRACT

The present invention provides methods for treating and/or preventing conditions and diseases in humans and other mammals that are associated with and/or mediated by signal transduction pathways comprising platelet-derived growth factor receptor (PDGFR) by administering diaryl ureas of Formula I. The present invention also provides devices and methods for treating, ameliorating, preventing, or modulating restenosis following angioplastic surgery or other invasive procedures that affect or injure the vascular system, and graft rejection following transplantation of a donor tissue into a host, where a stent or other omplantable device comprises an effective amount of diaryl ureas of Formula I.

55 Claims, No Drawings

(56) References Cited

U.S. PATENT DOCUMENTS

| | | |
|---|---|---|
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,063,928 A | 12/1977 | Johnston |
| 4,071,524 A | 1/1978 | Banitt |
| 4,103,022 A | 7/1978 | Sirrenberg et al. |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,279,639 A | 7/1981 | Okamoto et al. |
| 4,293,328 A | 10/1981 | Yukinaga et al. |
| 4,358,596 A | 11/1982 | Krüger |
| 4,405,644 A | 9/1983 | Kabbe et al. |
| 4,410,697 A | 10/1983 | Török et al. |
| 4,437,878 A | 3/1984 | Acker et al. |
| 4,468,380 A | 8/1984 | O'Doherty et al. |
| 4,473,579 A | 9/1984 | Devries et al. |
| 4,499,097 A | 2/1985 | Tomcufcik et al. |
| 4,511,571 A | 4/1985 | Böger et al. |
| 4,514,571 A | 4/1985 | Nakai et al. |
| 4,526,997 A | 7/1985 | O'Doherty et al. |
| 4,540,566 A | 9/1985 | Davis et al. |
| 4,546,191 A | 10/1985 | Nishiyama et al. |
| 4,587,240 A | 5/1986 | Hider et al. |
| 4,623,662 A | 11/1986 | DeVries |
| 4,643,849 A | 2/1987 | Hirai et al. |
| 4,740,520 A | 4/1988 | Hallenbach et al. |
| 4,760,063 A | 7/1988 | Hallenbach et al. |
| 4,775,763 A | 10/1988 | Dalton et al. |
| 4,808,588 A | 2/1989 | King |
| 4,820,871 A | 4/1989 | Kissener et al. |
| 4,863,924 A | 9/1989 | Haga et al. |
| 4,921,525 A | 5/1990 | Grossman et al. |
| 4,973,675 A | 11/1990 | Israel et al. |
| 4,977,169 A | 12/1990 | Häusermann et al. |
| 4,983,605 A | 1/1991 | Kondo et al. |
| 4,985,449 A | 1/1991 | Haga et al. |
| 4,996,325 A | 2/1991 | Kristinsson |
| 5,036,072 A | 7/1991 | Nakajima et al. |
| 5,059,614 A | 10/1991 | Lepage et al. |
| 5,063,247 A | 11/1991 | Sekiya et al. |
| 5,098,907 A | 3/1992 | Kondo et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,331 A | 7/1992 | Pascual |
| 5,151,344 A | 9/1992 | Abe et al. |
| 5,151,413 A | 9/1992 | Caufield et al. |
| 5,162,360 A | 11/1992 | Creswell et al. |
| 5,177,110 A | 1/1993 | Oechslein et al. |
| 5,185,358 A | 2/1993 | Creswell et al. |
| 5,256,790 A | 10/1993 | Nelson |
| 5,258,389 A | 11/1993 | Goulet et al. |
| 5,270,458 A | 12/1993 | Lemischka |
| 5,283,354 A | 2/1994 | Lemischka |
| 5,312,820 A | 5/1994 | Ashton et al. |
| 5,319,099 A | 6/1994 | Kamata et al. |
| 5,378,725 A | 1/1995 | Bonjouklian et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,441,947 A | 8/1995 | Dodge et al. |
| 5,447,957 A | 9/1995 | Adams et al. |
| 5,456,920 A | 10/1995 | Matoba et al. |
| 5,468,773 A | 11/1995 | Dodge et al. |
| 5,470,882 A | 11/1995 | Dixon et al. |
| 5,480,906 A | 1/1996 | Creemer et al. |
| 5,500,424 A | 3/1996 | Nagamine et al. |
| 5,508,288 A | 4/1996 | Forbes et al. |
| 5,547,966 A | 8/1996 | Atwal et al. |
| 5,559,137 A | 9/1996 | Adams et al. |
| 5,596,001 A | 1/1997 | Hamanaka |
| 5,597,719 A | 1/1997 | Freed et al. |
| 5,624,937 A | 4/1997 | Reel et al. |
| 5,656,612 A | 8/1997 | Monia |
| 5,658,903 A | 8/1997 | Adams et al. |
| 5,667,226 A | 9/1997 | Janich |
| 5,696,138 A | 12/1997 | Olesen et al. |
| 5,698,581 A | 12/1997 | Kleemann et al. |
| 5,710,094 A | 1/1998 | Minami et al. |
| 5,721,237 A | 2/1998 | Myers et al. |
| 5,726,167 A | 3/1998 | Dodge et al. |
| 5,747,498 A | 5/1998 | Schnur et al. |
| 5,773,459 A | 6/1998 | Tang et al. |
| 5,777,097 A | 7/1998 | Lee et al. |
| 5,780,262 A | 7/1998 | Brent et al. |
| 5,780,483 A | 7/1998 | Widdowson et al. |
| 5,783,664 A | 7/1998 | Lee et al. |
| 5,786,362 A | 7/1998 | Krongrad |
| 5,801,794 A | 9/1998 | Lehureau et al. |
| 5,807,876 A | 9/1998 | Armistead et al. |
| 5,807,891 A | 9/1998 | Bold et al. |
| 5,808,080 A | 9/1998 | Bell et al. |
| 5,814,646 A | 9/1998 | Heinz et al. |
| 5,869,043 A | 2/1999 | McDonnell et al. |
| 5,871,934 A | 2/1999 | Lee et al. |
| 5,886,044 A | 3/1999 | Widdowson et al. |
| 5,891,895 A | 4/1999 | Shiraishi et al. |
| 5,908,865 A | 6/1999 | Doi et al. |
| 5,919,773 A | 7/1999 | Monia et al. |
| 5,929,250 A | 7/1999 | Widdowson et al. |
| 5,955,366 A | 9/1999 | Lee et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,017,692 A | 1/2000 | Brent et al. |
| 6,020,345 A | 2/2000 | Vacher et al. |
| 6,022,884 A | 2/2000 | Mantlo et al. |
| 6,025,151 A | 2/2000 | Peterson |
| 6,033,873 A | 3/2000 | McDonnell et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,103,692 A | 8/2000 | Avruch et al. |
| 6,114,517 A | 9/2000 | Monia et al. |
| 6,130,053 A | 10/2000 | Thompson et al. |
| 6,133,319 A | 10/2000 | Widdowson |
| 6,136,779 A | 10/2000 | Foulkes et al. |
| 6,143,764 A | 11/2000 | Kubo et al. |
| 6,147,107 A | 11/2000 | Dent et al. |
| 6,147,116 A | 11/2000 | Barbachyn et al. |
| 6,150,415 A | 11/2000 | Hammock et al. |
| 6,159,901 A | 12/2000 | Kanno et al. |
| 6,174,901 B1 | 1/2001 | Mantlo et al. |
| 6,177,401 B1 | 1/2001 | Ullrich et al. |
| 6,178,399 B1 | 1/2001 | Takebayashi et al. |
| 6,180,631 B1 | 1/2001 | McMahon et al. |
| 6,180,675 B1 | 1/2001 | Widdowson et al. |
| 6,187,799 B1 | 2/2001 | Wood et al. |
| 6,193,965 B1 | 2/2001 | Karin et al. |
| 6,204,267 B1 | 3/2001 | Tang et al. |
| 6,210,710 B1 | 4/2001 | Skinner |
| 6,211,373 B1 | 4/2001 | Widdowson et al. |
| 6,218,539 B1 | 4/2001 | Widdowson |
| 6,228,881 B1 | 5/2001 | Regan et al. |
| 6,235,764 B1 | 5/2001 | Larson et al. |
| 6,236,125 B1 | 5/2001 | Oudet et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,294,350 B1 | 9/2001 | Peterson |

(56) References Cited

U.S. PATENT DOCUMENTS

| | | |
|---|---|---|
| 6,297,381 B1 | 10/2001 | Cirillo et al. |
| 6,310,068 B1 | 10/2001 | Böttcher et al. |
| 6,316,462 B1 | 11/2001 | Bishop et al. |
| 6,319,921 B1 | 11/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,352,977 B1 | 3/2002 | Astles et al. |
| 6,358,525 B1 | 3/2002 | Guo et al. |
| 6,358,945 B1 | 3/2002 | Breitfelder et al. |
| 6,361,773 B1 | 3/2002 | Lee et al. |
| 6,372,773 B1 | 4/2002 | Regan |
| 6,372,933 B1 | 4/2002 | Baine et al. |
| 6,380,218 B1 | 4/2002 | Marfat et al. |
| 6,383,734 B1 | 5/2002 | Marshall et al. |
| 6,387,900 B1 | 5/2002 | Pevarello et al. |
| 6,391,917 B1 | 5/2002 | Petrie et al. |
| 6,403,588 B1 | 6/2002 | Hayakawa et al. |
| 6,414,011 B1 | 7/2002 | Hogenkamp et al. |
| 6,444,691 B1 | 9/2002 | Oremus et al. |
| 6,448,079 B1 | 9/2002 | Monia et al. |
| 6,479,519 B1 | 11/2002 | Astles et al. |
| 6,492,393 B1 | 12/2002 | Breitfelder et al. |
| 6,495,331 B1 | 12/2002 | Gelfand et al. |
| 6,500,863 B1 | 12/2002 | Jin et al. |
| 6,511,800 B1 | 1/2003 | Singh |
| 6,511,997 B1 | 1/2003 | Minami et al. |
| 6,521,407 B1 | 2/2003 | Warenius et al. |
| 6,521,592 B2 | 2/2003 | Ko et al. |
| 6,524,832 B1 | 2/2003 | Kufe et al. |
| 6,525,046 B1 | 2/2003 | Cirillo et al. |
| 6,525,065 B1 | 2/2003 | Caldwell et al. |
| 6,525,091 B2 | 2/2003 | Robinson et al. |
| 6,583,282 B1 | 6/2003 | Zhang et al. |
| 6,608,052 B2 | 8/2003 | Breitfelder et al. |
| 6,617,324 B1 | 9/2003 | Naraian et al. |
| 6,635,421 B1 | 10/2003 | Klagsbrun et al. |
| 6,653,320 B2 | 11/2003 | Hayakawa et al. |
| 6,656,963 B2 | 12/2003 | Firestone et al. |
| 6,673,777 B1 | 1/2004 | Tracey et al. |
| 6,689,560 B1 | 2/2004 | Rapp et al. |
| 6,797,823 B1 | 9/2004 | Kubo et al. |
| 6,958,333 B1 | 10/2005 | Hayama et al. |
| 7,070,968 B2 | 7/2006 | Kufe et al. |
| 7,235,576 B1 * | 6/2007 | Riedl et al. .................. 514/388 |
| 7,253,286 B2 | 8/2007 | Funahashi et al. |
| 7,307,071 B2 | 12/2007 | Lyons et al. |
| 7,329,670 B1 | 2/2008 | Dumas et al. |
| 7,351,834 B1 | 4/2008 | Riedl et al. |
| 7,371,763 B2 | 5/2008 | Dumas et al. |
| 7,517,880 B2 | 4/2009 | Miller et al. |
| 7,528,255 B2 | 5/2009 | Riedl et al. |
| 7,547,695 B2 | 6/2009 | Hoelzemann et al. |
| 7,557,129 B2 | 7/2009 | Scott et al. |
| 7,605,261 B2 | 10/2009 | Deprez et al. |
| 7,612,092 B2 | 11/2009 | Funahashi et al. |
| 7,678,811 B2 | 3/2010 | Dumas et al. |
| 2001/0006975 A1 | 7/2001 | Wood et al. |
| 2001/0011135 A1 * | 8/2001 | Riedl et al. .................. 546/264 |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2001/0038842 A1 | 11/2001 | Achen et al. |
| 2002/0037276 A1 | 3/2002 | Ptasznik et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0111495 A1 | 8/2002 | Magee et al. |
| 2002/0128321 A1 | 9/2002 | Widdowson et al. |
| 2002/0137774 A1 | 9/2002 | Riedl et al. |
| 2002/0161014 A1 | 10/2002 | Sadhu et al. |
| 2002/0165275 A1 | 11/2002 | Wu et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2002/0188027 A1 | 12/2002 | Robinson et al. |
| 2002/0197256 A1 | 12/2002 | Grewal |
| 2003/0069284 A1 | 4/2003 | Keegan et al. |
| 2003/0105091 A1 | 6/2003 | Riedl et al. |
| 2003/0125359 A1 | 7/2003 | Lyons et al. |
| 2003/0130309 A1 | 7/2003 | Moss et al. |
| 2003/0139605 A1 | 7/2003 | Riedl et al. |
| 2003/0144278 A1 | 7/2003 | Riedl et al. |
| 2003/0157104 A1 | 8/2003 | Waksal |
| 2003/0181442 A1 | 9/2003 | Riedl et al. |
| 2003/0207870 A1 | 11/2003 | Dumas et al. |
| 2003/0207872 A1 | 11/2003 | Riedl et al. |
| 2003/0207914 A1 | 11/2003 | Dumas et al. |
| 2003/0216396 A1 | 11/2003 | Dumas et al. |
| 2003/0216446 A1 | 11/2003 | Dumas et al. |
| 2003/0232400 A1 | 12/2003 | Radka et al. |
| 2003/0232765 A1 | 12/2003 | Carter et al. |
| 2004/0023961 A1 | 2/2004 | Dumas et al. |
| 2004/0052880 A1 | 3/2004 | Kobayashi et al. |
| 2004/0096855 A1 | 5/2004 | Stratton et al. |
| 2004/0147541 A1 | 7/2004 | Lane et al. |
| 2004/0192770 A1 | 9/2004 | Kozikowski et al. |
| 2004/0197256 A1 | 10/2004 | Rogers et al. |
| 2004/0209905 A1 | 10/2004 | Kubo et al. |
| 2004/0224937 A1 | 11/2004 | Furness et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0038080 A1 | 2/2005 | Boyer et al. |
| 2005/0059703 A1 | 3/2005 | Wilhelm et al. |
| 2005/0069963 A1 | 3/2005 | Lokshin et al. |
| 2005/0096344 A1 | 5/2005 | Fraley et al. |
| 2005/0175737 A1 | 8/2005 | Knobel |
| 2005/0256174 A1 | 11/2005 | Wood et al. |
| 2005/0288286 A1 | 12/2005 | Flynn et al. |
| 2006/0058358 A1 | 3/2006 | Dumas et al. |
| 2006/0078617 A1 | 4/2006 | Schueckler |
| 2006/0211738 A1 | 9/2006 | Mitchell et al. |
| 2006/0234931 A1 | 10/2006 | Biggs, III et al. |
| 2006/0241301 A1 | 10/2006 | Hoelzemann et al. |
| 2006/0247186 A1 | 11/2006 | Carter et al. |
| 2006/0281762 A1 | 12/2006 | Staehle et al. |
| 2007/0020704 A1 | 1/2007 | Wilhelm et al. |
| 2007/0037224 A1 | 2/2007 | Hamer et al. |
| 2007/0066660 A1 | 3/2007 | Stahle et al. |
| 2007/0105142 A1 | 5/2007 | Wilhelm |
| 2007/0149594 A1 | 6/2007 | Finsinger et al. |
| 2007/0173514 A1 | 7/2007 | Moss et al. |
| 2007/0178494 A1 | 8/2007 | Elting et al. |
| 2007/0244120 A1 | 10/2007 | Dumas et al. |
| 2007/0254295 A1 | 11/2007 | Harvey et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0045546 A1 | 2/2008 | Bouchon et al. |
| 2008/0045589 A1 | 2/2008 | Kelley |
| 2008/0085902 A1 | 4/2008 | Bold et al. |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0207699 A1 | 8/2008 | Hoelzemann et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0262236 A1 | 10/2008 | Logers et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2008/0311604 A1 | 12/2008 | Elting et al. |
| 2009/0068146 A1 | 3/2009 | Wilhelm |

(56) References Cited

U.S. PATENT DOCUMENTS

| | | |
|---|---|---|
| 2009/0093526 A1 | 4/2009 | Miller et al. |
| 2009/0118268 A1 | 5/2009 | Riedl et al. |
| 2009/0176791 A1 | 7/2009 | Sandner et al. |
| 2009/0192127 A1 | 7/2009 | Scheuring et al. |
| 2009/0215833 A1 | 8/2009 | Grunenberg et al. |
| 2009/0215835 A1 | 8/2009 | Wilhelm |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0035888 A1 | 2/2010 | Sandner et al. |
| 2010/0063088 A1 | 3/2010 | Wood et al. |

FOREIGN PATENT DOCUMENTS

| | | |
|---|---|---|
| CH | 479557 | 11/1969 |
| CL | 38688 | 6/1993 |
| DE | 487014 C1 | 11/1929 |
| DE | 511468 C1 | 10/1930 |
| DE | 523437 C1 | 4/1931 |
| DE | 2436179 A1 | 2/1975 |
| DE | 2501648 A1 | 7/1975 |
| DE | 3305866 A1 | 8/1984 |
| DE | 2436179 C2 | 4/1986 |
| DE | 3529247 A1 | 11/1986 |
| DE | 3540377 A1 | 5/1987 |
| DE | 253997 A1 | 2/1988 |
| EP | 0016371 A1 | 10/1980 |
| EP | 0107214 A2 | 5/1984 |
| EP | 0116932 A1 | 8/1984 |
| EP | 0192263 A2 | 8/1986 |
| EP | 0202538 A1 | 11/1986 |
| EP | 0230400 A2 | 7/1987 |
| EP | 0233559 A1 | 8/1987 |
| EP | 0242666 A1 | 10/1987 |
| EP | 0264904 A2 | 4/1988 |
| EP | 0314615 A2 | 5/1989 |
| EP | 0335156 A1 | 10/1989 |
| EP | 0359148 A1 | 3/1990 |
| EP | 0371876 A1 | 6/1990 |
| EP | 0379915 A1 | 8/1990 |
| EP | 0380048 A2 | 8/1990 |
| EP | 0381987 A1 | 8/1990 |
| EP | 0405233 A1 | 1/1991 |
| EP | 0425443 A1 | 5/1991 |
| EP | 0459887 A1 | 12/1991 |
| EP | 0233559 B1 | 5/1992 |
| EP | 0192263 B1 | 7/1992 |
| EP | 0502504 A1 | 9/1992 |
| EP | 0509795 A2 | 10/1992 |
| EP | 0676395 A2 | 10/1995 |
| EP | 0690344 A1 | 1/1996 |
| EP | 0709220 A1 | 5/1996 |
| EP | 0709225 A1 | 5/1996 |
| EP | 0709225 B1 | 8/1998 |
| EP | 0860433 A1 | 8/1998 |
| EP | 1056725 A1 | 12/2000 |
| EP | 1199306 A1 | 4/2002 |
| EP | 1256587 A1 | 11/2002 |
| EP | 1537075 A0 | 6/2005 |
| FR | 1457172 A | 9/1966 |
| GB | 771333 | 3/1957 |
| GB | 828231 | 2/1960 |
| GB | 921682 | 3/1963 |
| GB | 1110099 | 4/1968 |
| GB | 1111554 | 5/1968 |
| GB | 11115554 | 5/1968 |
| GB | 1590870 | 6/1981 |
| HU | P0004437 | 6/1981 |
| HU | P0004437 | 6/2001 |
| IR | 26555 | 1/2000 |
| JP | 44-2569 B | 2/1969 |
| JP | 50-76072 A | 6/1975 |
| JP | 50-77375 A | 6/1975 |
| JP | 50-149668 A | 11/1975 |
| JP | 51-63170 A | 6/1976 |
| JP | 51-80862 A | 7/1976 |
| JP | 53-86033 A | 7/1978 |
| JP | 54-32468 A | 9/1979 |
| JP | 55-98152 A | 7/1980 |
| JP | 55-124763 A | 9/1980 |
| JP | 55-162772 A | 12/1980 |
| JP | 57-53785 B2 | 11/1982 |
| JP | 58-21626 B2 | 5/1983 |
| JP | 61-20039 A | 1/1986 |
| JP | 63-214752 A | 9/1988 |
| JP | 64-9455 A | 1/1989 |
| JP | 1-102461 A | 4/1989 |
| JP | 1-132580 A | 5/1989 |
| JP | 1-200254 A | 8/1989 |
| JP | 1-259360 A | 10/1989 |
| JP | 2-22650 A | 1/1990 |
| JP | 2-23337 A | 1/1990 |
| JP | 2-35450 A | 2/1990 |
| JP | 2-105146 A | 4/1990 |
| JP | 2-108048 A | 4/1990 |
| JP | 2-150840 A | 6/1990 |
| JP | 3-53247 A | 3/1991 |
| JP | 3-144634 A | 6/1991 |
| JP | 3-198049 A | 8/1991 |
| JP | 6-75172 B2 | 9/1994 |
| JP | 8-301841 A | 11/1996 |
| JP | 10-306078 A | 11/1998 |
| JP | 6124 | 1/2000 |
| LB | 6124 | 1/2000 |
| WO | WO 90/02112 A1 | 3/1990 |
| WO | WO 92/03413 A1 | 3/1992 |
| WO | WO 92/05179 A1 | 4/1992 |
| WO | WO 93/04170 A1 | 3/1993 |
| WO | WO 93/18028 A1 | 9/1993 |
| WO | WO 93/21458 A1 | 12/1993 |
| WO | WO 94/02136 A1 | 2/1994 |
| WO | WO 94/02485 A1 | 2/1994 |
| WO | WO 94/04541 A2 | 3/1994 |
| WO | WO 94/14801 A1 | 7/1994 |
| WO | WO 94/18170 A1 | 8/1994 |
| WO | WO 94/22807 A1 | 10/1994 |
| WO | WO 94/23755 A1 | 10/1994 |
| WO | WO 94/25012 A2 | 11/1994 |
| WO | WO 95/02136 A1 | 1/1995 |
| WO | WO 95/02591 A1 | 1/1995 |
| WO | WO 95/07922 A1 | 3/1995 |
| WO | WO 95/13067 A1 | 5/1995 |
| WO | WO 95/14023 A1 | 5/1995 |
| WO | WO 95/16691 A1 | 6/1995 |
| WO | WO 95/19169 A2 | 7/1995 |
| WO | WO 95/31451 A1 | 11/1995 |
| WO | WO 95/33458 A1 | 12/1995 |
| WO | WO 95/33460 A1 | 12/1995 |
| WO | WO 96/02112 A1 | 1/1996 |
| WO | WO 96/13632 A1 | 5/1996 |
| WO | WO 96/25157 A1 | 8/1996 |
| WO | WO 96/40673 A1 | 12/1996 |
| WO | WO 96/40675 A1 | 12/1996 |
| WO | WO 96/41807 A1 | 12/1996 |
| WO | WO 97/03069 A1 | 1/1997 |
| WO | WO 97/09973 A2 | 3/1997 |
| WO | WO 97/17267 A1 | 5/1997 |
| WO | WO 97/17329 A1 | 5/1997 |
| WO | WO 97/29743 A1 | 8/1997 |
| WO | WO 97/30992 A1 | 8/1997 |
| WO | WO 97/34146 A1 | 9/1997 |
| WO | WO 97/40028 A1 | 10/1997 |
| WO | WO 97/40842 A1 | 11/1997 |
| WO | WO 97/45400 A1 | 12/1997 |
| WO | WO 97/49399 A1 | 12/1997 |
| WO | WO 97/49400 A1 | 12/1997 |
| WO | WO 98/17207 A1 | 4/1998 |
| WO | WO 98/17267 A1 | 4/1998 |
| WO | WO 98/20868 A1 | 5/1998 |
| WO | WO 98/22103 A1 | 5/1998 |
| WO | WO 98/22432 A1 | 5/1998 |
| WO | WO 98/32439 A1 | 7/1998 |
| WO | WO 98/34929 A1 | 8/1998 |

(56) References Cited

FOREIGN PATENT DOCUMENTS

| | | |
|---|---|---|
| WO | WO 98/45268 A1 | 10/1998 |
| WO | WO 98/49150 A1 | 11/1998 |
| WO | WO 98/52558 A1 | 11/1998 |
| WO | WO 98/52559 A1 | 11/1998 |
| WO | WO 98/52937 A2 | 11/1998 |
| WO | WO 98/52941 A1 | 11/1998 |
| WO | WO 98/56377 A1 | 12/1998 |
| WO | WO 99/00357 A1 | 1/1999 |
| WO | WO 99/00370 A1 | 1/1999 |
| WO | WO 99/20617 A1 | 4/1999 |
| WO | WO 99/21835 A1 | 5/1999 |
| WO | WO 99/23091 A1 | 5/1999 |
| WO | WO 99/24035 A1 | 5/1999 |
| WO | WO 99/24398 A2 | 5/1999 |
| WO | WO 99/24635 A1 | 5/1999 |
| WO | WO 99/26657 A1 | 6/1999 |
| WO | WO 99/28305 A1 | 6/1999 |
| WO | WO 99/32106 A1 | 7/1999 |
| WO | WO 99/32109 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/32437 A1 | 7/1999 |
| WO | WO 99/32455 A1 | 7/1999 |
| WO | WO 99/32463 A1 | 7/1999 |
| WO | WO 99/33458 A1 | 7/1999 |
| WO | WO 99/35132 A1 | 7/1999 |
| WO | WO 99/40673 A1 | 8/1999 |
| WO | WO 99/58502 A1 | 11/1999 |
| WO | WO 99/62890 A1 | 12/1999 |
| WO | WO 00/12497 A2 | 3/2000 |
| WO | WO 00/17175 A1 | 3/2000 |
| WO | WO 00/19205 A1 | 4/2000 |
| WO | WO 00/26203 A1 | 5/2000 |
| WO | WO 00/27414 A2 | 5/2000 |
| WO | WO 00/31238 A2 | 6/2000 |
| WO | WO 00/34303 A1 | 6/2000 |
| WO | WO 00/35454 A1 | 6/2000 |
| WO | WO 00/35455 A1 | 6/2000 |
| WO | WO 00/39101 A1 | 7/2000 |
| WO | WO 00/39116 A1 | 7/2000 |
| WO | WO 00/41366 A1 | 7/2000 |
| WO | WO 00/41698 A1 | 7/2000 |
| WO | WO 00/42012 A1 | 7/2000 |
| WO | WO 00/43384 A1 | 7/2000 |
| WO | WO 00/47577 A1 | 8/2000 |
| WO | WO 00/50425 A1 | 8/2000 |
| WO | WO 00/55139 A2 | 9/2000 |
| WO | WO 00/55152 A1 | 9/2000 |
| WO | WO 00/56331 A1 | 9/2000 |
| WO | WO 00/71506 A2 | 11/2000 |
| WO | WO 00/71532 A1 | 11/2000 |
| WO | WO 01/04115 A2 | 1/2001 |
| WO | WO 01/07411 A1 | 2/2001 |
| WO | WO 01/09088 A1 | 2/2001 |
| WO | WO 01/12188 A1 | 2/2001 |
| WO | WO 01/36403 A1 | 5/2001 |
| WO | WO 01/47892 A1 | 7/2001 |
| WO | WO 01/54723 A1 | 8/2001 |
| WO | WO 01/54727 A1 | 8/2001 |
| WO | WO 01/57008 A1 | 8/2001 |
| WO | WO 01/63403 A2 | 8/2001 |
| WO | WO 01/66099 A2 | 9/2001 |
| WO | WO 01/66540 A1 | 9/2001 |
| WO | WO 01/80843 A2 | 11/2001 |
| WO | WO 02/06382 A1 | 1/2002 |
| WO | WO 02/07747 A1 | 1/2002 |
| WO | WO 02/07772 A2 | 1/2002 |
| WO | WO 02/10141 A2 | 2/2002 |
| WO | WO 02/14281 A1 | 2/2002 |
| WO | WO 02/14311 A2 | 2/2002 |
| WO | WO 02/18346 A1 | 3/2002 |
| WO | WO 02/24635 A2 | 3/2002 |
| WO | WO 02/25286 A2 | 3/2002 |
| WO | WO 02/32872 A1 | 4/2002 |
| WO | WO 02/40445 A1 | 5/2002 |
| WO | WO 02/42012 A1 | 5/2002 |
| WO | WO 02/44156 A2 | 6/2002 |
| WO | WO 02/44158 A1 | 6/2002 |
| WO | WO 02/50091 A1 | 6/2002 |
| WO | WO 02/059081 A2 | 8/2002 |
| WO | WO 02/059102 A2 | 8/2002 |
| WO | WO 02/060900 A2 | 8/2002 |
| WO | WO 02/062763 A2 | 8/2002 |
| WO | WO 02/070008 A1 | 9/2002 |
| WO | WO 02/076930 A2 | 10/2002 |
| WO | WO 02/076977 A2 | 10/2002 |
| WO | WO 02/083628 A1 | 10/2002 |
| WO | WO 02/083642 A1 | 10/2002 |
| WO | WO 02/085857 A2 | 10/2002 |
| WO | WO 02/085859 A1 | 10/2002 |
| WO | WO 02/088090 A2 | 11/2002 |
| WO | WO 02/092576 A1 | 11/2002 |
| WO | WO 03/004523 A1 | 1/2003 |
| WO | WO 03/005999 A2 | 1/2003 |
| WO | WO 03/047523 A2 | 6/2003 |
| WO | WO 03/047579 A1 | 6/2003 |
| WO | WO 03/056036 A2 | 7/2003 |
| WO | WO 03/059373 A2 | 7/2003 |
| WO | WO 03/060111 A2 | 7/2003 |
| WO | WO 03/065995 A2 | 8/2003 |
| WO | WO 03/068223 A1 | 8/2003 |
| WO | WO 03/068228 A1 | 8/2003 |
| WO | WO 03/068229 A1 | 8/2003 |
| WO | WO 03/068746 A1 | 8/2003 |
| WO | WO 03/082272 A1 | 10/2003 |
| WO | WO 03/094626 A1 | 11/2003 |
| WO | WO 03/097854 A2 | 11/2003 |
| WO | WO 03/099771 A2 | 12/2003 |
| WO | WO 2004/004720 A1 | 1/2004 |
| WO | WO 2004/019941 A1 | 3/2004 |
| WO | WO 2004/037789 A2 | 5/2004 |
| WO | WO 2004/043374 A2 | 5/2004 |
| WO | WO 2004/045578 A2 | 6/2004 |
| WO | WO 2004/052880 A1 | 6/2004 |
| WO | WO 2004/078128 A2 | 9/2004 |
| WO | WO 2004/078746 A2 | 9/2004 |
| WO | WO 2004/078747 A1 | 9/2004 |
| WO | WO 2004/078748 A2 | 9/2004 |
| WO | WO 2004/085399 A1 | 10/2004 |
| WO | WO 2004/085425 A1 | 10/2004 |
| WO | WO 2004/108713 A1 | 12/2004 |
| WO | WO 2004/108715 A1 | 12/2004 |
| WO | WO 2004/113274 A2 | 12/2004 |
| WO | WO 2005/000284 A2 | 1/2005 |
| WO | WO 2005/002673 A1 | 1/2005 |
| WO | WO 2005/004863 A1 | 1/2005 |
| WO | WO 2005/004864 A1 | 1/2005 |
| WO | WO 2005/005389 A2 | 1/2005 |
| WO | WO 2005/005434 A1 | 1/2005 |
| WO | WO 2005/009367 A2 | 2/2005 |
| WO | WO 2005/009961 A2 | 2/2005 |
| WO | WO 2005/011700 A1 | 2/2005 |
| WO | WO 2005/016252 A2 | 2/2005 |
| WO | WO 2005/019192 A1 | 3/2005 |
| WO | WO 2005/032548 A1 | 4/2005 |
| WO | WO 2005/037273 A1 | 4/2005 |
| WO | WO 2005/037285 A1 | 4/2005 |
| WO | WO 2005/037829 A1 | 4/2005 |
| WO | WO 2005/042520 A1 | 5/2005 |
| WO | WO 2005/047283 A1 | 5/2005 |
| WO | WO 2005/048948 A2 | 6/2005 |
| WO | WO 2005/049603 A1 | 6/2005 |
| WO | WO 2005/056764 A2 | 6/2005 |
| WO | WO 2005/058832 A1 | 6/2005 |
| WO | WO 2005/059179 A1 | 6/2005 |
| WO | WO 2005/075425 A2 | 8/2005 |
| WO | WO 2005/089443 A2 | 9/2005 |
| WO | WO 2005/110994 A2 | 11/2005 |
| WO | WO 2006/026500 A1 | 3/2006 |
| WO | WO 2006/026501 A1 | 3/2006 |
| WO | WO 2006/027346 A2 | 3/2006 |
| WO | WO 2006/034797 A1 | 4/2006 |
| WO | WO 2006/094626 A1 | 9/2006 |

(56) References Cited

FOREIGN PATENT DOCUMENTS

| | | |
|---|---|---|
| WO | WO 2006/105844 A1 | 10/2006 |
| WO | WO 2006/125540 A1 | 11/2006 |
| WO | WO 2007/015947 A2 | 2/2007 |
| WO | WO 2007/039403 A1 | 4/2007 |
| WO | WO 2007/039404 A1 | 4/2007 |
| WO | WO 2007/047955 A2 | 4/2007 |
| WO | WO 2007/053573 A2 | 5/2007 |
| WO | WO 2007/054215 A1 | 5/2007 |
| WO | WO 2007/056011 A2 | 5/2007 |
| WO | WO 2007/056012 A2 | 5/2007 |
| WO | WO 2007/059094 A2 | 5/2007 |
| WO | WO 2007/059154 A2 | 5/2007 |
| WO | WO 2007/059155 A1 | 5/2007 |
| WO | WO 2007/064872 A2 | 6/2007 |
| WO | WO 2007/087575 A2 | 8/2007 |
| WO | WO 2007/096393 A1 | 8/2007 |
| WO | WO 2007/096395 A1 | 8/2007 |
| WO | WO 2007/123722 A2 | 11/2007 |
| WO | WO 2007/139930 A2 | 12/2007 |
| WO | WO 2008/055966 A1 | 5/2008 |
| WO | WO 2008/079968 A1 | 7/2008 |
| WO | WO 2008/079972 A2 | 7/2008 |
| WO | WO 2008/089389 A2 | 7/2008 |
| WO | WO 2009/034308 A2 | 3/2009 |
| WO | WO 2009/054004 A2 | 4/2009 |

OTHER PUBLICATIONS

Foussard-Blanpin, Odette, "Comparative pharmacological study of substituted carboxamides upon central nervous system," Ann. Pharm. Fr. (1982), 40 (4), pp. 339-350 English translation.

Garbe, "Auch ein Therapieplatz für Sorafenib?" Medical Special (2006) 2 pages English translation.

Dehtling, J. "Große Onkologie-Pipeline" Medizinische Monatsschrift für Pharmazeuten, 2006, Auflage 12914, 2 pages English translation.

Drevs, J., Die Medizinische Welt, 2006, pp. 1/5,2/5, 3/5, 4/5, 5/5 English translation.

Jungmayr, P., "Aktueller Stand der Krebstherapie," Deutsche Apotheker Zeitung, Sep. 30, 2004, Auflage ca. 36.000 English translation.

Kempter et al., "Synthese potentieller Pflanzenschutz- und Schädlingsbekämpfungsmittel aus substituierten Anilinen," Pädagogsische Hochschule, Eingegangen am Jan. 7, 1982, vol. 27, Issue 1, 101-120 (1983) English translation.

Kuefer et al., "Translational research in renal cell cancer. Illustrated by the example of the vascular endothelial growth factor pathway," Der Urologe, 2006, vol. 45, No. 3, pp. 328, 330-335 English translation.

Kurik et al., "Optical Properties of Segmented Oligourethane with Azomethine Terminal Fragments," Polymer Science, series B, 1996, vol. 38 pp. 2038-2041 English translation.

Medinger et al., "Hemmung der Tumorangiogenese Neue Therapieoption in der Onkologie,"Med Welt, 2006, 57, pp. 437-441 English translation.

Med Report Deutschland, "Sorafenib zur Therapie des fortgeschrittenen Nierenzellkarzinoms zugelassen," (2006), 1 page English translation.

Michaelis, "Phenylharnstoff des 1-Phenyl-3-methyl-5-aminopyrazols."Justus Liebigs Ann. Chem. (JLACBF) 397, 1913, p. 143 English translation.

Peters, H.D., "Sorafenib bei soliden Tumoren," Focus Onkologie, 2007, Auflage 12000, 6 pages English translation.

Strumberg et al., "Sorafenib Neue Therapieoption in der Onkologie," Krankenhauspharmazie, 2007, vol. 28, pp. 93-97, pp. 1/5, 2/5, 3/5, and 4/5 Enligh translation.

Stollorz, "Die Krebsformel, die der Zufall fand," Frankfurter Allgemeine Sonntagszeitung, Jul. 2, 2006, NR 26, pp. 68-69 English translation.

Adjei et al., "A Phase I study of BAY 43-9006 and getitinib in patients with refractory or recurrent non-small-cell lung cancer (NSCLC)," Abstract #3067, Meeting: 2005 ASCO Annual Meeting, Category: Developmental Therapeutics: Molecular Therapeutics, Subcategory: Antiangiogenic or Antimetastatic agents.

Ahmad et al., "Kinase Inhibition with BAY 43-9006 in Renal Cell Carcinoma," Clinical Cancer Research, Sep. 15, 2004, vol. 10(suppl.), pp. 6388s-6392s.

Amornphimoltham et al., "Persistent Activation of the Akt Pathway in Head and Neck Squamous Cell Carcinoma: A Potential Target for UCN-01," Clinical Cancer Research, vol. 10, Jun. 15, 2004, pp. 4029-4037.

Arzneimitteltherapie, "Sorafenib" Oct. 6, 2006, Auflage 18498, 7 pages.

Arnone et al., "Selectivities in the Oxidation of Tertiary Amines and Pyridine Derivatives by Perfluoro Cis-2.3-dialkyloxaziridines," Tetrahedron, vol. 54, 1998, pp. 7831-7842.

Arora et al., "Stromelysin 3, Ets-1, and Vascular Endothelial Growth Factor Expression in Oral Precancerous and Cancerous Lesions: Correlation with Microvessel Density, Progression, and Prognosis," Clinical Cancer Research, 11: 2272-2284 (Mar. 15, 2005).

Ascierto et al., "Pronostic Value of Serum VEGF in Melanoma Patients: a Pilot Study" Anticancer Research, 24: 4255-4258 (2004).

Auclair et al., "BAY 43-9006 (Sorafenib) is a potent inhibitor of FLT3 tyrosine kinase signaling and proliferation in AML cells," Abstract #5991, 96$^{th}$ Annual Meeting, Anaheim/Orange County, CA, Apr. 16-20, 2005.

Audia et al., "Potent, Selective Tetrahydro-β-carboline Antagonists of the Serotonin 2B (5HT$_{2B}$) Contractile Receptor in the Rat Stomach Fundas," J. Med. Chem. 1996, 39, pp. 2773-2780.

Avruch et al., "Raf meets Ras: completing the framework of a signal transduction pathway," TIBS 19; Jul. 1994; pp. 279-283.

Audia et al., "Potent, Selective Tetrahydro-β- carboline Antagonists of the Serotonin 2B (5HT$_{2B}$) Contractile Receptor in the Rat Stomach Fundas," J. Med. Chem. 1996, 39, pp. 2773-2780.

Awada et al., "Phase I safety and pharmacokinetics of BAY 43-9006 administered for 21 days on/7 days off in patients with advanced, refractory solid tumours" British Journal of Cancer 92, pp. 1855-1861 (2005).

Bachelot et al., "Prognostic value of serum levels of interleukin 6 and of serum and plasma levels of vascular endothelial growth factor in hormone-refractory metastatic breast cancer patients," British Journal of Cancer, 88: 1721-1726 (2003).

Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," JPET 279: pp. 1453-1461 (1996).

Baka et al., "A review of the latest clinical compounds to inhibit VEGF in pathological angiogenesis," Expert Opinion Therapeutic Targets, 2006, vol. 10, No. 6, pp. 867-876.

Balant et al., "Metabolic Considerations in Prodrug Design," Chapter Twenty-Three In: Burger's Medicinal Chemistry and Drug Discovery, 5$^{th}$ ed. John Wiley & Sons, Inc., New York, 1995: vol. 1,pp. 949-982.

Bando et al., "Association between intratumoral free and total VEGF, soluble VEGFR-1, VEGFR-2 and prognosis in breast cancer" British Journal of Cancer, 2005, vol. 92, pp. 553-561.

Banerjee et al., "Murine Coronavirus Replication-Induced p38 Mitogen-Activated Protein Kinase Activation Promotes Interleukin-6 Production and Virus Replication in Cultured Cells," Journal of Virology. American Society for Microbiology, 2002: vol. 76, pp. 5937-5948.

Bankston et al., "A Scaleable Synthesis of BAY 43-9006: A Potent Raf Kinase Inhibitor for the Treatment of Cancer," Organic Process Research & Development, 2002, vol. 6, pp. 777-781.

Barnett et al., "Identification and characterization of pleckstrin-homology-domain-dependent and isoenzyme-specific Akt inhibitors," Biochem J., vol. 385, 2005, pp. 399-408.

Baumann et al., "Raf induces NF-κB by membrane shuttle kinase MEKK1, a signaling pathway critical for transformation," Proc. Natl. Acad. Sci. USA, vol. 97: No. 9: 4615-4620 (Apr. 25, 2000).

Bayer Corporation et al., "Trial of BAY 43-9006 in Patients with Relapsed or Refractory Advanced Non-Small Cell Lung Carcinoma", NCT0010413, clinicaltrials.gov, 3 pages.

(56) References Cited

OTHER PUBLICATIONS

Bellacosa et al., "Molecular Alterations of the AKT2 Oncogene in Ovarian and Breast: Carcinomas," Int. J. Cancer (Pred. Oncol.), vol. 64, 1995, pp. 280-285.

Berge et al., "Pharmaceutical Salts." Journal of Pharmaceutical Sciences. Jan. 1977:1-19, vol. 66, No. 1.

Bergstralh et al., "Microtubule stabilizing agents: Their molecular signaling consequences and the potential for enhancement by drug combination," *Cancer Treatment Reviews*, 2006, vol. 32, pp. 166-179.

Bertrand et al., "Inhibition of PI3K, mTOR and MEK signaling pathways promotes rapid apoptosis in B-Lineage ALL in the presence of stromal cell support", Leukemia, vol. 19, pp. 98-102 (published online Oct. 21, 2004).

Bhagwat et al., "The angiogenic regulator CD13/APN is a transcriptional target of Ras signaling pathways in endothelial morphogenesis," Blood, vol. 101, No. 5, pp. 1818-1826, (Mar. 1, 2003).

Bianchi et al., "A Phase II multi-center uncontrolled trial of sorafenib (BAY 43-9006) in patients with metastatic breast cancer" Journal of Clinical Oncology, Draft 33 pages (presented previously Oct. 30-Nov. 3, 2005).

Martín-Blanco, "p38 MAPK signalling cascades: ancient roles and new functions," BioEssays, 22:637-645, 2000.

Foussard-Blanpin, Odette, "Comparative pharmacological study of substituted carboxamides upon central nervous system," Ann. Pharm. Fr. (1982), 40 (4), pp. 339-350.

Board et al., "Platelet-derived growth factor receptor (PDGFR): A target for anticancer therapeutics," Drug Resistance Updates 8 (2005) 75-83.

Bok et al., "Vascular Endothelial Growth Factor and Basic Fibroblast Growth Factor Urine Levels as Predictors of Outcome in Hormone-refractory Prostate Cancer Patients: A Cancer and Leukemia Group B Study." Cancer Research, 61: 2533-2536 (Mar. 15, 2001).

Bollag et al., "Raf pathway inhibitors in oncology," Current Opinion in Investigational Drugs (2003) 4(12): pp. 1436-1441.

Bolton et al., "Chapter 17, *Ras* Oncogene Directed Approaches in Cancer Chemotherapy," Annual Reports in Medicinal Chemistry, vol. 29, 1994, pp. 165-174.

Bono et al., "Serum KIT and KIT ligand levels in patients with gastrointestinal stromal tumors treated with imatinib," Blood 103:2929-2935 (2004).

Bos, J.L. "*ras* Oncogenes in Human Cancer: A Review," *Cancer Research*, vol. 49, Sep. 1, 1989, pp. 4682-4689.

Boulton et al., "Heterocyclic Rearrangements. Part X. A Generalised Monocyclic Rearrangement," J. Chem. Soc. (C), 1967, pp. 2005-2007.

Boyer, S.J., "Small Molecule inhibitors of KDR (VEGFR-2) Kinase: An Overview of Structure Activity Relationships," Current Topics in Medicinal Chemistry, 2002, vol. 2, pp. 973-1000.

Boyd, et al. "Arene Oxides of Quinoline: Epoxidation, *N*-Oxidation and *N*-Methylation Reactions," J. Chem. Soc. Perkin Trans. 1, 1991: pp. 2189-2192.

Braybrooke et al., "A Phase II Study of Razoxane, an Antiangiogenic Topoisomerase II Inhibitor, in Renal Cell Cancer with Assessment of Potential Surrogate Markers of Angiogenesis," Clin. Canc. Res. 6:4697-4704 (2000).

Broll et al., "Vascular endothelial growth factor (VEGF)—a valuable serum tumour marker in patients with colorectal cancer?" Eur. J. Surg. Oncol. 27:37-42 (2001).

Bruder et al., "Adenovirus Infection Stimulates the Raf/MAPK Signaling Pathway and Induces Interleukin-8 Expression" Journal of Virology. Vol, 71, pp. 398-404, 1997.

Bundgaard, Hans. "Design of prodrugs: Bioreversible derivatives for various functional groups and chemical entities." pp. 1-92, in Design of Prodrugs, Elsevier Science Publishers B.V., Amsterdam, The Netherlands, 1985.

Campbell et al., "Increasing complexity of Ras signaling," Oncogene, 1998, vol. 17, pp. 1395-1413.

Cancer Weekly, "Antisense Technology (Clinical Trial). Phase II Trial of Second Antisense Cancer Drug Begins," Cancer Weekly, p. 4 (Dec. 8, 1997).

Canetta et al., "Carboplatin: current status and future prospects," Cancer Treatment Reviews, 1998, pp. 17-32, vol. 15(Supplement B).

Caponigro et al., "Epidermal growth factor receptor as a major anticancer drug target," Exp. Opin. Thera. Targets, 2006, vol. 10, No. 6, pp. 877-888.

Carey et al., "Contents of Part A," pp. vii-xi and "Contents of Part B," pp. xiii-xviii, in Advanced Organic Chemistry, Second Edition, Part A: Structure and Mechanisms, Plenum Press, NY (1984).

Carling et al., "1-(3-Cyanobenzylpiperidin-4-yl)-5-methyl-4-phenyl-1,3-dihydroimidazol-2-one: A Selective High Affinity Antagonist for the Human Dopamine $D_4$ Receptor with Excellent Selectivity over Ion Channels," J. Med. Chem., 1999, 42, pp. 2706-2715.

Carlomagno et al., "BAY 43-9006 Inhibition of Oncogenic RET Mutants," Journal of the National Cancer Institute, 2006, vol. 98, No. 5, pp. 326-334.

Carney et al., "Monitoring the Circulating Levels of the HER2/*neu* Oncoprotein in Breast Cancer," Clin Breast Cancer 5(2): 105-116, (2004).

Carter et al., "Anti-Tumor Efficacy of the Orally Active *Raf* Kinase Inhibitor BAY 43-9006 in Human Tumor Xenograft Models," Proceedings of the American Association for Cancer Res., vol. 42: p. 923, Mar. 2001, Abstract #4954.

Carter et al., "Drug-Tumor Interactions" pp. 362-365, in: Chemotherapy of Cancer, Second Edition, John Wiley & Sons, NY (1981).

Carter et al., "Sorafenib is efficacious and tolerated in combination with cytotoxic or cytostatic agents in preclinical models of human non-small cell lung carcinoma," Cancer Chemotherapy and Pharmacology, Springer Berlin/Heidelberg, vol. 59, No. 2, pp. 183-195 (Feb. 2007). Abstract.

Chang et al., "BAY 43-9006 (Sorafenib) inhibits ectopic (s.c.) and orthotopic growth of a murine model of renal adenocarcinoma (Renca) predominantly through inhibition of tumor angiogenesis," $96^{th}$ Annual Meeting, Anaheim/Orange County, CA, Apr. 16-20, 2005, 1 page.

Chang et al., "Sorafenib (BAY 43-9006) inhibits tumor growth and vascularization and induces tumor apoptosis and hypoxia in RCC xenograft models," Cancer Chemother. Pharmacol., 2007, vol. 59, pp. 561-574.

Chen et al., "Role of Regulatory Elements and the MAPK/ERK OR p38 MAPK Pathways for Activation of Human Cytomegalovirus Gene Expression," Journal of Virology, 2002: vol. 76, No. 10, pp. 4873-4885.

Chen et al., "Suppression of Japanese encephalitis virus infection by non-steroidial, anti-inflammatory drugs," Journal of General Virology, 2002, vol. 83, pp. 1897-1905.

Chen et al., "Expression of Proinflammatory and Proangiogenic Cytokines in Patients with Head and Neck Cancer," Clinical Cancer Research 5:1369-1379 (Jun. 1999).

Chialda et al., "Inhibitors of mitogen-activated protein kinases differentially regulate costimulated T cell cytokine production and mouse airway eosinophilia," Respiratory Research 2005, 6:36, pp. 1-19.

Chin et al., "Vascular endothelial growth factor and soluble Tie-2 receptor in colorectal cancer: associations with disease recurrence," European Journal of Surgical Oncology, 29:497-505 (2003).

Choi et al., "Imatinib-Resistant Cell Lines Are Sensitive to the Raf Inhibitor BAY 43-9006," Blood, W.E.B. Saunders Company, Orlando, FL, US, vol. 100, No. 11, Abstract # 1427 (Dec. 10, 2002).

Choong et al., "Forthcoming receptor tyrosine kinase inhibitors," Exp. Opin. Ther. Targets, 2006, vol. 10, No. 6, pp. 793-797.

Chow et al., "Measurement of MAP Kinase Activation by Flow Cytometry Using Phospho-Specitic Antibodies to MEK and ERK: Potential for Pharmacodynamic Monitoring of Signal Transduction Inhibitors," Cytometry (Communications in Clinical Cytometry) 46:72-78 (2001).

Christensen, et al., "Plasma vascular endothelial growth factor and interleukin-8 as biomarkers of antitumor efficacy of a prototypical erbB family tyrosine kinase inhibitor," Mol. Cancer Ther., 4(6):938-947 (Jun. 2005).

(56) References Cited

OTHER PUBLICATIONS

Chu et al., "Cardiotoxicity associated with tyrosine kinase inhibitor sunitinib," Lancet, 2007, vol. 370, pp. 2011-2019.
Chustecka et al., "Bortezonnib and Sorafenib Show Activity in Thyroid Cancer," Medscape, 2 pages (Nov. 2, 2006).
Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1, 2005, vol. 11, No. 15, pp. 5472-5480.
Garbe, "Auch ein Therapieplatz für Sorafenib?" Medical Special (2006) 2 pages.
Copéret et al., "A Simple and Efficient Method for the Preparation of Pyridine-N-oxides II," Tetrahedron Letters, Elsevier Science Ltd., Pergamon Press, Oxford, UK 1998: vol. 39, pp. 761-764.
Cortes et al., "Targeting the Microtubules in Breast Cancer Beyond Taxanes: The Epothilones," *The Oncologist*, 2007, vol. 12, pp. 271-280.
Craig, "The mechanisms of drug release from solid dispersions in water-soluble polymers." International Journal of Pharmaceutics 231 (2002) 131-144, Elsevier Science B.V.
Le Cras et al., "Treatment of newborn rats with a VEGF receptor inhibitor causes pulmonary hypertension and abnormal lung structure." Am. J. Physiol. Lung. Cell. Mol. Physiol. vol. 283, pp. L555-L562, 2002.
Crump, Micheal, "Inhibition of raf kinase in the treatment of acute myeloid leukemia," Medline Abstract ISSN:1381-6128, Current Pharmaceutical Design, vol. 8, Issue 25, 2002, pp. 2243-2248.
Cunningham et al., "A Phase I Trial of H-*ras* Antisense Oligonucleotide ISIS 2503 Administered as a Continuous Intravenous Infusion in Patients with Advanced Carcinoma," Cancer, 2001, American Cancer Society, vol. 92, No. 5, pp. 1265-1271.
Danson et al., "Improving Outcomes in Advanced Malignant Melanoma. Update on Systemic Therapy," *Drugs*, 2005, vol. 65, No. 6, pp. 733-743.
Dasmahapatra et al., "In vitro Combination Treatment with Perifosine and UCN-01 Demonstrates Synergism against Prostate (PC-3) and Lung (A549) Epithelial Adenocarcinoma Cell Lines," Clinical Cancer Research, vol. 10, Aug. 1, 2004, pp. 5242-5252.
Daum et al., "The ins and outs of Raf kinases," TIBS 19, Nov. 1994, pp. 474-480.
Dayan et al., "Tertiary Amine Oxidation using HOF•CH$_3$CN: A Novel Synthesis of *N*-Oxides," Synthesis, 1999, No. SI, pp. 1427-1430.
DeGrendele, "Activity of the Raf Kinase Inhibitor BAY 43-9006 in Patients with Advancer Solid Tumors," Clinical Colorectal Cancer, May 2003, vol. 3, pp. 16-18.
Dehtling, J. "Große Onkologie-Pipeline" Medizinische Monatsschrift für Pharmazeuten, 2006, Auflage 12914, 2 pages.
Denny, "Prodrug strategies in cancer therapy," European Journal of Medicinal Chemistry. 2001: vol. 36, pp. 577-595.
DeVita et al., "Elevated Perioperative Serum Vascular Endothelial Growth Factor Levels in Patients with Colon Carcinoma," Cancer, 100 (2) pp. 270-278 (2004).
Devlin et al., "GATT and DISCOVERY: Significant Changes in U.S. Patent Law" Screening Forum, vol. 3, No. 4, pp. 1, 3 and 6 (Dec. 1995).
Doanes et al., "VEGF Stimulates MAPK through a Pathway That is Unique for Receptor Tyrosine Kinases," Biochem Biophys. Res. Commun. 255: pp. 545-548, 1999.
Dörwald, "Preface," p. IX, in Side Reactions in Organic Synthesis: A Guide to Successful Synthesis Design, Wiley-VCH Verlag GmbH & Co. KGaA (2005).
Downward, J. "Mechanisms and consequence of activation of protein kinase B/Akt," Current Opinion in Cell Biology, vol. 10, 1998, pp. 262-267.
Drevs et al., "Soluble markers for the assessment of biological activity with PTK787/ZK 222584 (PTK/ZK), a vascular endothelial growth factor receptor (VEGFR) tyrosine kinase inhibitor in patients with advanced colorectal cancer from two phase I trials," Annals of Oncology, 16: 558-565 (2005).

Drevs, J., "Soluble Markers for the Detection of Hypoxia under Antiangiogenic Treatment," Anticancer Research, 23: 1159-1162 (2003).
Drevs, J., Die Medizinische Welt, 2006, pp. 3/5, 4/5, 5/5.
"Doxorubicin HC1 (ADR)," in drugs: facts and comparisons, 1994 Ed., pp. 2703-2705.
Dudek et al., "Circulating Angiogenic Cytokines in Patients with Advanced Non-Small Cell Lung Cancer: Correlation with Treatment Response and Survival," Cancer Investigation, 23: 193-200 (2005).
Dumas, J. "Protein kinase inhibitors from the urea class," Curr. Opin. in Drug Discovery and Dev., 5(s):718-727, 2002.
Dumas et al., "Discovery of a New Class of p38 Kinase Inhibitors," Bioorganic & Medicinal Chemistry Letters vol. 10, (2000), pp. 2047-2050.
Dumas et al., "1-Phenyl-5-pyrazolyl Ureas: Potent and Selective p38 Kinase Inhibitors," Bioorganic & Medicinal Chemistry Letters, 2000, vol. 10, pp. 2051-2054.
Dumas, J., "Growth factor receptor kinase inhibitors: Recent progress and clinical impact," Current Opinion in Drug Discovery & Development, 2001, vol. 4, No. 4, pp. 378-389.
Dumas, J., "Protein kinase inhibitors: emerging pharmacophores 1997-2000," Expert Opinion on Therapeutic Patents (2001) vol. 11, No. 3, pp. 405-429.
Dumas et al., "Orally Active p38 Kinase Inhibitors from the Urea Class," Poster, 222nd American Cancer Society National Meeting 2001, Med I 256, 1 page.
Dumas, J., "Raf Kitnase Inhibitors," Expert Opinion on Therapeutic Patients, vol. 8, No. 12, pp. 1749-1750, 1998.
Dumas et al., "Recent developments in the discovery of protein kinase inhibitors from the urea class," *Current Opinion in Drug Discovery & Development*, 2004, vol. 7, No. 5, pp. 610-616.
Dumas et al., "Synthesis and Pharmacological Characterization of a Potent, Orally Active p38 Kinase Inhibitor," *Bioorganic & Medicinal Chemistry Letters*, 2002, vol. 12. pp. 1559-1562.
Dunst et al., "Tumor Hypoxia and Systemic Levels of Vascular Endothelial Growth Factor (VEGF) in Head and Neck Cancers," Strahlentherapie und Onkologie, 177(9): 469-473 (2001).
Ebos et al., "Multiple circulating proangiogenic factors induced by sunitinib malate are tumor-independent and correlated with antitumor efficacy" PNAS vol. 104, No. 43, pp. 17069-17074 (Oct. 23, 2007).
Ebrahimi et al., "Cytokines in Pancreatic Carcinoma. Correlation with Phenotypic Characteristics and Prognosis," Cancer, 101(12): 2727-2736 (Published on-line Nov. 3, 2004).
Eisen et al., "Phase I trial of BAY 43-9006 (Sorafenib) combined with dacarbazine (DTIC) in metastatic melanoma patients," Abstract #7508, Meeting: *2005 ASCO Annual Meeting*, Category: Melamona, Subcategory: Melamona.
Eisen et al., "Sorafenib in advanced melanoma: a Phase II randomised discontinuation trial analysis" British Journal of Cancer 95, 581-586 (2006).
Eisenhauer et al., "Impact of new non-cytotoxics in the treatment in ovarian cancer." International J. Gynecol. Cancer, 2001, vol. 11, Supplement 1, pp. 68-72.
El-Deiry, Wafik S., "Meeting Report: The International Conference on Tumor Progression and Therapeutic Resistance", Cancer Research, 2005; vol. 65, No. 11, pp. 4475-4484.
Elting, et al., "Biomarkers associated with clinical outcomes in TARGETs, a Phase III single-agent, placebo-controlled study of sorafenib in advanced renal cell carcinoma," Proc. Amer. Assoc. Cancer Res. vol. 47, Abstract # 2909, 2006, pp. 683-684.
Escudier et al., "Randomized Phase III trial of the Raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer, 1 page.
Escudier et al., "Sorafenib in Advanced Clear-Cell Renal-Cell Carcinoma" New England Journal of Medicine vol. 356: 125-134 (Jan. 11, 2007).
European Medicines Agency, "CHMP Assessment Report for Nexavar" Doc Ref: EMEA/CHMP/140610/2006, 63 pages.

(56) References Cited

OTHER PUBLICATIONS

Fabian et al., "A small molecule kinase interaction map for clinical kinase inhibitors," Nature Biotechnology, 2005, vol. 23, No. 3, pp. 329-336, 4 supplementary pages.

Faderl et al., "Angiogenic factors may have a different prognostic role in adult acute lymphoblastic leukemia," Blood, 2005 vol. 106 No. 13, pp. 4303-4307.

Faivre et al., "Molecular basis for sunitinib efficacy and future clinical development" Nature Reviews Drug Discovery, Nature Publishing Group, pp. 734-745, vol. 6 (Sep. 2007).

Fakhari et al., "Upregulation of Vascular Endothelial Growth Factor Receptors is Associated with Advanced Neuroblastoma," Journal of Pediatric Surgery, 37(4): 582-587 (Apr. 2002).

Favaro et al., "Targeted therapy in renal cell carcinoma," Expert Opin. Investig. Drugs 14(10):1251-1258 (2005).

Fiedler et al. "A phase 2 clinical study of SU5416 in patients with refractory acute myeloid leukemia," Blood, 102(8): 2763-2767(prepublished online Jul. 3, 2003).

Feldmann, "Pathogenesis of arthritis: recent research progress," Nature Immunology 2001, vol. 2, No. 9, pp. 771-773.

Fields Virology Second Editors, "Contents,": vol. 1, pp. ix-xiv, Raven Press, NY (1990).

Flaherty et al., "A Phase I Trial of the Oral, Multikinase Inhibitor Sorafenib in Combination with Carboplatin and Paclitaxel" Clin Cancer Res 41(15):4836-4842 (Aug. 1, 2008).

Flaherty et al., "Phase I/II trial of Bay 43-9006 carboplatin (C) and paclitaxel (P) demonstrates preliminary antitumor activity in the expansion cohort of patients with metastatic melanoma." Journal of Clinical Oncology, 2004 ASCO annual meeting proceedings, vol. 22, No. 14S (2004) Supplement: 7507, 4 pages.

Flaherty et al., "Antisense therapeutics: lessons from early clinical trials," Current Opin. in Oncol. 13: 499-505 (2001).

Foekens et al., "High Tumor Levels of Vascular Endothelial Growth Factor Predict Poor Response to Systemic Therapy in Advanced Breast Cancer." Cancer Research, 2001, vol. 61. pp. 5407-5414.

Forbes et al., "$N$-(1-Methyl-5-indolyl)-$N'$-(3-methyl-5-isothiazolyl)urea: A Novel, High-Affinity 5-$HT_{2B}$ Receptor Antagonist," Journal of Medicinal Chemistry, 1995, vol. 38, No. 6, pp. 855-857.

Franco et al., "Dissolution properties and anticonvulsant activity of phenytoin-polyethylene glycol 6000 and -polyvinylpyrrolidone K-30 solid dispersions," International journal of Pharmaceutics 225 (2001) pp. 63-73.

Fridman et al., "The Minimal Fragments of c-Raf-1 and NF1 That Can Suppress v-Ha-Ras-Induced Malignant Phenotype," The Journal of Biological Chemistry, vol. 269, No. 48, 1994, pp. 30105-30108.

Garcia-Lòpez et al., "New Routes for the Synthesis of Pyrrolo[3,2-$d$]- and [2,3-$d$]-pyrimidine Systems starting from a Common Pyrrole Derivative," Journal of the Chemical Society, Perkin Transactions 1: Organic and Bio-Organic Chemistry (1972-1999), 1978, pp. 483-487.

Gatzemeier et al., "Phase II trial of single-agent sorafenib in patients with advanced non-small cell lung carcinoma," Journal of Clinical Oncology, 2006 ASCO Annual Meeting Proceedings Part I, vol. 24, No. 18S (Jun. 20 Supplement) 2006, abstract No. 7002, 4 pages.

Geiger et al., "Antitumor Activity of a C-raf Antisense Oligonucleotide in Combination with Standard Chemotherapeutic Agents against Various Human Tumors Transplanted Subcutaneously into Nude Mice," Clinical Cancer Research vol. 3, 1179-1185, Jul. 1997.

Geng et al., "A Specific Antagonist of the p110δ Catalytic Component of Phosphatidylinositol 3'-Kinase, IC486068, Enhances Radiation-Induced Tumor Vascular Destruction," Cancer Research, 64, Jul. 2004, pp, 4893-4899.

Gennaro, Alfonso R. "Table of Contents," pp. xiv-xv, in Remington: The Science and Practice of Pharmacy. 20th Ed. Remington. Lippincott Williams & Wilkins, 2000.

George et al., "VEGF-A, VEGF-C and VEGF-D in Colorectal Cancer Progression," Neoplasia, 3(5): 420-427 (2001).

George et al., "Prognostic Significance of Plasma Vascular Endothelial Growth Factor Levels in Patients with Hormone-refractory Prostate Cancer Treated on Cancer and Leukemia Group B 9480," Clinical Cancer Research, 7: 1932-1936 (Jul. 2001).

Abou-Alfa et al., "Phase II Study of Sorafenib in Patients with Advanced Hepatocellular Carcinoma" Journal of Clinical Oncology, vol. 24, No. 26, pp. 4293-4300 (Sep. 10, 2006).

Giambartolomei et al., "Sustained activation of the Raf/MEK/Erk pathway in response to EGF in stable cell lines expressing the Hepatitis C Virus (HCV) core protein," Oncogene, Nature Publishing Group, 2001: vol. 20, pp. 2606-2610.

Gills et al., "The development of phosphatidylinositol ether lipid analogues as inhibitors of the serine/threonine kinase, Akt," Expert Opin. Investig. Drugs, vol. 13, No. 7, 2004, pp. 787-797.

Gollob, "Sorafenib: scientific rationales for single-agent and combination therapy in clear-cell renal cell carcinoma" Pub Med PMID: 16425993, Clin. Genitourin. Cancer 4(3):167-174 (2005) abstract.

Gómez-Esquer et al., "mRNA expression of the angiogenesis markers VEGF and CD105 (endoglin) in human breast cancer," Anticancer Res., 2004, vol. 24, No. 3a, pp. 1581-1585, XP-002455577, abstract.

Grant et al., "Some Hypotensive Thiadiazoles," J. Med. Chem. (1972), 15(10), pp. 1082-1084.

Greene et al., "Contents," pp. xi-xii, in: Protective Groups in Organic Synthesis, 3rd Ed. John Wiley & Sons, Inc., New York, 1999.

Gelasser, "The Importance of Solvates," in: Polymorphism in the Pharmaceutical Industry, Chapter 8, p. 211, 2006, Wiley-VCH Verlug GmbH & Co., KGaA, Weinhelm.

Gridelli et al., "Sorafenib and Sunitinib in the Treatment of Advanced Non-Small Cell Lung Caner" The Oncologist (2007) 12:191-200.

Guan et al., "H5N1 influenza: A protean pandemic threat," Proc. Natl. Acad. Sci. USA, May 25, 2004; vol. 101, pp. 8156-8161.

Gupta et al., "Sorafenib targets BRAF and VEGFR in metastatic thyroid carcinoma" Journal of Clinical Oncology, 2007 ASCO Annual Meeting Proceedings (Post-Meeting Edition) vol. 25, No. 18S (Jun. 20 Supplement), 2007: 6019 abstract.

Gura, "Systems for identifying new drugs are often faulty." Science, 1997, vol. 278, (5340), pp. 1041-1042, MEDLINE with Full text.

Hahn et al., "Sorafenib," Curr. Opin. Oncol. 18:615-621 (2006).

Hall-Jackson et al., "Paradoxical activation of Raf by a novel Raf inhibitor," Chemistry & Biology, 6: 559-568 (Jul. 1999).

Han et al., "Targeted Prodrug Design to Optimize Drug Delivery." AAPS Pharmsci. 2000: vol. 2, No. 1, Article 6, 1-11.

Hanna, "Second-Line Treatment of Non-small Cell Lung Cancer: Big Targets, Small Progress; Small Targets, Big Progress?" Journal of Thoracic Oncology vol. 1, No. 9, pp. 927-928 (Nov. 2006).

Hansch et al., "Contents," 21 pages, in: Comprehensive Medicinal Chemistry. The Rational Design, Mechanistic Study & Therapeutic Application of Chemical Compounds, Pergamon Press, Oxford, Uk, 1990.

Hanson, "Pulmonary-Allergy, Dermatological, Gastrointestinal & Arthritis, Inhibitors of p38 kinase," Exp. Opin. Ther. Patents, 1997, vol. 7, No. 7, pp. 729-733.

Hardmann et al., excerpts from chapter 3. Principles of Therapeutics, in: Goodman & Gilman's The Pharmacological Basis of Therapeutics, 9th ed., 1996, pp. 51 and 57-58.

Harris et al., "Soluble Tie2 and Flt1 Extracellular Domains in Serum of Patients with Renal Cancer and Response to Antiangiogenic Therapy," Clin. Cancer Res. 7:1992-1997 (2001).

Hayes et al., "Serum vascular endothelial growth factor as a tumour marker in soft tissue sarcoma," British Journal of Surgery, 91:242-247 (Published on-line Nov. 24, 2003).

Hegedus, L.S. "Contents," 4 pages in: Transition Metals in the Synthesis of Complex Organic Molecules, University Science Books, Mill Valley, California, 1994.

Heim et al., "Antitumor effect and potentiation or reduction in cytotoxic drug activity in human colon carcinoma cells by the Raf kinase inhibitor (RKI) BAY 43-9006," International Journal of Clinical Pharmacology and Therapeutics, 2003, vol. 41, No. 12, pp. 616-617.

Heim et al., "The Raf kinase inhibitor BAY 43-9006 reduces cellular uptake of platinum compounds and cytotoxity in human colorectal carcinoma cell lines," Anti-Cancer Drugs, 2005, vol. 16, pp. 129-136.

(56) References Cited

OTHER PUBLICATIONS

Herlaar et al., "p38 MAPK signalling cascades in inflammatory disease," Molecular Medicine Today, vol. 5, pp. 439-447 (Oct. 1999).
Herrera et al., "Unraveling the complexities of the Raf/MAP kinase pathway for pharmacological intervention," Trends in Molecular Medicine, 2002, vol. 8, No. 4 (Suppl.), pp. S27-S31.
Higuchi T. et al., "Contents," in: Prodrugs as Novel Drug Delivery Systems, ACS Symposium Series 14, American Chemical Society, Washington, DC, 1975, p. vii.
Higuchi et al., "Mitochondrial DNA determines androgen dependence in prostate cancer cell lines," Oncogene, 2006, vol. 25, pp. 1437-1445.
Hilger et al., "Correlation of ERK-phosphorylation and toxicities in patients treated with the Raf kinase inhibitor BAY 43-9006" international Journal of Clinical Pharmacology and Therapeutics, vol. 42, No. 11, pp. 648-649 (2004).
Hilger et al., "ERK1/2 phosphorylation: a biomarker analysis within a phase I study with the new Raf kinase inhibitor Bay 43-9006" International Journal of Clinical Pharmacology and Therapeutics, vol. 40, No. 12, pp. 507-568 (2002).
Hilger et al., "Inhibition of ERK phosphorylation and clinical outcome in patients treated with the Raf kinase inhibitor BAY 43-9006" Proc Am Soc Clin Oncol 21: 2002 (abstr 1916), 3 pages.
Hirasawa et al., "Effect of p38 Mitogen-Activated Protein Kinase on the Replication of Encephalomyocarditis Virus." Journal of Virology, May 2003: vol. 77, No. 10, pp. 5649-5656.
Holmlund et al., "Phase I Trial of C-raf Antisense Oligonucleotide ISIS 5132 (CGP 69846A) By 21-Day Continuous Intravenous Infusion (CIV) In Patients With Advanced Cancer," (Meeting abstract), 1998 ASCO Annual Meeting, Abstract No. 811, 2 pages.
Hotte et al., "Bay 43-9006: Early clinical data in patients with advanced solid malignancies," Current Pharmaceutical Design, 8: 2249-2253, 2002.
Hu et al., "Soluble Vascular Endothelial Growth Factor Receptor 1, and Not Receptor 2, is an Independent Prognostic Factor in Acute Myeloid Leukemia and Myelodyslastic Syndromes," Cancer, 100(9): 1884-1891 (Published on-line Mar. 29, 2004).
Hubbard, "Oncogenic Mutations in B-Raf: Some Losses Yield Gains," Cell vol. 116, Issue 6, 764-766 (2004).
Hyodo et al., "Clinical Significance of Plasma Vascular Endothelial Growth Factor in Gastrointestinal Cancer," European Journal of Cancer, 34(13): 2041-2045 (1998).
Ihle et al., "Molecular pharmacology and antitumor activity of PX-866, a novel inhibitor of phosphoinositide-3-kinase signaling," Molecular Cancer Therapy, vol. 3, No. 7, 2004, pp. 763-772.
Ishigami et al., "Predictive value of vascular endothelial growth factor (VEGF) in metastasis and prognosis of human colorectal cancer," British Journal of Cancer, 78(10): 1379-1384 (1998).
Jacobsen et al., "Vascular Endothelial Growth Factor as Prognostic Factor in Renal Cell Carcinoma," Journal of Urology, 163(1): 343-347 (Jan. 2000).
Jacobsen et al., "Prognostic importance of serum vascular endothelial growth factor in relation to platelet and leukocyte counts in human renal cell carcinoma," European Journal of Cancer Prevention, 2002, 11(3) pp. 245-252.
Jain et al., "Randomized Discontinuation Trial of Sorafenib (BAY 43-9006)," Caner Biology & Therapy, vol. 5, issue 10, pp. 1270-1272 (2006).
Jeffcoat et al., "The Metabolism and Toxicity of Halogenated Carbanilide," Drug Metabolism and Disposition, vol. 5, No. 2, pp. 157-166 (1977).
Jimeno et al., "Analysis of Biologic Surrogate Markers from a Children's Oncology Group Phase I Trial of Gefitinib in Pediatric Patients with Solid Tumors," Pediatr. Blood Cancer, 49(3): 352-357 (2007).
Jin et al., "Inhibition of AKT survival pathway by a small molecule inhibitor in human endometrial cancer cells," British Journal Of Cancer, vol. 91, 2004, pp. 1808-1812.
Johnson et al., "Relationships between drug activity in NCI preclinical in vitro and in vivo models and early clinical trials," British Journal of Cancer, 2001, vol. 84, No. 10, pp. 1424-1431.
Johnston, D, et al., "Elevation of the Epidermal Growth Factor Receptor and Dependent Signaling in Human Papillomavirus-infected Laryngeal Papillomas." Cancer Research, 1999: vol. 59, pp. 968-974.
Jungmayr, P., "Aktueller Stand der Krebstherapie," Deutsche Apotheker Zeitung, Sep. 30, 2004, Auflage ca. 36.000.
Kapoun et al., "TGEβR1 kinase activity, but not p38 activation is required for TGFβR1-induced myofibroblast differentiation and profibrotic gene expression," Molecular Pharmacology Fast Forward, abstract, 2006, www.molpharmaspetjournals.org, 2 pages.
Karayiannakis et al., "Circulating VEGF Levels in the Serum of Gastric Cancer Patients," Annals of Surgery, 236(1):37-42 (Jul. 2002).
Karayiannakis et al., "Clinical significance of preoperative serum vascular endothelial growth factor levels in patients with colorectal cancer and the effect of tumor surgery," 131(5): 548-555 (May 2002).
Karp et al., "Targeting Vascular Endothelial Growth Factor for Relapsed and Refractory Adult Acute Myelogenous Leukemias: Therapy with Sequential 1-β-D Arabinofuranosylcytosine, Mitoxantrone, and Bevacizumab," Clinical Cancer Research, 10: 3577-3585 (Jun. 1, 2004).
Katritzky et al., "1.18. Azetidines, Azetines, and Azetes: Monocylcic" pp. 507-508 in: Comprehensive Heterocyclic Chemistry II, A Review of the Literature 1982-1995: The Structure, Reactions, Synthesis, and Uses of Heterocyclic Compounds. Pergamon Press, Oxford, UK, 1996.
Katritzky, Alan R., Tables of Content, in: Comprehensive Organic Functional Group Transformations. Pergamon Press, Oxford, UK, 1995, 25 pages.
Katritzky et al., "Contents," 2 pages, in: Comprehensive Heterocyclic Chemistry, The Structure, Reactions, Synthesis, and Uses of Heterocyclic Compounds. Pergamon Press, Oxford, UK, 1984.
Keller et al., "The role of Raf kinase inhibitor protein (RKIP) in health and disease." Biochemical Pharmacology 68; pp. 1049-1053 (2004).
Kempter et al., "Synthese potentieller Pflanzenschutz- und Schädlingsbekämpfungsmittel aus substituierten Anilinen," Pädagogsische Hochschule, Eingegangen am Jan. 7, 1982, vol. 27, Issue 1, 101-120 (1983).
Kessler et al., "Use of the DNA Flow-Thru Chip, a Three-Dimensional Biochip, for Typing and Subtyping of Influenza Viruses." Journal of Clinical Microbiology. May 2004: vol. 12, pp. 2173-2185.
Khire et al., "Omega-carboxypyridyl substituted ureas as Raf kinase inhibitors: SAR of the amide substituent," Bioorg. Med. Chem. Lett., 2004, vol. 14, pp. 783-786.
Kido, Y., "Vascular Endothelial Growth Factor (VEGF) Serum Concentration Changes during Chemotherapy in Patients with Lung Cancer," Kurume Medical Journal, 48(1): 43-47 (2001).
Klemm et al., "Chemistry of Thienopyridines. XXXVII. Syntheses in the Cyclopenta, Cyclohexa-, and Cycloheptathieno[2,3-b]pyridine Series. Threee Analogs of 9-Amino-1,2,3,4-tetrahydroacridine [1]," J. Heterocyclic Chem., 27, 1990, pp. 1537-1541.
van Muijlwijk-Koezen et al., "Isoquinoline and Quinazoline Urea Analogues as Antagonists for the Human Adenosine $A_3$ Receptor," J. Med. Chem. 2000, 43, pp. 2227-2238.
Kolch et. al., "Raf-1 protein kinase is required for growth of induced NIH/3T3 cells," Nature, vol. 349, Jan. 31, 1991, pp. 426-428.
Kolch et al., "The role of Raf kinases in malignant transformation" Expert reviews in molecular medicine (Apr. 25, 2002) ISSN: 1462-3994 © Cambridge University Press, 18 pages.
Konecny et al., "Association between HER-2/neu and Vascular Endothelial Growth Factor Expression Predicts Clinical Outcome in Primary Breast Cancer Patients," Clinical Cancer Research, 10: 1706-1716 (Mar. 1, 2004).
Korfee et al., "New targeted treatments in lung cancer-overview of clinical trials," Lung Cancer, 45 (Suppl. 2): S199-S208 (2004).
Kraft et al., "Vascular Endothelial Growth Factor in the Sera and Effusions of Patients with Malignant and Nonmalignant Disease," Cancer, 85(1): 178-187 (Jan. 1, 1999).
Kubo et al., "Herbicidal Activity of 1,3,4-Thiadiazole Derivatives," J. Agr. Food Chem. (1970), 18(1), pp. 60-65.
Kubo et al., "Synthesis and structure-activity relationship of quinazoline-urea derivatives as novel orally active VEGF receptor

(56) References Cited

OTHER PUBLICATIONS tyrosine kinase selective inhibitors," Proceedings of the American Association of Cancer Res., 2002, Vol, 43, p. 182, abstract No. 913.
Kuefer et al., "Translational research in renal cell cancer. Illustrated by the example of the vascular endothelial growth factor pathway," Der Urologe, 2006, vol. 45, No. 3, pp. 328, 330-335.
Kumar et al., "Drugs targeted against protein kinases" Expert Opin. Emerging Drugs 6(2):303-315 (2001).
Kupsch et al., "Results of a Phase I Trial of Sorafenib (BAY 43-9006) in Combination with Oxalipiatin in Patients with Refractory Solid Tumors, Including Colorectal Cancer," Clinical Colorectal Cancer, Cancer Information Group Journal, vol. 5 Issue 3, pp. 188-196, abstract (Sep. 2005).
Kurik et al., "Optical Properties of Segmented Ohgourethane with Azomethine Terminal Fragments," Polymer Science, series B, 1996, vol. 38 pp. 2038-2041 abs.
Kyriakis et al., "Raf-1 activates MAP kinase-kinase" Nature, 358, 6385, pp. 417-421 (Jul. 30, 1992).
Laack et al., "Pretreatment serum levels of matrix metalloproteinase-9 and vascular endothelial growth factor in non-small-cell lung cancer," Annals of Oncology, 13(10): 1550-1557 (Oct. 2002).
Dal Lago et al., "Selected Combination Therapy with Sorafenib: A Review of Clinical Data and Perspectives in Advanced Solid Tumors" The Oncologist, vol. 13, No. 8, pp. 845-858 (Aug. 11, 2008).
Lau et al., "Abrogation of c-Raf expression induces apoptosis in tumor cells," Oncogene 16, 1899-1902 (1998).
Lee et al., "BAY-43-9006 Bayer/Onyx," Current Opinion in Investigational Drugs, 2003, vol. 4, No. 6, pp. 757-763.
Lee et al., "Bicyclic midazoles as a Novel Class of Cytokine Biosynthesis Inhibitors," Annals N.Y. Academy of Science, 1993, vol. 696, pp. 149-170.
Lee et al.: "FTY720 induces apoptosis of human hepatoma cell lines through PI3-K-mediated Akt dephosphorylation," Carcinogenesis, vol. 25, No. 12, 2004, pp. 2397-2405.
Lee et al., "Prognostic value of vascular endothelial growth factor expression in colorectal cancer patients," European Journal of Cancer, 36(6): 748-753 (Apr. 2000).
Lee and Heymach, "Emerging Antiangiogenic Agents in Lung Cancer," Clinical Lung Cancer, 7(5): 304-308 (Mar. 2006).
Legros et al., "Imatinib mesylate (STI571) decreases the vascular endothelial growth factor plasma concentration in patients with chronic myeloid leukemia," Blood, 104(2): 495-501 (Prepublished on-line Feb. 19, 2004).
Lemoine, "Overview of ras oncogenes and their clinical potential," Chapter 10, In: Mutant Oncogenes: Targets for Therapy? (eds. Lemoine NR & Epenetos A), Chapman & Hall, London. pp. 85-91.
Lepage et al., "New N-aryl isoxazolecarboxatnides and N-isoxazolybenzamides as anticonvulsant agents," Eur. J. Med. Chem., vol. 27, 1992, pp. 581-593.
Leuner et al., "Improving drug solubility for oral delivery using solid dispersions," European Journal of Pharmaceutics and Biopharmaceutics, 50, 2000, pp. 47-60.
Liang et al., "Differential Expression of VEGF and Its Receptors in the Primary Cells of Various Risk Classified Acute Lymphoblastic Leukemia Patients," Blood 104: Abstract 4446 (2004).
Li et al. "Correlation of Serum VEGF Levels with Clinical Stage, Therapy Efficacy, Tumor Metastasis and Patient Survival in Ovarian Cancer," Anticancer Research, 24: 1973-1980 (2004).
Lin, "Synthesis of 1-(2-Pyridine-1-oxide)-2-(1-Methyl-2-Pyridinium)-Ethane Chloride," OPPI Briefs, vol. 23, No. 1, 1991, pp. 114-115.
Linderholm et al., "Correlation of Vascular Endothelial Growth Factor Content with Recurrences, Survival, and First Relapse Site in Primary Node-Positive Breast Carcinoma After Adjuvant Treatment," Journal of Clinical Oncology, 18(7): 1423-1431 (Apr. 2000).
Linderholm et al., "p53 and Vascular-Endothelial-Growth-Factor (VEGF) Expression Predicts Outcome in 833 Patients with Primary Breast Carcinoma," Int. J. Cancer (Pred. Oncol.): 89(1): 51-62 (2000).

Lissoni et al., "Anti-angiogenic activity of melatonin in advanced cancer patients," Neuroendocrinology Letters, 2001, 22:45-47.
Lissoni et al., "Chemotherapy and angiogenesis in advanced cancer: vascular endothelial growth factor (VEGF) decline as predictor of disease control during taxol therapy in metastatic breast cancer," International Journal of Biological Markers, 15(4): 308-311 (Oct. 1, 2000).
Lissoni et al., "Abnormally enhanced blood concentrations of vascular endothelial growth factor (VEGF) in metastatic cancer patients and their relation to circulating dendritic cells, IL-12 and endothelin-1," Journal of Biological Regulators and Homeostatic Agents, 15(2): 140-144 (Apr. 2001).
Lissoni et al., "Changes in circulating VEGF levels in relation to clinical response during chemotherapy for metastatic cancer," International Journal of Biological Markers, 18(2): 152-155 (2003).
Llovet et al., "Molecular Targeted Therapies in Hepatocellular Carcinoma," Hepatology, vol. 48, No. 4, pp. 1312-1327, 2008.
Lockhart et al., "Phase I/Pilot Study of SU5416 (Semaxinib) in Combination With Irinotecan/Bolus 5-FU/LV (IFL) in Patients With Metastatic Colorectal Cancer," American Journal of Clinical Oncology, 29(2):109-115 (Apr. 2006).
Lorigan et al., "Phase II trial of sorafenib combined with dacarbazine in metastatic melanoma patients" ASCO 2006 DTIC abstract, 2 pages (Jan. 11, 2006).
Lowinger et al., "Design and Discovery of Small Molecules Targeting Raf-1 Kinase," Current Pharmaceutical Design, 2002, vol. 8, pp. 2269-2278.
Lowinger et al., "Discovery of novel class of potent Raf kinase inhibitors: structure activity relationships," Clinical Cancer Research, Nov. 2000, vol. 6 (Suppl.), p. 4533s, abstract No. 335.
Lowy et al "Function and Regulation of RAS" Annual Review of Biochemistry, vol. 62, pp. 851-891, 1993.
Ludwig et al,, "MEK inhibition impairs influenza B virus propagation without emergence of resistant variants," FEBS Letters, 2004, vol. 561, pp. 37-43.
Luo et al., "Enhancement of radiation effects by pXLP-mENDO in a lung carcinoma model," Int. J. Radiation Oncology Biol. Phys., 2005, vol. 63, No. 2, pp. 553-564.
Lyons et al., "Discovery of a novel Raf kinase inhibitor," *Endocrine-Related Cancer*, 2001, vol. 8, pp. 219-225.
Madwed et al., "Pharmacological evaluation of BIRB 796, a selective inhibitor of p38 MAP kinase (MAPK), in animal models of endotoxic shock, inflammation and arthritis," Inflammation Res., 50:S184, abstract No. W22/03, 2001.
Magnuson et al., "The Raf-1 serine/threonine protein kinase," Cancer Biology, vol. 5, 1994, pp. 247-253.
Manenti et al., "Circulating plasma vascular endothelial growth factor in mice bearing human ovarian carcinoma xengraft correlates with tumor progression and response to therapy," Molecular Cancer Therapeutics, 4(5): 715-725 (May 2005).
Mannová et al., "Activation of the N-Ras-PI3K-Akt-mTOR Pathway by Hepatitis C Virus: Control of Cell Survival and Viral Replication," Journal of Virology, Jul. 2005, vol. 79, No. 14, pp. 8742-8749.
Markgraf et al., "Strained Heterocyclic Systems. 19. 1-Azatriptycene and Derivatives," Tetrahedron, vol. 47, No. 2. 1991, pp. 183-188.
Marshall, "MAP kinase kinase kinase, MAP kinase kinase, and MAP kinase," Curr. Opin. Genet. Dev. 4: 82-89, 1994.
Marx, J., "Why a New Cancer Drug Works Well, in Some Patients," Science, vol. 304, pp. 658-659, 2004.
McGoon et al., "Screening, Early Detection, and Diagnosis of Pulmonary Arterial Hypertension," CHEST, 2004: 126, pp. 14S-34S.
Medinger et al., "Hemmung der Tumorangiogenese Neue Therapieoptionen in der Onkologie," Med Welt, 2006, 57, pp. 437-441.
Med Report Deutschland, "Sorafenib zur Therapie des fortgeschrittenen Nierenzellkarzinoms zugelassen," (2006), 1 page.
Meuillet et al., "In Vivo Molecular Pharmacology and Antitumor Activity of the Targeted Akt Inhibitor PX-316," Oncology Research, vol. 14, 2004, pp. 513-527.
Michaelis, "Phenylharnstoff des 1-Phenyl-3-methyl-5-aminopyrazols,"Justus Liebigs Ann. Chem. (JLACBF) 397, 1913, p. 143.

(56) References Cited

OTHER PUBLICATIONS

Milanini et al., "p42/p44 MAP Kinase Module Plays a Key Role in the Transcriptional Regulation of the Vascular Endothelial Growth Factor Gene in Fibroblasts," Journal of Biological Chemistry, 273(29): 18165-18172 (Jul. 17, 1998).

Milano et al., "New molecular targeted therapies in thyroid cancer" Anti-Cancer Drugs (2006) © Lippincott Williams & Wilkins., vol. 17:869-879.

Mills et al., "The Effects of Standard Anthracycline-Based Chemotherapy on Soluble ICAM-1 and Vascular Endothelial Growth Factor Levels in Breast Cancer," Clinical Cancer Research, 10: 4998-5003 (Aug. 1, 2004).

Milojokovic et al., "Immunohistochemical Characterisation of Vascular Endothelial Growth Factor (VEGF) and its Receptors Flt-1 and KDR in Chronic Myeloid Leukaemia (CML) Patients Treated with Imatinib Mesylate," Blood, 104 Abstract 1999 (2004).

Minna et al., "A Bull's Eye for Targeted Lung Cancer Therapy," Science, Vol, 304, pp. 1458-1460, 2004.

Mita et al., "The Molecular Target of Rapamycin (mTOR) as a Therapeutic Target Against Cancer." Cancer Biology & Therapy 2:4 Suppl. 1, S169-S177 (Jul./Aug. 2003).

Moelling et al., "Signal Transuction as Target of Gene Therapy," Institute of Medical Virology, University of Zurich, Recent Results in Cancer Research, vol. 142, pp. 63-71 (1996).

Molhoek et al., "Synergistic inhibition of human melanoma proliferation by combination treatment with B-Raf inhibitor BAY 43-9006 and mTOR inhibitor rapamycin," Journal of Translational Medicine (2005) 3: 39, pp. 1-11.

Monia, "First-and second-generation antisense oligonucleotide inhibitors targeted against human c-raf kinase," (1997) Oligonucleotides as therapeutic agents Wiley, Chichester (Ciba Foundation Symposium 209) pp. 107-123.

Monia et al., "Antitumor activity of a phosphorothioate antisense oligodeoxynucleotide targeted against C-raf kinase," Nature Medicine, vol. 2, No. 6, Jun. 1996, pp. 668-675.

Monia et al., "Sequence-specific antitumor activity of a phosphorothioate oligodeoxyribonucleotide targeted to human C-raj kinase supports and antisense mechanism of action in vivo," Proc. Natl. Acad. Sci USA, vol. 93, 15481-15484 (Dec. 1996).

Morabito et al., Tyrosine Kinase inhibitors of Vascular Endothelial Growth Factor Receptors I Clinical Trials: Current Status and Future Directions, The Oncologist, 11: 753-764 (2006).

Mori et al., "Differential activation of the c-Jun N-terminal kinase/stress-activated protein kinase and p38 mitogen-activated protein kinase signal transduction pathways in the mouse brain upon infection with neurovirulent influenza A virus," Journal of General Virology, 2003, 84, pp. 2401-2408.

Moore et al., "Phase I study to determine the safety and pharmacokinetics of the novel Raf kinase and VEGFR inhibitor BAY 43-9006, administered for 28 days on/7 days off in patients with advanced, refractory solid tumors," Annals of Oncology, 2005, vol. 16, pp. 1688-1694.

Motzer et al., "Survival and Prognostic Stratification of 670 Patients With Advanced Renal Cell Carcinoma", J. Clin. Oncol., 17(8):pp. 2530-2540 (1999).

Mross et al., "Drug-drug interaction pharmacokinetic study with the Raf kinase inhibitor (RKI) BAY 43-9006 administered in combination with irinotecan (CPT-11) in patients with solid tumors," International Journal of Clinical Pharmacology and Therapeutics, 2003, vol. 41, No. 12, pp. 618-619.

Mross et al., "Results from an in vitro and a clinical/pharmacological phase I study with the combination irinotecan and sorafenib" European Journal of Cancer 43, pp. 55-63 (2007).

Murata et al., "Facile Synthesis of New Pyrrolo[3,4-d]pyrimidine-2,4-diones," Chemical and Pharmaceutical Bulletin, vol. 22, No. 5, 1974, pp. 1212-1213.

Murphy et al., "BAY 43-9006 controls tumor growth through inhibition of vascular development," 96th Annual Meeting, Anaheim/Orange County, CA, Apr. 16-20, 2005, abstract No. 2985.

Muthumani et al., "Suppression of HIV-1 viral replication and cellular pathogensis by a novel p38/JNK kinase inhibitor," AIDS. Lippincott Williams & Wilkins, 2004: vol. 18, pp. 739-748.

National Cancer institute, "Carboplatin and Paclitaxel With or Without Sorafenib in Treating Patients With Unresectable Stage III or Stage IV Melanoma", 7 pages, NCT00110019, clinicaltrials.gov. (2005).

National Cancer Institute, "Paclitaxel, Carboplatin, and Radiation Therapy in Treating Patients Who Are Undergoing Surgery for Stage III Non-Small Cell Lung Cancer," 5 pages, NCT00096226, (2005).

National Cancer Institute, "Sorafenib With or Without Paclitaxel and Carboplatin in Treating Patients With Recurrent Ovarian Cancer, Primary Peritoneal Cancer, or Fallopian Tube Cancer," 5 pages, NCT00096200, (2005).

National Cancer Institute, Clinical Trials (PDQ®), "Phase II Randomized Study of ISIS 5132 or ISIS 3521 in Women with Previously Treated Metastatic Breast Cancer," 3 pages, www.cancer.gov website (1998).

National Cancer Institute, Clinical Trials (PDQ®), "Phase II Randomized Study of ISIS 3521 and ISIS 5132 for Locally Advanced or Metastatic Colorectal Cancer," 3 pages, www.cancer.gov website (1998).

National Cancer Institute, Clinical Trials (PDQ®), "Phase II Randomized Study of ISIS 3521 and ISIS 5132 in Patients with Hormone Refractory Prostate Cancer," 3 pages, www.cancer.gov website (1998).

National Cancer Institute, Clinical Trials (PDQ®), "Phase II Study of ISIS 5132 in Patients with Advanced Pancreatic Cancer," 3 pages, www.cancer.gov website (1999).

National Institutes of Health Clinical Center, "BAY 43-9006 (Sorafenib) to Treat Relapsed Non-Small Cell Lung Cancer", 4 pages, NCT00098254, clinicaltrials.gov (2005).

Naumann et al., "Raf protein serine/threonine kinases" in: Protein Phosphorylation, VCH Verlagsgeasellschaft mbH Chapter 7, pp. 203-236 (1996).

Naumann et al., "The Role of Raf Kinases in Development and Growth of Tumors" Recent Results in Cancer Research, vol. 143, pp. 237-244 (1997).

Nemunaitis et al., "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).

Neufeld et al., "Vascular endothelial growth factor (VEGF) and its receptors," The FASEB Journal, 13: 9-22 (Jan. 1999).

"Nexavar Receives FDA Fast Track Designation for Skin Cancer" 4 pages, (Jul. 21, 2006) http://www.medicalnewstoday.com/articles/47793.php (last visited on Jun. 16, 2008).

Nicholson, K. M. et al.: "The protein kinase B/Akt signalling pathway in human malignancy," Cellular Signalling Signalling 14, 2004, pp. 381-395.

Nickel et al., "Carboxylic acid analogues of suramin, potential filaricides," Indian Journal of Chemistry, Feb. 1991, vol. 300, pp. 182-187.

Nilsson et al., "Vascular Endothelial Growth Factor (VEGF) Pathway," Journal of Thoracic Oncology, 1(8): 768-770 (Oct. 2006).

Noble et al., "Protein Kinase Inhibitors: Insights into Drug Design From Structure," Science, (2004), vol. 303, pp. 1800-1805.

O'Dwyer et al., "c-raf-1 Depletion and Tumor Responses in Patients Treated with the c-raf-1 Antisense Oligodeoxynucleotide ISIS 5132 (CGP 99846A)," Clinical Cancer Research vol. 5, pp. 3977-3982 (Dec. 1999).

Oka et al., "Constitutive Activation of Mitogen-activated Protein (MAP) Kinases in Human Renal Cell Carcinoma," Cancer Research 55, pp. 4182-4187, (Sep. 15, 1995).

Gollob et al., "Phase II trial of sorafenib (BAY 43-9006) in combination with interferon alpha 2b in patients with metastatic renal cell carcinoma," European Journal of Cancer, 2005, vol. 3, No. 2, pp. 226-227, abstract No. 795.

Osella-Abate et al., "VEGF-165 serum levels and tyrosinase expression in melanoma patients: correlation with the clinical course," Melanoma Research, 12: 325-334 (Aug. 2002).

(56) References Cited

OTHER PUBLICATIONS

Oza et al., "Phase II study of CGP 69846A (ISIS 5132) in recurrent epithelial ovarian cancer: an NCIC clinical trials group study (NCIC IND .116)," PubMed Abstract 12694666, Gynecol. Oncol. Apr. 2003: 89(1):129-133.
Ozols, "New Developments With Carboplatin in the Treatment of Ovarian Cancer," *Seminars in Oncology*, vol. 19, No. 1, Supplement 2, Feb. 1992, pp. 85-89.
Panka et al., "BAY 43-9006 induces apoptosis in melanoma cell lines," 96th Annual Meeting, Anaheim/Orange County, CA, Apr. 16-20, 2005, abstract No. 5328.
Panteva et al., "Hepatitis viruses and the MAPK pathway: is this a survival strategy?" Virus Research, 2003, vol. 92: 131-140.
Paquette, Table of Contents for The Encyclopedia of Reagents for Organic Synthesis, John Wiley, New York, 1994 Table of Contents.
Pavlović-Lažetić et al., "Bioinformatics analysis of SARS coronavirus genome polymorphism," May 25, 2004, BMC Bioinformatics, vol. 5:65, 14 pages.
Pederson et al., "Early changes in serum IL-6 and VEGF levels predict clinical outcome following first-line therapy in aggressive non-Hodgkin's lymphoma," Ann. Hematol., 84:510-516 (2005).
Peters, H.D., "Sorafenib bei soliden Tumoren," Focus Onkologie, 2007, Auflage 12000, 6 pages.
Robert et al., "Phase I trial of sorafenib (BAY 43-9006) in combination with interferon alpha-2a in patients with unresectable and/or metastatic renal cell carcinoma and malignant melanoma," European Journal of Cancer, 2005, vol. 3, No. 2, p. 254, Abstract 883.
Hu et al., "Soluble Vascular Endothelial Growth Factor Receptor 1, and Not Receptor 2, Is an Independent: Prognostic Factor in Acute Myeloid Leukemia and Myelodysplastic Syndromes," Cancer 2004, vol. 100, No. 9, pp. 1884-1891.
Raez et al., "New developments in chemotherapy for advanced non-small cell lung cancer," Current Opin. Oncol., vol. 18, 2006, pp. 156-161.
Rahmani et al., "Apoptosis Induced by the Kinase Inhibitor BAY 43-9006 in Human Leukemia Cells Involves Down-regulation of Mcl-1 through Inhibition of Translation," J. Biol. Chem. 280(42):35217-35227 (2005).
Rak et al., "Oncogenes and Angiogenesis: Signaling Three-Dimensional Tumor Growth," Journal of Investigative Dermatology Symposium Proceedings (2000) 5, 24-33.
Rak et al., "Oncogenes and Tumor Angiogenesis: Differential Modes of Vascular Endothelial Growth Factor Up-Regulation in *ras*-transformed Epithelial Cells and Fibroblasts," Cancer Research 60, pp. 490-498, (Jan. 15, 2000).
Rak et al., "Oncogenes as inducers of tumor angiogenesis," Cancer and Metastasis Reviews 14: 263-277, 1995.
Sturm-Ramirez et al., "Reemerging H5N1 Influenza Viruses in Hong Kong in 2002 Are Highly Pathogenic to Ducks," Journal of Virology, May 2004, 78(9):4892-4901.
Raposo et al., "Catalysis of Nucleophilic Addition of Pyrrolidine to 2-(5*H*)-Furanone through Chromenone Cleft-Type Receptors," Tetrahedron Letters vol. 37, No. 38, pp. 6947-6950, 1996.
Ratain et al., "Phase II Placebo-Controlled Randomized Discontinuation Trial of Sorafenib in Patients with Metastatic Renal Cell Carcinoma," Journal of Clinical Oncology vol. 24 No. 16, pp. 2505-2512 (Jun. 1, 2006).
Ravi et al., "Activated Raf-1 Causes Growth Arrest in Human Small Cell Lung Cancer Cells," J. Clin. Invest., vol. 101, No. 1, pp. 153-159 (1998).
Reddy et al., "Sorafenib: recent update on activity as a single agent and in combination with interferon-alpha2 in patients with advanced-stage renal cell carcinoma," Clin. Genitourin. Cancer 4:246-248 (2006) abstract.
Redman et al., "p38 Kinase Inhibitors for the Treatment of Arthritis and Osteoporosis: Thienyl, Furyl, and Pyrrolyl Ureas," Bioorganic & Medicinal Chemistry Letters 11 (2001) 9-12.
Regan et al., "Pyrazole Urea-Based Inhibitors of p38 MAP kinase: From Lead Compound to Clinical Candidate," J. Med. Chem. 45:2994-3008, 2002.

Richly et al., "A phase I clinical and pharmacokinetic study of the Raf kinase inhibitor (RKI) BAY 43-9006 administered in combination with doxorubicin in patients with solid tumors," International Journal of Clinical Pharmacology and Therapeutics, 2003, vol. 41, No. 12, pp. 620-621.
Richly et al., "Results of a Phase I trial of sorafenib (BAY 43-9006) in combination with doxorubicin in patients with refractory solid tumors," Annals of Oncology, 2006, 17, pp. 866-873.
Richly et al., "Results of a phase I trial of BAY 43-9006 in combination with doxorubicin in patients with primary hepatic cancer," International Journal of Clinical Pharmacology and Therapeutics, 2004, vol. 42, No. 11, pp. 650-651.
Ridley et al., "Actions of IL-1 are Selectively Controlled by p38 Mitogen-Activated Protein Kinase, Regulation of Prostaglandin H Synthase-2, Metalloproteinases, and IL-6 at Different Levels," The American Association of Immunologists, 1997, J. Immunol. vol. 158, pp. 3165-3173.
Rini and Small, "Biology and Clinical Development of Vascular Endothelial Growth Factor-Targeted Therapy in Renal Cell Carcinoma," Journal of Clinical Oncology, 23(5): 1028-1043 (Feb. 10, 2005).
Robak et al., "Vascular endothelial growth factor and its soluble receptors VEGFR-1 and VEGFR-2 in the serum of patients with systemic lupus erythematosus," Mediators of Inflammation 12(5):293-298 (Oct. 2003).
Robertson et al. "HIV-1 Nomenclature Proposal," Science, Apr. 7, 2000, pp. 55-57. vol. 288.
Robinson et al., "Enhanced Radiosensitization with Gemcitabine in Mismatch Repair-Deficient HCT116 Cells," Cancer Research 63, 6935-6941 (Oct. 15, 2003).
Robke et al., "Conversion of Aminopyridines into *N*-Oxides by Caro's Acid Anion (Peroxymonosulfate)," J. Chem. Research (S), 1993, pp. 412-413.
Roche, E. B., "Structural Aspects of Selective Distribution," Chapter 3, in: Design of Biopharmaceutical Properties Through Prodrugs and Analogs, American Pharmaceutical Association, Washington, D.C., 1977, pp. 27-46.
Rodriguez et al., "A sensitive fluorometric enzyme-linked immunosorbent assay that measures vascular endothelial growth factor$_{165}$ in human plasma," Journal of Immunological Methods, 219(1-2): 45-55 (Oct. 1998).
Roman et al., "Human Papillomaviruses: Are We Ready to Type?" Clinical Microbiology Reviews. Apr. 1989: vol. 2, pp. 166-190.
Rowinsky et al., "Sequences of Taxol and Cisplatin: A Phase I and Pharmacologic Study," Journal of Clinical Oncology, vol. 9, No. 9, Sep. 1991, pp. 1692-1703.
Rowinsky et al., "Taxol: The First of the Taxanes, an Important New Class of Antitumor Agents," *Seminars in Oncology*, vol. 19, No. 6, Dec. 1992, pp. 646-662.
Rubin, Lewis J., "Primary Pulmonary Hypertension," New England Journal of Medicine, vol. 336, No. 2, pp. 111-117 (1997).
Rudin et al., "Phase I Trial of ISIS 5132, an Antisense Oligonucleotide Inhibitor of c-*raf*-1, Administered by 24-hour Weekly Infusion to Patients with Advanced Cancer" Clinical Cancer Research vol. 7, pp. 1214-1220 (May 2001).
Russo et al., "Sintesi Di Derivati 2,6-Sostituiti Del 5H-1,3,4-Tiadiazo [3,2-a]-s-Triazina-5,7-Dione," Il Farmaco, Ed.Sci. (1978), 33(12), 972-983.
Rydén et al., "Tumor specific VEGF-A and VEGFR2/KDR protein are co-expressed in breast cancer," Breast Cancer Research and Treatment, 82(3):147-154 (Dec. 2003).
Salvatore et al., "BRAF is a Therapeutic Target in Aggressive Thyroid Carcinoma," Clin. Cancer Res. pp. 1623-1629; 12(5) (Mar. 1, 2006).
Sarkar et al., "Indole-3-Carbinol and Prostate Cancer," Journal of Nutrition 134, 2004, pp. 3493S-3498S.
Serajuddin, "Solid Dispersion of Poorly Water-Soluble Drugs: Early Promises Subsequent Problems, and Recent Breakthroughs," Journal of Pharmaceutical Sciences vol. 88, No. 10, pp. 1058-1066 (Oct. 1999).
Shaked et al., "Cellular and Molecular Surrogate Markers to Monitor Targeted and Non-Targeted Antiangiogenic Drug Activity and Determine Optimal Biologic Dose," Current. Cancer Drug Targets, 5: 551-559 (Nov. 2005).

(56) References Cited

OTHER PUBLICATIONS

Shelton et al., "Effects of the RAF/MEK/ERK and PI3K/AKT signal transduction pathways on the abrogation of cytokine-dependence and prevention of apoptosis in hematopoietic cells," Oncogene, vol. 22, No. 16, Apr. 2003; pp. 2478-2492.

Shi et al., "Constitutive and Inducible Interleukin 8 Expression by Hypoxia and Acidosis Renders Human Pancreatic Cancer Cells More Tumorigenic and Metastatic," Clinical Cancer Research, 1999, vol. 5, pp. 3711-3721.

Shimanuki et al., "Role of Serum Vascular Endothelial Growth Factor in the Prediction of Angiogenesis and Prognosis tor Non-small Cell Lung Cancer," Lung, 183: 29-42 (2005).

Simone, Joseph, V., "Part XIV. Oncology," in: Cecil Textbook of Medicine, 20th Edition, vol. 1, Feb. 3, 1997. W.B. Saunders Company, pp. 1004-1010.

Sinkula et al., "Rationale for Design of Biologically Reversible Drug Derivatives: Prodrugs," Journal of Pharmaceutical Sciences, vol. 64, No. 2, Feb. 1975, pp. 181-210.

Siu et al., "Phase I study of oral raf-1 kinase inhibitor BAY 43-9006 with gemcitabine in patients with advanced solid tumors," Abstract No. 828, Proc. Am. Soc. Clin. Oncol., 2003, vol. 22, p. 207.

Siu et al., "Phase I Trial of Sorafenib and Gemcitabine in Advanced Solid Tumors with an Expanded Cohort in Advanced Pancreatic Cancer," Clin. Cancer Res. 12(1):144-151 (2006).

Smith et al., "Discovery of Heterocyclic Ureas as a New Class of Raf Kinase Inhibitors: Identification of a Second Generation Lead by a Combinatorial Chemistry Approach," Bioorganic & Medicinal Chemistry Letters, 2001, vol. 11, pp. 2775-2778.

Smith et al., (Abstract) "Recent Advances in the Research and Development of RAF Kinase Inhibitors," Current Topics in Medicinal Chemistry 6(11):1071-1089 (2006).

Smyth, R.M. et al., "Anchimeric Assistance in the Specific Acid-catalysed Hydration of Benzonitriles" J. Chem. Soc. Perkin Trans. 2 1993 pp. 2171-2174.

Song, Huai-Dong et al., "Cross-host evolution of severe acute respiratory syndrome coronavirus in palm civet and human." Proc. Nati. Acad. Sci. USA 102(7):2430-2435 (2005).

Sorbara et al., "BAY-43-9006," Drugs of the Future, 2002, vol. 27, No. 12, pp. 1141-1147.

van Spronsen et al., "Novel treatment strategies in clear-cell metastatic renal cell carcinoma," Anti-Cancer Drugs, 2005, vol. 16, pp. 709-717.

Stadler et al., "A Randomized Phase II Trial of the Antiangiogenic Agent SU5416 in Hormone-Refractory Prostate Cancer," Clinical Cancer Research, 10: 3365-3370 (May 15, 2004).

Stahl et al., "Deregulated Akt3 Activity Promotes Development of Malignant Melanoma," Cancer Research, vol. 64, No. 19; Oct. 2004; pp. 7002-7010.

Stavchansky et al., "Evaluation of the Bioavailability of a Solid Dispersion of Phenytoin in Polyethylene Glycol 6000 and a Commercial Phenytoin Sodium Capsule in the Dog," Journal of Pharmaceutical Sciences, vol. 73, No. 6, Jun. 1984, pp. 733-736.

Krontiris, "Chapter 71. Molecular and Cellular Biology of Cancer," and Capizzi, "Chapter 72, Principles of Treatment of Cancer," in: Internal Medicine, 4th Edition, Stein, Jay H., MD, Ed., Mosby, 1994, pp. 699-715.

Sternberg et al., "Conspiracy Theory: RAS and RAF Do Not Act Alone" Cell, vol. 95, pp. 447-450 (Nov. 13, 1998).

Stella et al., "Prodrugs and Site-Specific Drug Delivery," Journal of Medicinal Chemistry, vol. 23, No. 12, Dec. 1980, pp. 1275-1282.

Stella et al., "Prodrugs as therapeutics," Exp. Opin. Ther. Patents 14(3): 277-280 (2004).

Stella et al., "Prodrugs. Do They Have Advantages in Clinical Practice?" Drugs, vol. 29, 1985, pp. 455-473.

Stevenson et al., "Phase I Clinical/Pharmacokinetic and Pharmacodynamic Trial of the c-raf-1 Antisense Oligonucleotide ISIS 5132 (CGP 69846A)," The Journal of Clinical Oncology, vol. 17, No. 7: pp. 2227-2236 (Jul. 1999).

Stöckl et al., "Integrity of c-Raf-1/MEK signal transduction cascade is essential for hepatitis B virus gene expression," Oncogene. Nature Publishing Group, 2003: vol. 22, pp. 2604-2610.

Stokoe et al., "Activation of c-Raf-1 by Ras and Src through different mechanisms: activation in vivo and in vitro," The Embo Journal, vol. 16 No. 9 pp. 2384-2396 (1997).

Storm et al., "raf Oncogenes in Carcinogenesis" Critical Reviews in Oncogenesis, vol. 2, Issue 1, pp. 1-8 (1990).

Strumberg, D., "Preclinical and Clinical Development of the Oral Multikinase Inhibitor Sorafenib in Cancer Treatment," Drugs of Today, 41(12): 773-784 (2005).

Strumberg et al., "Phase I Clinical and Pharmacokinetic Study of the Novel Raf Kinase and Vascular Endothelial Growth Factor Receptor inhibitor BAY 43-9006 in Patients With Advanced Refractory Solid Tumors," Journal of Clinical Oncology, Feb. 10, 2005, vol. 23, No. 5, pp. 965-972.

Strumberg et al., "Phase I Clinical, Pharmacokinetic and Pharmacodynamic Study of the Raf Kinase Inhibitor BAY 43-9006 in Patients with Locally Advanced or Metastatic Cancer," Proc. Am. Soc. Chin. Oncol. 20: 2001 (abstr 330).

Strumberg et al., "Results of phase I pharmacokinetic and pharmacodynamic studies of the Raf kinase inhibitor BAY 43-9006 in patients with solid tumors," International Journal of Clinical Pharmacology and Therapeutics, 2002, vol. 40, No. 12, pp. 580-581.

Strumberg et al., "Sorafenib Neue Therapieoption in der Onkologie," Krankerthauspharmazie, 2007, vol. 28, pp. 93-97, pp. 1/5, 2/5, 3/5 and 4/5.

Suzuki et al., "The role of p38 mitogen-activated protein kinase in IL-6 and IL-8 production from the TNF-α- or IL-1β-stimulated rheumatoid synovial fibroblasts," FEBS Letters (2000), vol. 465, pp. 23-27.

Swarbrick et al., "Contents, pp. xvii-xviii in: Encyclopedia of Pharmaceutical Technology." 2nd Edition, Marcel Dekker, Inc. 2002.

Swart, Guido W.M., "International Melanoma Research Congress—Foundation for Melanoma Research," IDRUGS: The Investigational Drugs Journal, Aug. 2003; vol. 6, No. 8, pp. 752-754.

Tabellini et al., "Novel 2'-substituted, 3'-deoxy-phosphatidyl-myo-inositiol analogues reduce drug resistance in human leukaemia cell lines with an activated phosphoinositide 3-kinase/Akt pathway," British Journal of Haematology, 126, 2004, pp. 574-582.

Takimoto et al., "Safety and anti-tumor activity of sorafenib (Nexavar®) in combination with other anti-cancer agents: a review of clinical trials," Cancer Chemotherapy and Pharmacology (2008) 61:535-548.

Tamm et al., "Hypoxia-Induced Interleukin-6 and Interleukin-8 Production Is Mediated by Platelet Activation Factor and Platelet-Derived Factor in Primary Human Lung Cells," Am. J. Respir. Cell Mol. Biol. vol. 19, pp. 653-661, (1998).

Tanaka et al., "Current stratus antiangiogenic therapy for cancer: hepatocellular carcinoma," Int. J. Clin. Oncol. (2006) 11:82-89 (2006).

Tang et al., "Inhaled nitric oxide attenuates pulmonary hypertension and improves lung growth in infant rats after neonatal treatment with a VEGF receptor inhibitor." Am. J. Physiol. Lung Cell. Mol. Physiol. 287:L344-L351 (2004).

Tarzia et al., "Synthesis and anti-inflammatory properties of some pyrrolo(1H,3H) [3,4-d]pyrimidin-2-ones and pyrrolo=(1H,6H)[3,4-d]pyrimidin-2-ones," Chemical Abstracts, vol. 91, 1979, 91:74558p.

Teknos et al., "Elevated Serum Vascular Endothelial Growth Factor and Decreased Survival in Advanced Laryngeal Carcinoma," Head & Neck, 24: 1004-1011 (Nov. 2002).

Thaimattam et al., "3D-QSAR CoMFA, CoMSIA studies on substituted ureas as Raf-1 kinase inhibitors and its confirmation With structure-based studies," Bioorganic & Medicinal Chemistry, 2004, vol. 12, pp. 6415-6425.

Thelen et al., "VEGF-D promotes tumor growth and lymphatic spread in a mouse model of hepatocellular carcinoma" Int. J. Cancer 122, 2471-2481 (2008) © 2008 Wiley-Liss, Inc.

Thompson et al., "Recent progress in targeting the Raf/MEK/ERK pathway with inhibitors in cancer drug discovery," Curr. Opin. Pharmacol., Aug. 2005, vol. 5, No. 4, pp. 350-356.

Tong et al., "Pharmacodynamic Monitoring of BAY 43-9006 (Sorafenib) in Phase I Clinical Trials Involving Solid Tumor and

(56) References Cited

OTHER PUBLICATIONS

AML/MDS Patients, Using Flow Cytometry to Monitor Activation of the ERK Pathway in Peripheral Blood Cells," Cytometry Part B (Clinical Cytometry) 70B: 107-114 (2006).

Trost et al., "Contents," vol. 1-9, 36 pages in: Comprehensive Organic Synthesis: Selectivity, Strategy & Efficiency in Modern Organic Chemistry, Pergamon Press, Oxford, UK. 1991.

Gupta-Abramson et al., "Phase II Trial of Sorafenib in Advanced Thyroid Cancer" Journal of Clinical Oncology vol. 26, No. 29, pp. 4714-4719 (Oct. 10, 2008).

Veronese et al., "Mechanisms of Hypertension Associated with BAY 43-9006," Journal of Clinical Oncology, 2006, vol. 24, No. 9, pp. 1363-1369.

Vivanco et al., "The Phosphatidylinositol 3-Kinase-AKT Pathway in Human Cancer," Nature Reviews Cancer, vol. 2, Jul. 2002. pp. 489-501.

Vlahos et al., "A Specific inhibitor of Phosphatidylinositol 3-Kinase, 2-(4-Morpholinyl)-8-phenyl-4H-1-benzopyran-4-one (LY294002)," The Journal of Biological Chemistry, vol. 269, No. 7, 1994, pp. 5241-5248.

Wakelee et al., "Targeting Angiogenesis with Vascular Endothelial Growth Factor Receptor Small-Molecular Inhibitors: Novel Agents with Potential in Lung Cancer," Clinical Lung Cancer, 7(Suppl 1): S31-S38 (Sep. 2005).

Wald et al., "Involvement of the CXCL12/CXCR4 pathway in the advanced liver disease that is associated with hepatitis C virus or hepatitis B virus," Eur. J. Immunol., vol. 34, p. 1164-1174 (2004).

Wan et al., "Mechanism of Activation of the RAF-ERK Signaling Pathway by Oncogenic Mutations of B-RAF," Cell, Mar. 19, 2004, vol. 116, pp. 855-867.

Weekly Epidemiological Record, "Influenza," World Health Organization. Apr. 1999; vol. 14, pp. 111-112.

Wermuth, C. G., "Designing Prodrugs and Bioprecursors II: Bioprecursor Prodrugs," in: The Practice of Medicinal Chemistry, Academic Press Limited 1996, pp. 697-715.

White et al., "Heterocyclic Ureas: Inhibitors of Acyl-CoA:Cholesterol O-Acyltransferase as Hypocholesterolemic Agents," J. Med. Chem. 1996, 39, pp. 4382-4395.

Wierzbowska et al., "Circulating VEGF and its soluble receptors sVEGER-1 and sVEGFR-2 in patients with acute leukemia," Eur. Cytokine Netw., 14(3): 149-153 (Sep. 2003).

Wilhelm et al., "A Novel RAF Kinase Inhibitor Blocks the RAF/MEK/ERK Pathway in Tumor Cells," Poster, 92nd Annual Meeting of the American Association for Cancer Research, Mar. 24-28, 2001, New Orleans, LA USA, 1 page.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, vol. 64, pp. 7099-7109.

Wilhelm et al., "BAY 43-9006: Preclinical Data," Curr Pharm Des, 2002, vol. 8, No. 25, pp. 2255-2257.

Wilhelm et al., "Discovery and development of sorafenib: a multikinase inhibitor for treating cancer," Nature Reviews, Drug Discovery, 2006, vol. 5, pp. 835-844.

Wilhelm et al., "Preclinical overview of sorafenib, a multikinase inhibitor that targets both Raf and VEGF and PDGF receptor tyrosine kinase signaling," Mol. Cancer Ther., 2008, vol. 7, No. 10, pp. 3129-3140.

Wilkinson Geoffrey, "Contents," 7 pages in: Comprehensive Organometallic Chemistry. The Synthesis, Reactions, and Structures of Organometallic Compounds, Pergamon Press, Oxford, U.K. 1982: vol. 1-3.

Wilson et al., "The structural basis for the specificity of pyridinylimidazole inhibitors of p38 MAP kinase," Chemistry & Biology, 1997, vol. 4, No. 6, pp. 423-431.

Stollorz, "Die Krebsformel, die der Zufall fand," Frankfurter Allgemeine Sonntagszeitung, Jul. 2, 2006, NR 26, pp. 68-69.

Wissner et al., "Analogues of Platelet Activating Factor. 7. Bis-Aryl Amide and Bis-Aryl Urea Receptor Antagonists of PAF," J. Med, Chem., 1992, vol. 35, pp. 4779-4789.

Wojnowski et al., "Enuothelial apoptosis in Braf-deficient mice," Nature Genetics vol. 16, pp. 293-297 (Jul. 1997).

Onyx Pharmaceuticals, Inc.,"Novel RAF Kinase Inhibitor Bay 43-9006 Shows Early Signs of Tolerability and Activity in Phase 1B Combination Trials Reported at ASCO," 1 page, (Press Release: Jun. 2, 2003).

Wright et al., "Bovine Immunodeficiency Virus Expression in Vitro is Reduced in the Presence of β-Chemokines, MIP-1α, MIP-1β and RANTES." Veterinary Research Communications. 2002: vol. 26, pp. 239-250.

Wright et al., "Clinical Trials Referral Resource. Current Clinical Trials of BAY 43-9006, Part 1," Oncology, Apr. 2005, vol. 19, No. 4: pp. 499-502.

Wu et al., "Plasma vascular endothelial growth factor is useful in assessing progression of breast cancer post surgery and during adjuvant treatment," International Journal of Oncology, 20: 509-516 (2002).

Xu et al., "Hypoxia-induced Elevation in Interleukin-8 Expression by Human Ovarian Carcinoma Cells," Cancer Research. 1999, vol. 59, pp. 5822-5829.

He et al., "Oral Formulation of a Novel Antiviral Agent, PG301029, in a Mixture of Gelucire 44/14 and DMA (2:1, wt/wt)," AAPS PharmSciTech 2005; vol. 6 (1) Article 1, 5 pages, (http://www.aapsharmscitech.org).

Yamaguchi et al., "Expression of Vascular Endothelial Growth Factor in Human Hepatocellular Carcinoma," Hepatology, 28(1) pp. 68-77 (1998).

Yang et al. "Akt/Protein Kinase B Signaling Inhibitor-2, a Selective Small Molecule Inhibitor of a Akt Signaling with Antitumor Activity in Cancer Cells Overexpressing Akt," Cancer Research, 64, Jul. 1, 2004, pp, 4394-4399.

Yang et al., "Antiviral chemotherapy control of poxvirus infections through inhibition of cellular signal transduction," The Journal of Clinical Investigation, 2005: 115(2):pp. 379-387.

Yeh et al., "Characterization of severe acute respiratory syndrome coronavirus genomes in Taiwan: Molecular epidemiology and genome evolution," Proc. Natl. Acad. Sci. USA Feb. 24, 2004, 101(8):2542-2547.

Yu et al., "The role of Mcl-1 downregulation in the proapoptotic activity of the multikinase inhibitor BAY 43-9006," Oncogene 24:6861-6869 (2005).

Zachos et al., "Herpes Simplex Virus Type 1 Infection Stimulates p38/c-Jun N-terminal Mitogen-activated Protein Kinase Pathways and activates Transcription Factor AP-1," Journal of Biological Chemistry, The American Society for Biochemistry and Molecular Biology, Inc. 1999: vol. 274, pp. 5097-5103.

Zangari et al., "Phase II Study of SU5416, a Small Molecule Vascular Endothelial Growth Factor Tyrosine Kinase Receptor Inhibitor, in Patients with Refractory Multiple Myeloma," Clinical Cancer Research, 10: 88-95 (Jan 1, 2004).

Norden-Zfoni, Anat. "Blood-Based Biomarkers of SU11248 Activity and Clinical Outcome in Patients with Metastatic Imatinib-Resistant Gastrointestinal Stromal Tumor," Clin. Cancer. Res. 2007; 13(9):2643-2650 May 1, 2007.

Zhao et al,, "Moderate mutation rate in the SARS coronavirus genome and its implications," BMC Evolutionary Biology, 2004, 4:21, 9 pages.

Zhu et al., "From the Cyclooxygenase-2 Inhibitor Celecoxib to a Novel Class of 3-Phosphoinositide-Dependent Protein Kinase-1 Inhibitors," Cancer Research 64, Jun. 15, 2004, pp. 4309-4318.

Carter et al., "Anti-tumor Efficacy of the Orally Active RAF Kinase Inhibitor Bay 43-90006 in Human Tumor Xenograft Model," #4954. Proceedings of the American Association for Cancer Res., 2001, vol. 42, p. 923.

Iwadate et al., MEDLINE/NLM NLM8336809 "Intra-arterial ACNU, CDDP chemotherapy for brain metastases from lung cancer: comparison of cases with and without intra-arterial mannitol infusion," 1 page, abstract.

Kubo et al., "Synthesis and Structure-Activity Relationship of Quinazohne-Urea Derivatives as Novel Orally Active VEGF Recep-

(56) References Cited

OTHER PUBLICATIONS tor Tyrosine Kinase Selective Inhibitors," Proceedings of the American Association of Cancer Res., 2002, vol. 43, p. 182, abstract No. 913.
Riedl et al., # 4956 "Potent *Raf* Kinase Inhibitors from the Diphenylurea Class: Structure Activity Relationships," Proceedings of the American Association for Cancer Research, vol. 42, Mar. 2001, p. 923, 92nd Annual Meeting of the American Association for Cancer Research; New Orleans, LA, USA; Mar. 24-28, 2001.
Strumberg et al., abstract No. #2921 "Phase I and Pharmacokinetic Study of the Raf Kinase Inhibitor Bay 43-9006 in Patients with Locally Advanced or Metastic Cancer," Proceedings of the American Association for Cancer Research, vol. 42, Mar. 2001, p. 543, 92nd Annual Meeting of the American Association for Cancer Research;New Orleans, LA, USA; Mar. 24-28, 2001.
Abstract of DE 3305866 A1, Aug. 23, 1984, BASF AG et al.
Abstract of EP 4931 A (Equivalent 4,240,820), Bayer AG, 1 page.
Abstract of EP 16371 (1980), 1 page, Hoffmann-La Roche AG.
Abstract of EP 16371, Oct. 1, 1980, 1 page.
Abstract of EP 116932, Aug. 29, 1984, 2 pages.
Abstract of EP 116932, (1984), 2 pages, BASF AG.
Abstract of EP 0202538, (1986), 3 pages.
Abstract of EP 0202538 A1, Growth Promoting Agents, Nov. 26, 1986, 4 pages, Bayer AG.
Abstract of EP 0405233A1, Mitsubishi Kasei Corp., 2 pages.
Abstract of EP 0405233A1, Tetsuo Sekiya et al., 1 page.
Abstract of EP 0676395A2, (1995), 3 pages, Hoechst AG.
Abstract of EP 676395, (U.S. equivalent 5,698,581), Dec. 16, 1997, 1 page.
Patent Abstracts of Japan 02-022650, Jan. 25, 1990, 2 pages, Konica Corp.
esp@cenet Abstracts of Japan 02-022650, Jan. 25, 1990, 1 page.
Patent Abstracts of Japan 02-023337, Jan. 25, 1990, 2 pages, Konica Corp.
Patent Abstracts of Japan 63-214752, Sep. 7, 1988, 2 pages, family member of JP 6-07512 B4, Fuji Photo Film Co. Ltd.
esp@cenet Abstract of Japan 02-023337, 1 page.
Abstract of JP 55162772 A2, Preparation of Substituted Acetic Acid Derivatives, Shiongi & Co., Ltd. Dec. 1980, 1 page.
Esp@cenet Abstract of WO 9822103, May 28, 1998, Philip Hedge et al.
Abstract of WO 9822098 A2, QLT Phototherapeutics Inc. et al., May 28, 1998, 1 page.
Abstract of WO 9822103 A1, Zeneca Limited, published May 28, 1998, 1 page.
Abstract of WO 9852559 A1, Bayer Corp. et al., published Nov. 26, 1998, 1 page.
Abstract of WO 9852562 A1, Verkaik, MSE, et al., published Nov. 26, 1998, 1 page.
Abstract of WO 9900357 A1, Vertex Pharm. Inc., published Jan. 7, 1999, 1 page.
Abstract of WO 9900364 A1, Pharmacia & Upjohn S.P.A. et al., published Jan. 7, 1999, 1 page.
Abstract of WO 9932098 A2, Janssen Pharm NV, published Jul. 1, 1999, 1 page.
Abstract of WO 9932106 A1, Bayer Corp., published Jul. 1, 1999, 1 page.
Abstract of WO 9932148 A1, Beth Israel Deaconess Medical Center et al., pub. Jul. 1, 1999, 1 page.
Abstract of WO 9932436 A1, Bayer Corp., published Jul. 1, 1999, 1 page.
Abstract of WO 9932455 A1, Bayer Corp., published Jul. 1, 1999, 1 page.
Abstract of WO 9932457 A1, Hoechst Marion Roussel Deutschland GmbH et al., published Jul. 1, 1999, 1 page.
Caplus 72:79046, Abstract of CH 479557, "Tuberculostatic and cancerostatic polybasic ureas," Dr. A. Wander, Oct. 15, 1969, 6 pages.
Caplus 84:180049, Abstract JP 56029871, "Substituted acetic acid derivatives," Hamada, Yoshinori et al., Jul. 10, 1981, 1 page.
Caplus 84:43857, Abstract JP 58021626, "Alkanoic acid derivatives containing, a pyridine ring," Maeda, Ryozo et al., May 2, 1983, 1 page.
Caplus 86:72448, Abstract JP 57053785, "Pyridine derivatives," Maeda, Ryozo et al., Nov. 15, 1982, 1 page.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat," Chemical Life Science, pp. 157-166, 1977, 1 page.
Caplus 98:78152, Abstract of JP 57185219, "Antitumor benzophenone derivatives," Nov. 15, 1982, 1 page, Chugai Pharmaceutical Co., Ltd.
Caplus 113:106314, Abstract of JP 2022650, "Silver halide color photographic material containing a cyan coupler of 2-ureido-phenol type to improve dye developability and remove lecuo cyan dye," Noboru Mizukura et al. Jan. 25, 1990, 1 page.
Caplus 113:142130, Abstract of JP 2023337, "Silver halide photographic material cntaining phenolic cyan coupler a colorless cyan coupler," Toshihiko Yagi et al., Jan. 25, 1990, 1 page.
Caplus 125:245169, "Production of murine monoclonal antibodies against sulcofuron and flucofuron by in vitro immunization," G. A. Bonwick et al., J. Immunol. Methods, 196(2), pp. 163-173, 1996, 1 page.
Caplus 126:166148, "Inhibitors of coenzyme A-independent transacylase induce apoptosis in human HL-60 cells," James O. Winkler et al., J. Pharmacol. Exp. Ther. 279(2), pp. 956-966, 1996, 2 pages.
Dearden et al.,"Quantitative structure-biodegradability studies: an investigation of the MITI aromatic compound data-base," in: Biodegradability Prediction, Edited by Willie J.G.M. Peijnenburg et al., NATO ASI Series, 2. Environment—vol. 23, pp. 93-104, 1996.
Caplus 127:293717, "Optical properties of segmented oligourethane with azomethine terminal fragments," National Academy of Science of Ukraine, M. V. Kurik et al., pp. 2038-2041, 1996, 2 pages.
Caplus 127:34137f, "Preparation of quinoline and quinazoline derivatives inhibiting platelet-derived growth factor receptor autophosphorylation," Kazuo Kuhn et al., May 15, 1997, WO 97/17329.
Capitis 131:58658k, "Inhibition of raf kinase using symmetrical and unsymmetrical substituted diphenyl ureas," Miller, Scott, et al. Jul. 1, 1999, WO 99 32,436.
Caplus 131:73649b, "Preparation of pyrazolyl aryl ureas and related compounds as p38 kinase inhibitors," Jacques Dumas et al., Jul. 1, 1999, WO 99/32110.
Caplus 131:87909y, "inhibition of p38 kinase activity using substituted heterocyclic ureas," Jacques Dumas et al., Jul. 1, 1999, WO 99/32111.
Caplus 146:265643 Abstract of Strumberg et al., "Sorafenib—A novel opportunity in oncology," Arzneimitteltherapie 25(1):2-6 (2007) abstract. 1 page.
Kujundzic et al., "Synthesis of 8-methyl-1,2,3,4-tetrahydropyrido[3,4-*d*] pyrimidine-2,4-diones," Croat. Chem. Acta (1991) 64(4):599-606, Chemical Abstracts vol. 116, No. 21, May 25, 1992, (pp. 741-742) No. 116:214456.
Badran et al., "Novel piperazinyl-substituted pyritnidines as antihypertensive and vasodilators," Revue Roumaine de Chimie (1992), 37(2):238-288, Chemical Abstracts vol. 117:251318.
"Beilstein number" Collection, 28 pp. (1997).
"Beilstein number" Collection, 4 pp. (1997).
Derwent World Patents Index Search, pp. 20-26. (1997).
Dumas, J. "CAS Substructure," May 6, 1997, pp. 1-29.
Scott, Bill, "Substructure (Patent Families)," Aug. 11, 1997, pp. 1-19.
Scott, Bill, "Substructure #2," Nov. 25, 1997, pp. 1-3.
Scott, Bill, "Substructure Search," Dec. 2, 1997, pp. 1-49.
Substructure Search, pp. 1-29. (1997).
Wild, Hanno, "Substructure #1," search, pp. 1-150, 1996.
A "Notice of References Cited" U.S. Appl. No. 08/995,749, filed Dec. 22, 1997, Inhibition of P38 Kinase Using Symmetrical and Unsymmetrical Diphenyl Ureas, 2 pages.
A "Notice of References Cited" U.S. Appl. No. 09/083,399, filed May 22, 1998, Patent 6187799 issued Feb. 13, 2001, Inhibition of Raf Kinase Activity Using Aryl Ureas, 1 page.

(56) References Cited

OTHER PUBLICATIONS

A "Notice of References Cited" U.S. Appl. No. 09/425,228, filed Oct. 22, 1999, Omega-Carboxyaryl Substituted Diphenyl Ureas As Raf Kinase Inhibitors, 3 pages.
A "Notice of References Cited" U.S. Appl. No. 09/425,229, filed Oct. 22, 1999, Omega-Carboxy Aryl Substituted Diphenyl Ureas As p38 Kinase Inhibitors, 1 page.
A "Notice of References Cited" U.S. Appl. No. 09/458,015, filed Dec. 10, 1999, Inhibition of p38 Kinase Using Symmetrical and Unsymmetrical Diphenyl Ureas, 1 page.
A "Notice of References Cited" U.S. Appl. No. 09/472,232, filed Dec. 27, 1999, Patent 7329670 issued Feb. 12, 2008, Inhibition of Raf Kinase Using Aryl and Heteroaryl Substituted Heterocyclic Ureas, 1 page.
A "Notice of References Cited" U.S. Appl. No. 09/773,604, filed Feb. 2, 2001, Publication No. US 2001-0034247-A1, Publication Date Oct. 25, 2001, Omega-carboxyaryl Substituted Diphenyl Ureas as Raf Kinase Inhibitors, 1 page.
A "Notice of References Cited" U.S. Appl. No. 09/773,659, filed Feb. 21, 2001, Publication No. US 2001-0011135 A1, Publication Date: Aug. 2, 2001, Omega-carboxyaryl Substituted Diphenyl Ureas As Raf Kinase Inhibitors, 1 page.
A "Notice of References Cited" U.S. Appl. No. 09/773,672, filed Feb. 2, 2001, Publication No. US 2001-0016659 A1, Publication Date: Aug. 23, 2001, Omega-carboxyaryl substituted Diphenyl Ureas as Raf Kinase Inhibitors, 1 page.
A "Notice of References Cited" U.S. Appl. No. 09/773,675, filed Feb. 2, 2001, Publication No. US 2001-0011136-A1, Publication Date: Aug. 2, 2001, Omega-Carboxyaryl Substituted Diphenyl Ureas as Raf Kinase Inhibitors, 1 page.
A "Notice of References Cited" U.S. Appl. No. 09/776,935, filed Dec. 22, 1998, Inhibition of p38 Kinase Using Aryl and Heteroaryl Substituted Heterocyclic Ureas, 1 page.
A "Notice of References Cited" U.S. Appl. No. 09/776,936, filed Dec. 22, 1998, Inhibition of Raf Kinase Using Symmetrical and Unsymmetrical Substituted Diphenyl Ureas, 1 page.
A "Notice of References Cited" U.S. Appl. No. 09/777,920, filed Feb. 7, 2001, Inhibition of RAF kinase using quinolyl, isoquinolyl or pyridyl ureas, 1 page.
A "Notice of References Cited" U.S. Appl. No. 09/948,915, filed Sep. 10, 2001, Omega-Carboxyaryl Substituted Diphenyl Ureas As Raf Kinase Inhibitors, 1 page.
A "Notice of References Cited" U.S. Appl. No. 10/042,226, filed Jan. 11, 2002, Omega-Carboxyaryl Substituted Diphenyl Ureas As Raf Kinase Inhibitors, 1 page.
Co-pending U.S. Appl. No. 09/458,014, filed Dec. 10, 1999, Dumas et al.
Abandoned U.S. Appl. No. 09/776,935, filed Dec. 22, 1998, Dumas et al.
Co-pending U.S. Appl. No. 09/776,936, filed Dec. 22, 1998, Miller et al.
Issued U.S. Appl. No. 09/889,227, filed Jul. 12, 2000, Riedl et al., issued as 7351834, Apr. 1, 2008.
Co-pending U.S. Appl. No. 09/993,647, filed Nov. 27, 2001, Riedl et al., published as 2003-0181442, Sep. 25, 2003.
Issued U.S. Appl. No. 10/060,396, filed Feb. 1, 2002, Miller et al., patent 7517880, issued Apr. 14, 2009, also published as 2004-0102636, May 27, 2004.
Issued U.S. Appl. No. 10/071,248, filed Feb. 11, 2002, Riedl et al., patent 7528255, issued May 5, 2009, also published as 2003-139605, Jul. 24, 2003.
Abandoned U.S. Appl. No. 10/086,417, filed Mar. 4, 2002, Riedl et al., published as 2003-0105091, Jun. 5, 2003.
Abandoned U.S. Appl. No. 10/125,369, filed Apr. 19, 2002, Dumas et al., published as 2003-0207914, Nov. 6, 2003.
Abandoned U.S. Appl. No. 10/308,187, filed Dec. 3, 2002, Carter et al., published as 2003-0232765, Dec. 18, 2003.
Abandoned U.S. Appl. No. 10/361,844, filed Feb. 11, 2003, Dumas et al., published as 2004-0023961, Feb. 5, 2004.
Abandoned U.S. Appl. No. 10/361,850, filed Feb. 11, 2003, Dumas et al., published s as US 2003-0216396, Nov. 20, 2003.
Co-pending U.S. Appl. No. 10/361,859, filed Feb. 11, 2003, Dumas et al., published as 2003-0216446, Nov. 20, 2003.
Co-Pending U.S. Appl. No. 10/895,985, filed Jul. 22, 2004, Boyer et al., published as US 2005-0038080, Feb. 17, 2005.
Co-Pending U.S. Appl. No. 11/932,548, filed Oct. 31. 2007, Dumas et al.
Co-Pending U.S. Appl. No. 12/084,662, filed May 7, 2008, Sandner et al., published as 2010-0035888, Feb. 11, 2010.
Co-Pending U.S. Appl. No. 12/086,454, filed Jun. 12, 2008, Weber et al.
Co-Pending U.S. Appl. No. 12/093,515, filed Nov. 13, 2008, Wilhelm et al.
Co-Pending U.S. Appl. No. 12/095,611, filed May 30, 2008, Smith et al.
Co-Pending U.S. Appl. No. 12/158,524, filed Jun. 20, 2008, Smith et al.
Co-Pending U.S. Appl. No. 12/294,979, filed Sep. 29, 2008, Wilhelm et al.
Co-Pending U.S. Appl. No. 12/421,690, filed Apr. 10, 2009, Dumas et al.
Co-Pending U.S. Appl. No. 12/444,974, filed Apr. 9, 2009, Grunenberg et al.
Co-Pending U.S. Appl. No. 12/514,129, filed May 8, 2009, Grunenberg et al.
Co-Pending U.S. Appl. No. 12/514,715, filed May 13, 2009, Stiehl et al.
Co-Pending U.S. Appl. No. 12/520,618, filed Jun. 22, 2009, Smith et al.
Co-Pending U.S. Appl. No. 12/520,609, filed Jun. 22, 2009, Smith et al.
Co-pending U.S. Appl. No. 12/523,652, filed Jul. 17, 2009, Wilhelm et al.
Co-pending U.S. Appl. No. 12/523,697, filed Jul. 17, 2009, Wilhelm et al.
Co-Pending U.S. Appl. No. 12/628,735, filed Dec. 1, 2009, Dumas et al.
Co-Pending U.S. Appl. No. 12/692,845, filed Jan. 25, 2010, Dumas et al.
Co-Pending Application PCT/US09/61506, filed Oct. 21, 2009, Carol Pena.
International search report for International Application No. PCT/US98/10375 dated Sep. 3, 1998, Inhibition of p38 Kinase Activity by Aryl Ureas, publication No. 98/52558, publication date Nov. 26, 1998, 1 page.
International search report for International Application No. PCT/US9S/10376 dated Jul. 30, 1998, Raf Kinase Inhibitors, publication No. WO 98/52559, publication date Nov. 26, 1998, 1 page.
International search report for International Application No. PCT/US98/26078 dated Apr. 2, 1999, Inhibition of Raf Kinase Using Substituted Heterocyclic Ureas, publication No. WO 99/32106, publication date Jul. 1, 1999, 2 pages.
International search report for International Application No. PCT/US98/26079 dated Apr. 12, 1999, Inhibition of p38 Kinase Activity Using Aryl and Heteroaryl Substituted Heterocyclic Ureas, publication No. WO 99/32110, publication date Jul. 1, 1999, 1 page.
International search report for International Application No. PCT/US98/26080 dated Apr. 12, 1999, Inhibition of p38 Kinase Using Substituted Heterocyclic Ureas, publication No. WO 99/32111, publication date Jul. 1, 1999, 1 page.
International search report for International Application No. PCT/US98/26081 dated Apr. 2, 1999, Inhibition of Raf Kinase Using Symmetrical and Unsymmetrical Substituted Diphenyl Ureas, publication No. WO 99/32436, publication date Jul. 1, 1999, 1 page.
International search report for International Application No. PCT/US98/26082 dated May 12, 1999, Inhibition of Raf Kinase Using Aryl and Heteroaryl Substituted Heterocyclic Ureas, publication No. WO 99/32455, publication date Jul. 1, 1999, 1 page.
International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.

(56) References Cited

OTHER PUBLICATIONS

International search report for International Application No. PCT/US00/00648 dated Jun. 29, 2000, Omega-Carboxyaryl Substituted Diphenyl Ureas as RAF Kinase Inhibitors, publication No. WO 00/42012 A1, publication date Jul. 20, 2000, 2 pages.
International search report for International Application No. PCT/US00/00768 dated May 16, 2000, Omega-Carboxy Aryl Substituted Diphenyl Ureas as p38 Kinase Inhibitors, publication No. WO 00/41698 A1, publication date Jul. 20, 2000, 1 page.
International search report for International Application No. PCT/US02/12064 dated Sep. 20, 2002, Heteroaryl Ureas Containing Nitrogen Hetero-Atoms as p38 Kinase Inhibitors, publication No. 02/085859, publication date Oct. 31, 2002, 2 pages.
International search report for International Application No. PCT/US02/12066 dated Sep. 27, 2002, Inhibition of Raf Kinase Quinolyl, Isoquinolyl or Pyridyl Ureas, publication No. 02/085857, publication date Oct. 31, 2002, 2 pages.
Supplemental search report from the EPO for European application EP 98963809.3 dated Mar. 30, 2001, Inhibition of Raf Kinase Using Symmetrical and Unsymmetrical Substituted Diphenyl Ureas, publication No. 1049664, publication date Jul. 1, 1999, granted Mar. 16, 2005, 4 pages.
Supplemental search report from the EPO for European application EP 98963810.1 dated Dec. 21, 2000, Inhibition of Raf Kinase Using Aryl and Heteroaryl Substituted Heterocyclic Ureas, publication No. 1056725, publication date Jul. 1, 1999, granted Jun. 7, 2006, 4 pages.
Supplemental search report from the EPO for European application EP 98965981.8 dated Dec. 21, 2000, Inhibition of Raf Kinase Using Substituted Heterocyclic Ureas, publication No. 1047418, publication date Jul. 1, 1999, granted Jul. 27, 2005, 8 pages.
Supplemental search report from the EPO for European application EP 00903239.2 dated Aug. 7, 2002, Omega-Carboxyaryl Substituted Diphenyl Ureas as Raf Kinase inhibitors, publication No. EP 1140840, published Jul. 20, 2000, granted Mar. 22, 2006, 6 pages.
Supplemental search report from the EPO for European application EP 00905597.1 dated Feb. 7, 2008, Omega-Carboxyaryl Substituted Diphenyl Ureas As p38 Kinase Inhibitors, publication No. EP 1158985, Jul. 20, 2000, 9 pages.
Belgore et al., "Measurement of free and complexed soluble vascular endothelial growth factor receptor, Flt-1, in fluid samples: development and application of two new immunoassays," Clinical Science, 100: 567-575 (2001).
Belgore et al., "Plasma levels of Vascular Endothelial Growth Factor (VEGF) and Its Receptor, Flt-1, in Haematological Cancers: A Comparison With Breast Cancer," American Journal of Hematology, 66:59-61 (2001).
Coskun et al., "Significance of serum vascular endothelial growth factor, insulin-like growth factor-I levels and nitric oxide activity in breast cancer patients," The Breast, 12, 104-110 (2003).
Kaya et al., "The prognostic significance of vascular endothelial growth factor levels in sera of non-small cell lung cancer patients," Respiratory Medicine, 98:632-636 (2004).
Kumar et al., "Soluble FLT-1 is Detectable in the Sera of Colorectal and Breast Cancer Patients," Anticancer Research, 22:1877-1880 (2002).
Pasieka et al., "Evaluation of the Levels of bFGF, VEGF, sICAM-1, and sVCAM-1 in Serum of Patients with Thyroid Cancer," Recent Results in Cancer Research, 162:189-194 (2003).
Pegram et al., "Combined Biological Therapy of Breast Cancer Using Monoclonal Antibodies Directed Against HER2/*neu* Protein and Vascular Endothelial Growth Factor," Seminars in Oncology, 29(Suppl. 11):29-37 (2002).

Poon et al., "Prognostic significance of serum vascular endothelial growth factor an endostatin in patients with hepatocellular carcinoma," British Journal of Surgery, 91:1354-1360 (2004).
Ria et al., "Serum levels of angiogenic cytokines decrease after antineoplastic radiotherapy," Cancer Letters, 216:103-107 (2004).
Secord et al., "The relationship between serum vascular endothelial growth factor, persistent disease, and survival at second—look laparotomy in ovarian cancer," Gynecologic Oncology, 94:74-79 (2004).
English abstract of JP 10-306078, Nov. 17, 1998, Patent Abstracts of Japan, 2 pages.
English abstract of JP 08-301841, Nov. 19, 1996, Patent Abstracts of Japan, 2 pages.
English abstract of JP 03-198049, Aug. 29, 1991, Patent Abstracts of Japan, 1 page.
English abstract of JP 03-144634, Jun. 20, 1991, Patent Abstracts of Japan, 1 page.
English abstract of JP 03-053247, Mar. 7, 1991, Patent Abstracts of Japan, 1 page.
English abstract of JP 02-150840, Jun. 11, 1990, Patent Abstracts of Japan, 1 page.
English abstract of JP 02-108048, Apr. 19, 1990, Patent Abstracts of Japan, 1 page.
English abstract of JP 02-105146, Apr. 17, 1990, Patent Abstracts of Japan, 1 page.
English abstract of JP 02-035450, Feb. 6, 1990, Patent Abstracts of Japan, 1 page.
English abstract of JP 01-200254, Aug. 11, 1989, Patent Abstracts of Japan, 1 page.
English abstract of JP 01-259360, Oct. 17, 1989, Patent Abstracts of Japan, 2 pages.
English abstract of JP 01-102461, Apr. 20, 1989, Patent Abstracts of Japan, 1 page.
English abstract of JP 06-120039, Apr. 28, 1994, Patent Abstracts of Japan, 1 page.
English abstract of JP 05-180862, Jul. 23, 1993, Patent Absnacts of Japan, 1 page.
English abstract of JP 05-163170, Jun. 29, 1993, Patent Abstracts of Japan, 1 page.
English abstract of JP 05-077375, Mar. 30, 1993, Patent Abstracts of Japan, 1 page.
English abstract of JP 05-076072, Mar. 26, 1993, Patent Absnacts of Japan, 2 pages.
English abstract of JP 50-149668 A and JP 56-29871 B, Derwent World Patents Index, Dialog File No. 351, Acc. No. 1488399, 3 pages.
English abstract of JP 53-086033, Jul. 29, 1978, Patent Abstracts of Japan, 1 page.
English abstract of JP 54-032468, Mar. 9, 1979, Patent Abstracts of Japan, 1 page.
English abstract of JP 55-098152, Jul. 25, 1980, Patent Abstracts of Japan, 1 page.
English abstract of JP 64-009455, Jan. 12, 1989, Patent Abstracts of Japan, 1 page.
English abstract of JP 02-023337, Mar. 9, 1979, Patent Abstracts of Japan, 2 pages.
English abstract of EPA 0379915/EP-A1, Aug. 1, 1990, 2 pages.
English abstract of DD 253997 A, Feb. 10, 1988, 1 page.
English abstract of DE511468, European Patent Office, 2 pages.
Co-Pending U.S. Appl. No. 12/619,913, filed Nov. 17, 2009, Ranges et al.

* cited by examiner

DIARYL UREAS FOR DISEASES MEDIATED BY PDGFR

This application claims the benefit of U.S. Provisional Application Nos. 60/556,062, filed Mar. 25, 2004, 60/520, 399, filed Nov. 17, 2003, and 60/471,735, filed May 20, 2003, each of which are hereby incorporated by reference in their entirety.

BACKGROUND OF THE INVENTION

One of the key regulators of stromal formation is the platelet-derived growth factor, also called PDGF. PDGF was originally identified as the v-sis oncogene product of the simian sarcoma virus (Heldin, C. H., et al., *J Cell Sci Suppl*, 1985, 3, 65-76). This growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta*, 1998. 1378(1), 79-113). PDGFR is found as homo- or heterodimer chains which have 30% homology overall in their amino acid sequence and 64% homology between their kinase domains (Heldin, C. H., et al. *Embo J*, 1988, 7(5), 1387-93). PDGFR is a member of a family of tyrosine kinase receptor with split kinase domains that includes VEGFR2 (KDR), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry*, 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, the major function of PDGF is to facilitate and increase the rate of wound healing and to maintain blood vessel homeostasis (Baker, E. A. and D. J. Leaper, *Wound Repair Regen*, 2000. 8(5), 392-8; Yu, J., A. Moon, and H. R. Kim, *Biochem Biophys Res Commun*, 2001. 282(3), 697-700). PDGF is found at high concentrations in platelets and is a potent chemoattractant for fibroblast, smooth muscle cells, neutrophils and macrophages. In addition to its role in wound healing PDGF helps maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis, PDGF controls interstitial fluid pressure, regulating the permeability of vessels through its regulation of the interaction between connective tissue cells and the extracellular matrix.

The PDGFR family of ligands is a set of homo- and heterodimeric ligands bound through a disulfide bridge that can be found in three forms, AA, AB and BB. PDGF is a potent mitogen and chemotactic factor for a variety of mesenchymal cells, such as fibroblasts, vascular smooth muscle cells, glomerular mesangial cells and brain glial cells. PDGF has been implicated in a variety of pathological conditions, including cancer, atherosclerosis, restenosis, liver cirrhosis, pulmonary fibrosis, and glomerulonephritis. PDGF exerts its biological activity by binding to the PDGF receptor (PDGFR) inducing receptor dimerization. PDGF-AA induces only α/α receptor dimers, PDGF-AB induces α/α and α/β receptor dimers, and PDGF-BB induces all three receptor dimer combinations. Once dimerized, the PDGFR undergoes trans-phosphorylation on a tyrosine, activating it for intracellular signaling interactions essential that mediate changes in gene expression, cell migration and proliferation.

Following vascular injury the restenotic reparative process is engaged, and within a few days damaged and dying vascular smooth muscle cells (vSMC) release growth factors, such as bFGF, inducing medial vSMC proliferation over the next 3-5 days. The vSMC migrate to the neointima, where approximately half undergo cell cycle proliferation in the intima, and the other half do not divide. PDGF-BB may be a central chemotactic factor involved in wound healing following vascular trauma because it is both mitogenic for cultured vSCM through activation of PDGF receptors, and chemotactic through activation of PDGFRβ. In vivo, PDGF-BB acts predominantly as a chemotactic factor on vSMC. Injection of PDGF-BB has been shown to increase vSMC migration by greater than 10-fold, but proliferation by only 2-fold (A. Jawein et al. *J. Clin. Invest.* 1992, 89, 507). In addition, anti-PDGF antibodies have been shown to block migration of vSMC, but not their proliferation (G. A. A. Ferns *Science* 1991, 253, 1129). The PDGFR inhibitor RPR101511A prevented angiographically defined restenosis following angioplasty (G. Bilder et al. *Circulation* 1999, 99, 3292). Similarly, the PDGFR inhibitor CT52923 was shown to inhibit neointima formation following carotid artery injury in the rat in in vivo studies (J.-C. Yu et al. *J. Pharmacol. Exp. Therap.* 2001, 298, 1172).

Signal transduction through PDGFR has been linked to vascular smooth muscle cell (vSMC) migration and proliferation leading to allograft vasculopathy and ultimately graft rejection. The PDGFR inhibitor AG-1295 was shown to reduce neointimal formation in aortic allograft vasculopathy in a rat model of neointimal formation (M. Karck et al. *Transplantation* 2002, 74, 1335).

Despite the biological evidence that PDGFR inhibitors known in the art have the potential to be used in medicines, there remains a need for new inhibitors of this receptor tyrosine kinase.

Diarylureas are a class of serine-threonine kinase inhibitors as well as tyrosine kinase inhibitors well known in the art. The following publications illustrate their utility as an active ingredient in pharmaceutical compositions for the treatment of cancer, angiogenesis disorders, and inflammatory disorders:

Redman et al., *Bioorg. Med. Chem. Lett.* 2001, 11, 9-12.
Smith et al., *Bioorg. Med. Chem. Lett.* 2001, 11, 2775-2778.
Dumas et al., *Bioorg. Med. Chem. Lett.* 2000, 10, 2047-2050.
Dumas et al., *Bioorg. Med. Chem. Lett.* 2000, 10, 2051-2054.
Ranges et al., *Book of Abstracts, 220th ACS National Meeting, Washington, D.C., USA, MEDI* 149.
Dumas et al., *Bioorg. Med. Chem. Lett.* 2002, 12, 1559-1562.
Lowinger et al., *Clin. Cancer Res.* 2000, 6(suppl.), 335.
Lyons et al., *Endocr.-Relat. Cancer* 2001, 8, 219-225.
Riedl et al., *Book of Abstracts, 92nd AACR Meeting, New Orleans, La., USA, abstract* 4956.

Khire et al., *Book of Abstracts*, 93rd AACR Meeting, San Francisco, Calif., USA, abstract 4211.
Lowinger et al., *Curr. Pharm. Design* 2002, 8, 99-110.
Regan et al., *J. Med. Chem.* 2002, 45, 2994-3008.
Pargellis et al., *Nature Struct. Biol.* 2002, 9(4), 268-272.
Carter et al., *Book of Abstracts*, 92nd AACR Meeting, New Orleans, La., USA, abstract 4954.
Vincent et al., *Book of Abstracts*, 38th ASCO Meeting, Orlando, Fla., USA, abstract 1900.
Hilger et al., *Book of Abstracts*, 38th ASCO Meeting, Orlando, Fla., USA, abstract 1916.
Moore et al., *Book of Abstracts*, 38th ASCO Meeting, Orlando, Fla., USA, abstract 1816.
Strumberg et al., *Book of Abstracts*, 38th ASCO Meeting, Orlando, Fla., USA, abstract 121.
Madwed J B: *Book of Abstracts, Protein Kinases: Novel Target Identification and Validation for Therapeutic Development*, San Diego, Calif., USA, March 2002.
Roberts et al., *Book of Abstracts*, 38th ASCO Meeting, Orlando, Fla., USA, abstract 473.
Tolcher et al., *Book of Abstracts*, 38th ASCO Meeting, Orlando, Fla., USA, abstract 334.
Karp et al., *Book of Abstracts*, 38th AACR Meeting, San Francisco, Calif., USA, abstract 2753.

DESCRIPTION OF THE INVENTION

The present invention provides methods for treating, ameliorating, preventing, modulating, etc., conditions and diseases in humans and other mammals that are associated with and/or mediated by signal transduction pathways comprising platelet-derived growth factor receptor (PDGFR). Methods of the present invention especially provide for modulating diseases and conditions associated and/or mediated by PDGFR-beta.

In particular, the present invention provides devices (e.g., stents and other materials in contact with blood and/or cells), compositions, and methods for treating, ameliorating, preventing, or modulating restenosis following angioplastic surgery or other invasive procedures that affect the vascular system, and graft rejection following transplantation of a donor tissue into a host. The methods can comprise, e.g., administering an aryl urea compound as described below, pharmaceutically-acceptable salts thereof, and prodrugs thereof.

The compounds of the present invention can be utilized to treat any conditions or diseases mediated by PDGFR-beta, including any unwanted and/or deleterious consequence of an invasive procedures performed on the body, especially to the vascular system, including, but not limited to, angioplasty, atherectomy, arterial grafting, vessel wall stenting, and endarterectomy. The compounds can be applied directly to the affected area (e.g., in combination with a material or carrier designed to release the compound) or on a device or material that is introduced into the target site.

The aryl urea compounds employed in the methods of this invention comprise compounds of Formula I, pharmaceutically acceptable salts thereof, prodrugs thereof, and any active derivatives thereof, which are collectively referred to herein as the "compounds of the invention" and the like. Formula I is as follows:

A-NH—C(O)—NH—B-L-M-Q (I)

wherein

A is phenyl, optionally substituted with 1-3 substituents independently selected from the group consisting of $C_1$-$C_5$ alkyl, $C_1$-$C_5$ halogenoalkyl, up to perhaloalkyl, $C_1$-$C_5$ alkoxy, halogen, cyano, and nitro;

Alternatively, A is a group of the formula:

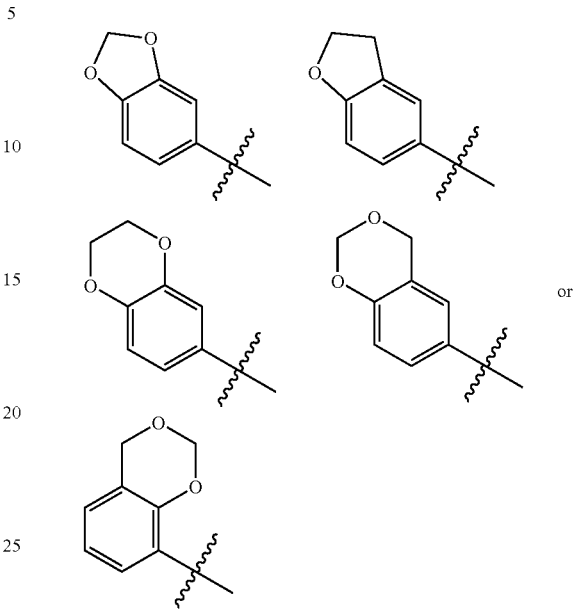

optionally substituted with 1-6 substituents selected from $C_1$-$C_5$ alkyl and halogen;

B is phenylene or naphthylene, optionally substituted with 1-3 substituents independently selected from the group consisting of $C_1$-$C_5$ alkyl, $C_1$-$C_5$ halogenoalkyl, up to perhaloalkyl, $C_1$-$C_5$ alkoxy, halogen, cyano, and nitro;

L is a linker selected from —O— or —S—;

M is a pyridine ring, optionally substituted with $C_1$-$C_5$ alkyl, $C_1$-$C_5$ halogenoalkyl, up to perhaloalkyl, $C_1$-$C_5$ alkoxy, halogen, and hydroxy; and Q is cyano, —C(O)—$R_1$, or —C(O)—$NR_1R_2$, where $R_1$ and $R_2$ are independently selected from H or lower alkyl.

Suitable $C_1$-$C_5$ alkyl groups include methyl, ethyl, propyl, butyl, and pentyl, as well as branched isomers such as isopropyl, isobutyl, sec-butyl, tert-butyl, etc. The term "$C_1$-$C_5$ alkoxy" means a straight or branched chain alkoxy group having saturated carbon atoms which may be linear or branched with single or multiple branching, and includes such groups as methoxy, ethoxy, n-propoxy, isopropoxy, and the like. It also includes halogenated groups such as 2,2-dichloroethoxy, trifluoromethoxy, and the like.

Suitable halogens include F, Cl, Br, and/or I, from one to per-substitution (i.e. all H atoms on a group replaced by a halogen atom) being possible where an alkyl group is substituted by halogen, mixed substitution of halogen atom types also being possible on a given moiety. Preferred halogens are Cl, Br and F.

The term "$C_1$-$C_5$ halogenoalkyl, up to perhaloalkyl" includes alkyl groups having one or more alkyl hydrogens replaced with halogen, and alkyl groups having all alkyl hydrogens replaced by halogen. Examples include chloromethyl, dichloromethyl, trichloromethyl, fluoromethyl, difluoromethyl, trifluoromethyl, and the like.

When any moiety is "substituted," it can have up to the highest number of indicated substituents, and each substituent can be located at any available position on the moiety and can be attached through any available atom on the substituent. "Any available position" means any position on the moiety that is chemically accessible through means known in the art or taught herein and that does not create an unduly unstable molecule. When there are two or more substituents on any moiety, each substituent is defined independently of any other substituent and can, accordingly, be the same or different. The term "optionally substituted" means that the moiety so modified may be either unsubstituted, or substituted with the identified substituent(s).

It is understood that since M is pyridine, the term "hydroxy" as an optional pyridine substituent includes 2-, 3-, and 4-hydroxypyridine, but also includes those structures referred to in the art as 1-oxopyridine, 1-hydroxypyridine and pyridine N-oxide.

Where the plural form of the word compounds, salts, and the like, is used herein, this is taken to mean also a single compound, salt, or the like.

Compounds of the invention of particular interest include those of Formula I wherein B is phenylene, optionally substituted with halogen.

Compounds of the invention of particular interest also include those of Formula I wherein L is —O—.

Compounds of the invention of particular interest also include those of Formula I wherein A is phenyl, substituted with 1-3 substituents selected from the group consisting of $C_1$-$C_5$ alkyl, $C_1$-$C_5$ halogenoalkyl, up to perhaloalkyl, $C_1$-$C_5$ alkoxy, and halogen, or A is a group of the formula:

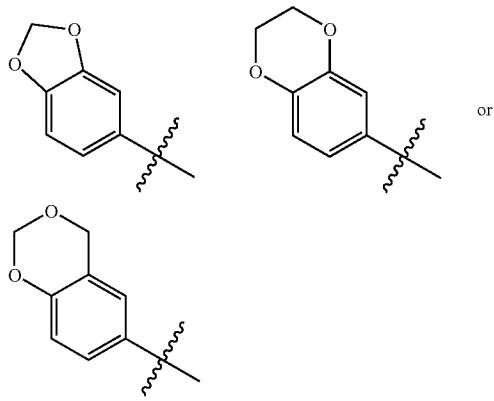

optionally substituted with 1-6 halogen atoms.

Compounds of the invention of particular interest also include those of Formula I wherein:
A is 4-chloro-3-trifluoromethylphenyl, 4-fluoro-3-trifluoromethylphenyl, 4-bromo-3-trifluoromethylphenyl, or 2,2,4,4-tetrafluoro-4H-benzo[1,3]dioxin-6-yl;
B is phenylene, chlorophenylene or fluorophenylene;
L is —O—;
M is pyridine or 1-hydroxypyridine; and
Q is cyano, C(O)—$NH_2$, or C(O)—NHMe.

Compounds of the invention of particular interest also include those selected from:
N-(4-chloro-3-(trifluoromethyl)phenyl)-N'-(4-(2-(N-methylcarbamoyl)-4-pyridyl oxy)phenyl) urea,
N-(4-bromo-3-(trifluoromethyl)phenyl)-N'-(4-(2-(N-methylcarbamoyl)-4-pyridyl oxy)phenyl) urea,
N-(4-bromo-3-(trifluoromethyl)phenyl)-N'-(4-(2-(N-methylcarbamoyl)-4-pyridyl oxy)-2-chlorophenyl) urea,
N-(4-chloro-3-(trifluoromethyl)phenyl)-N'-(4-(2-carbamoyl-4-pyridyloxy)phenyl) urea,
N-(4-chloro-3-(trifluoromethyl)phenyl)-N'-(4-(1-hydroxy-2-carbamoyl-4-pyridyl oxy)phenyl) urea,
N-(4-chloro-3-(trifluoromethyl)phenyl)-N'-(4-(1-hydroxy-2-(N-methylcarbamoyl)-4-pyridyl oxy)phenyl) urea,
N-(4-chloro-3-(trifluoromethyl)phenyl)-N'-(4-(2-(N-methylcarbamoyl)-4-pyridyl oxy)-2-fluorophenyl) urea,
N-(4-bromo-3-(trifluoromethyl)phenyl)-N'-(4-(2-(N-methylcarbamoyl)-4-pyridyl oxy)-2-fluorophenyl) urea,
N-(4-fluoro-3-(trifluoromethyl)phenyl)-N'-(4-(2-(N-methylcarbamoyl)-4-pyridyl oxy)-2-fluorophenyl) urea,
N-(4-chloro-3-(trifluoromethyl)phenyl)-N'-(4-(2-(N-methylcarbamoyl)-4-pyridyl oxy)-2-chlorophenyl) urea,
N-(6-(2,2,4,4-tetrafluoro-4H-benzo[1,3]dioxinyl))-N'-(4-(2-cyano-4-pyridyloxy)phenyl) urea, and
N-(6-(2,2,4,4-tetrafluoro-4H-benzo[1,3]dioxinyl))-N'-(4-(2-cyano-4-pyridyloxy)-2-fluorophenyl) urea.

Compounds of the present invention can exist in different geometrical isomeric forms. All such configurations (including enantiomers and diastereomers), are included within the scope of the present invention. A number of the compounds of Formula I possess asymmetric centers, depending on the location a nature of various substituents. These compounds can therefore exist in racemic and optically active forms as well as in the form of racemic or non-racemic mixtures thereof, and in the form of diastereomers and diastereomeric mixtures. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. All of these compounds, including cis isomers, trans isomers, diastereomic mixtures, racemates, non-racemic mixtures of enantiomers, substantially pure, and pure enantiomers, are considered to be within the scope of the compounds of this invention and are collectively referred to when reference is made to compounds of this invention. Therefore, the methods of the present invention encompass the use of any isolated racemic or optically active form of compounds described in Formula I which possess PDGFR inhibitory activity.

Methods of separation of enantiomeric and diastereomeric mixtures are well known to one skilled in the art. The optical isomers may be obtained by resolution of the racemic mixtures according to conventional processes, for example, by the formation of diastereoisomeric salts using an optically active acid or base. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical chemical differences by methods known to those skilled in the art, for example, by chromatography or fractional crystallization. The optically active bases or acids are liberated from the separated diastereomeric salts.

Another process for separation of optical isomers involves the use of a chiral chromatography column (e.g., chiral HPLC columns) optimally chosen to maximize the separation of the enantiomers. Suitable chiral HPLC columns are manufactured by Diacel, e.g., Chiracel OD and Chiracel OJ. The optically active compounds of Formula (I) can likewise be obtained by utilizing optically active starting materials. The present invention encompasses any separated, isolated, pure or partially purified isomers or racemic mixtures of the compounds of formula I which possess PDGFR inhibitory activity, and/or an efficacy in modulating any of the diseases and/or conditions mentioned herein. The term stereoisomer is understood to encompass diastereoisomers, enantiomers, geometric isomers, etc.

Preferred compounds are those with the absolute configuration of the compound of Formula I which produce the more desirable biological activity are also included within the scope of the present invention. The purification of said isomers and the separation of said isomeric mixtures can be accomplished by standard techniques known in the art. The phrase "substantially pure enantiomers" means that no more than about 5% w/w of the corresponding opposite enantiomer is present.

Pharmaceutically-acceptable salts of these compounds, as well as commonly used prodrugs of these compounds, are also within the scope of the invention. The term "pharmaceutically acceptable salt" refers to a relatively non-toxic, inorganic, or organic acid addition salt of a compound of the present invention. For example, see S. M. Berge, et al. "Pharmaceutical Salts," *J. Pharm. Sci.* 1977, 66, 1-19.

Suitable salts are especially the pharmaceutically acceptable salts of compounds of formula (I) or such as, for example, organic or inorganic acid addition salts of compounds of formula (I). Suitable acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate. Suitable inorganic acids include but are not limited to halogen acids (such as hydrochloric acid and hydrobromic acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, trifluoroacetic acid, dodecanoic acid, glycolic acid, lactic acid, 2- or 3-hydroxybutyric acid, γ-aminobutyric acid (GABA), gluconic acid, glucosemonocarboxylic acid, benzoic acid, salicylic acid, phenylacetic acid and mandelic acid, fumaric acid, succinic acid, adipic acid, pimelic acid, suberic acid, azeiaic acid, maleic acid, tartaric acid, citric acid, glucaric acid, galactaric acid, amino acids (such as glutamic acid, aspartic acid, N-methylglycine, acetytaminoacetic acid, N-acetylasparagine or N-acetylcysteine), pyruvic acid, acetoacetic acid, methanesulfonic acid, trifluoromethanesulfonic acid, 4-toluene sulfonic acid, benzenesulfonic acid, 1-naphthalenesulfonic acid, 2-naphthalenesulfonic acid, phosphoserine, and 2- or 3-glycerophosphoric acid.

In addition, pharmaceutically acceptable salts include acid salts of inorganic bases, such as salts containing alkaline cations (e.g., $Li^+$, $Na^+$, or $K^+$), alkaline earth cations (e.g., $Mg^{+2}$, $Ca^{+2}$, or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The formation of prodrugs is well known in the art in order to enhance the properties of the parent compound; such properties include solubility, absorption, biostability and release time (see "*Pharmaceutical Dosage Form and Drug Delivery Systems*" (Sixth Edition), edited by Ansel et al., published by Williams & Wilkins, pages 27-29, (1995) which is hereby incorporated by reference). Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see *Goodman and Gilman's The Pharmacological Basis of Therapeutics* (Ninth Edition), editor Molinoff et al., pub. by McGraw-Hill, pages 11-13, (1996), which is hereby incorporated by reference).

The potent inhibitory activity of N-[4-chloro-3-(trifluoromethyl)phenyl]-N'-{4-[2-N-methylcarbamoyl-4-pyridyloxy]phenyl} urea, a compound of the present invention, as well as several of its analogs described herein, has been demonstrated in in vitro (biochemical) and in vivo (cellular) assays of PDGFR activity.

While not wishing to be bound by any theory or mechanism of action, it has been found that compounds of the present invention possess the ability to modulate PDGFR kinase activity. The methods of the present invention, however, are not limited to any particular mechanism or how the compounds achieve their therapeutic effect. By the term "modulate," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), etc.

Kinase activity can be determined routinely using conventional assay methods. Kinase assays typically comprise the kinase enzyme, substrates, buffers, and components of a detection system. A typical kinase assay involves the reaction of a protein kinase with a peptide substrate and an ATP, such as $^{32}$P-ATP, to produce a phosphorylated end-product (for instance, a phosphoprotein when a peptide substrate is used. The resulting end-product can be detected using any suitable method. When radioactive ATP is utilized, a radioactively labeled phosphoprotein can be separated from the unreacted gamma-32P-ATP using an affinity membrane or gel electrophoresis, and then visualized on the gel using autoradiography or detected with a scintillation counter. Non-radioactive methods can also be used. Methods can utilize an antibody that recognizes the phosphorylated substrate, e.g., an antiphosphotyrosine antibody. For instance, kinase enzyme can be incubated with a substrate in the presence of ATP and kinase buffer under conditions that are effective for the enzyme to phosphorylate the substrate. The reaction mixture can be separated, e.g., electrophoretically, and then phosphorylation of the substrate can be measured, e.g., by Western blotting using an anti-phosphotyrosine antibody. The antibody can be labeled with a detectable label, e.g., an enzyme, such as HRP, avidin or biotin, chemiluminescent reagents, etc. Other methods can utilize ELISA formats, affinity membrane separation, fluorescence polarization assays, luminescent assays, etc.

An alternative to a radioactive format is time-resolved fluorescence resonance energy transfer (TR-FRET). This method follows the standard kinase reaction, where a substrate, e.g., biotinylated poly(GluTyr), is phosphorylated by a protein kinase in the presence of ATP. The end-product can then detected with a europium chelate phosphospecific antibody (anti-phosphotyrosine or phosphoserine/threonine), and streptavidin-APC, which binds the biotinylated substrate. These two components are brought together spatially upon binding, and energy transfer from the phosphospecific antibody to the acceptor (SA-APC) produces fluorescent readout in the homogeneous format.

The compounds of the present invention can be used to treat and/or prevent any disease or condition mediated by signal transduction pathways comprising platelet-derived growth factor receptor (PDGFR). A disease or condition "mediated" by PDGFR indicates that receptor is a part of a signal transduction pathway that is involved in any aspect of the disease phenotype (e.g., where a defect in the receptor itself is involved in "causing" the disease; where stimulation of the receptor by its ligand induces cell motility, migration, and/or proliferation that produces a disease phenotype; where receptor stimulation or phosphorylation results in restenosis; any functional activity of PDGFR that, when inappropriately expressed, results in a disease symptom and/or phenotype). The term "treating" is used conventionally, e.g., the management or care of a subject for the purpose of combating, alleviating, reducing, relieving, improving the condition of, etc., of a disease or disorder. Diseases and conditions that can be treated include, but are not limited to the prevention of restenosis and graft rejection.

The following patents and publication relate to PDGF/PDGFR inhibition and are incorporated herein for their description of the disease states mediated by PDGFR-beta and assays to determine such activity.

| | |
|---|---|
| U.S. Pat. No. 5,094,941 | Hart, et al. |
| U.S. Pat. No. 5,371,205 | Kelly, et al. |
| U.S. Pat. No. 5,418,135 | Pang |
| U.S. Pat. No. 5,444,151 | Vassbotn, et al. |
| U.S. Pat. No. 5,468,468 | LaRochelle, et al. |
| U.S. Pat. No. 5,567,584 | Sledziewski, et al. |
| U.S. Pat. No. 5,618,678 | Kelly, et al. |
| U.S. Pat. No. 5,620,687 | Hart, et al. |
| U.S. Pat. No. 5,648,076 | Ross, et al. |
| U.S. Pat. No. 5,668,264 | Janjic, et al. |
| U.S. Pat. No. 5,686,572 | Wolf, et al. |
| U.S. Pat. No. 5,817,310 | Ramakrishnan, et al. |
| U.S. Pat. No. 5,833,986 | LaRochelle, et al. |
| U.S. Pat. No. 5,863,739 | LaRochelle, et al. |
| U.S. Pat. No. 5,872,218 | Wolf, et al. |
| U.S. Pat. No. 5,882,644 | Chang, et al. |
| U.S. Pat. No. 5,891,652 | Wolf, et al. |
| U.S. Pat. No. 5,976,534 | Hart, et al. |
| U.S. Pat. No. 5,990,141 | Hirth, et al. |
| U.S. Pat. No. 6,022,854 | Shuman |
| U.S. Pat. No. 6,043,211 | Williams, et al. |
| U.S. Pat. No. 6,110,737 | Escobedo, et al. |
| U.S. Pat. No. 6,207,816B1 | Gold, et al. |
| U.S. Pat. No. 6,228,600B1 | Matsui, et al. |
| U.S. Pat. No. 6,229,002B1 | Janjic, et al. |
| U.S. Pat. No. 6,316,603B1 | McTigue, et al. |
| U.S. Pat. No. 6,372,438B1 | Williams, et al. |
| U.S. Pat. No. 6,403,769B1 | La Rochelle, et al. |
| U.S. Pat. No. 6,440,445B1 | Nowak, et al. |
| U.S. Pat. No. 6,475,782B1 | Escobedo, et al. |
| WO02/083849 | Rosen, et al. |
| WO02/083704 | Rosen, et al. |
| WO02/081520 | Boesen, et al. |
| WO02/079498 | Thomas, et al. |
| WO02/070008 | Rockwell, et al. |
| WO099/59636 | Sato, et al. |
| WO099/46364 | Cao, et al. |
| WO099/40118 | Hanai, et al. |
| WO99/31238 | Yabana, et al. |
| WO99/29861 | Klagsbrun, et al. |
| WO98/58053 | Kendall, et al. |
| WO98/51344 | Maini, et al. |
| WO98/33917 | Alitalo, et al. |
| WO98/31794 | Matsumoto, et al. |
| WO98/16551 | Ferrara, et al. |
| WO98/13071 | Kendall, et al. |
| WO98/11223 | Martiny-Baron, et al. |
| WO97/44453 | Chen, et al. |
| WO97/23510 | Plouet, et al. |
| WO9715662 | Stinchcomb, et al. |
| WO97/08313 | Ferrara, et al. |
| WO96/39515 | Cao, et al. |
| WO96/23065 | Smith, et al. |
| WO96/06641 | Fleurbaaij, et al. |
| WO95/24473 | Cao, et al. |
| WO98/22316 | Kyowa |
| WO95/21868 | Rockwell, et al. |
| WO02/060489 | Xia, et al. |
| PDGFR-beta | |
| EP0869177 | Matsui, et al. |
| WO090/10013 | Matsui, et al. |
| WO97/37029 | Matsui, et al. |
| PDGFR-alpha | |
| EP1000617 | Lammers, et al. |
| EP0869177 | Matsui, et al. |
| EP0811685 | Escobedo, et al. |

PDGFR-beta mediated diseases include, e.g., diseases or conditions characterized by cell proliferation, cell matrix production, cell movement, and/or extracellular matrix production. Specific examples, include, e.g., tumors, malignancies, cancer, metastasis, chronic myeloid leukemia, inflammation, renal disease, diabetic nephropathy, mesangial proliferative glomerulonephritis, fibrotic conditions, atherosclerosis, restenosis, hypertension-related arterosclerosis, venous bypass graft arterosclerosis, scleroderma, interstitial pulmonary diseases, synovial disorders, arthritis, leukemias, lymphomas, etc.

Devices and Other Materials Comprising Compounds

The present invention also relates to devices and other blood and cell contacting materials, such as vascular grafts, cardiac valves, stents, and catheters, which comprise compounds of the present invention.

Percutaneous transluminal coronary angioplasty (PTCA) is widely used to treat patients with coronary artery disease. PTCA can relieve myocardial ischemia in patients with coronary artery disease by reducing lumen obstruction and improving coronary flow. However, stenosis following PTCA is a significant problem, with about 25% to 35% of the patients developing restenosis within 1 to 3 months. Stents (e.g., a metal tube or scaffold) and other devices have been used to address the complications associated with PTCA. Although the rates of restenosis have been lowered, many patients still experienced re-blocking of the arteries, requiring repeat procedures. To confront these problems, stents have been coated with a variety of different materials and active agents to interrupt the biological processes that cause restenosis. Accordingly, the present invention provides an implantable medical device, such as a stent or graft, which comprises one or more compounds of the present invention.

Stents are scaffoldings, typically cylindrical or tubular in shape, which are inserted into an anatomical channel to physically hold it open, and if desired, to expand the walls of the channel. Stents can be crimped on to balloon catheters for insertion through small cavities, positioned in a desired location, and then expanded to a larger diameter. Stents can be either balloon expandable or self-expanding.

Grafts are typically placed in a blood vessel to either replace a diseased segment that has been removed, or to form a bypass conduit through a damaged segment of the vessel wall as is the case with an aneurysm, for example. The graft has a tubular portion that spans the site of the damaged tissue and through which the blood flows. The graft has sections at both ends of the tube that are used to secure the graft to the inside of a vessel wall. The graft also has an outer surface, portions of which are in contact with an inner surface of the blood vessel wall, and an inner surface in contact with the blood flowing through the vessel.

Stents can be of any design or shape that is useful for the desired purpose. For example, stents can be balloon expandable, self-expanding, tube, wire, sheet, ribbon, coil, helical spiral, woven, comprising individual rings, comprising sequential rings, closed cell, open cell, spiral articulated slotted tube, sinusoidal pattern, helical fused sinusoidal elements, corrugated ring, Wiktor tantalum stent, etc. Commercially available stents include, Cordis Palmaz-Schatz, Cordis Crown, Bx-Veclocity, S670, S7, ACS Multi-Link, Multi-Link Tetra, Multi-Link Penta, NIR, and Express. They can be made of any suitable material(s), including, e.g., stainless steel, gold, platinum iridium, polymers, niobium alloy, cobalt alloys, nickel-titanium, cobalt-chromium, etc.

Active agents can be coated directly on to an implantable medical device, or impregnated or otherwise associated with a material or carrier (e.g., a polymeric substance) which is then placed in contact with it. Once the stent or graft is implanted within a cardiovascular system lumen, the active agent is released, thereby resulting in its delivery to the local tissues. These can also be referred to as coated, medicated, or drug-eluting implantable devices. Metallic designs can be coated with thin (e.g., 5-10 micrometers) elastomeric biostable polymer surface membrane coatings which comprise the active compound. The stent backbone can also comprise drilled holes or wells that comprise the drug (e.g., in a polymeric time-release substrate). Alternatively, it can be present in a film that is cast on the stent backbone.

Any method of associating a compound of the present invention with an implantable device can be used. Compounds can be embedded, implanted, coated, impregnated, layered, covered, etc. directly on to the device, or otherwise associated with a carrier material. There are many examples of implantable devices, drug-eluting devices, materials to achieve drug delivery, etc., and the present invention is not limited by which are utilized. See, e.g., Waksman, Cardiovasc Radiat Med. 2002 July-December; 3(3-4):226-41; Eberhart et al., J Biomater Sci Polym Ed. 2003; 14(4):299-312; Wieneke et al., Expert Opin Investig Drugs. 2003 May;12(5): 771-9; Tsuji et al., Int J Cardiovasc Intervent. 2003; 5(1):13-6; U.S. Pat. Nos. 6,712,845; 6,709,514; 6,702,850; 6,673,385; 6,673,154; 6,620,194; 6,613,084; 6,589,546; 6,585,765; 6,574,851; 6,569,195; 6,555,157; 6,545,097; 6,530,951; 6,475,235; 6,395,326; 6,375,677; 6,364,893; 6,358,556; 6,335,029; 6,316,018; 6,273,908; 6,258,121; 6,245,102; 6,179,789; 6,080,190; 5,879,697; 5,876,433; 5,527,324; 5,469,868; 5,464,650; 5,700,286; 5,605,696. The compound can be combined with materials which controllably-release it into the system, e.g., to achieve steady-state concentrations of the compound.

The devices can further comprise any pharmacological or active agent which is useful for treating and/or preventing restenosis, including, but not limited to, antibiotic, antineoplastic, anti-inflammatory, antiplatelet, anticoagulant, fibrinolytic, thrombin inhibitor, antimitotic, and antiproliferative agents.

The present invention provides an intravascular stent for introduction into a vascular lumen, comprising, e.g., an elongated body having surfaces, wherein said surfaces comprise an effective amount of a compound of the present invention to prevent and/or treat and/or delay restenosis. The stent can have inner and outer surfaces, where one surface or both are coated with compounds. The stent can have any structure as mentioned above, e.g., a scaffold or backbone that is expandable, self-expanding, tube, wire, sheet, ribbon, coil, helical spiral, woven, etc. The surfaces of the stent can be coated directly with the compound, or associated with a carrier or substrate that comprises the compound, e.g., where the substrate or carrier is impregnated with a compound of formula I. The stent can have any suitable geometry, e.g., an elongated body which is substantially cylindrical.

General Preparative Methods

The diaryl ureas of Formula I may be prepared by the use of known chemical reactions and procedures, some from starting materials that are commercially available. Nevertheless, general preparative methods are provided below to aid one skilled in the art in synthesizing these compounds.

The following general preparative methods are presented to aid the reader in synthesizing the compounds of the present invention. All variable groups of these methods are as described in the generic description if they are not specifically defined below. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

General Method

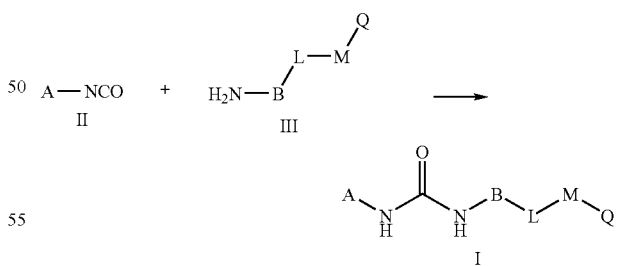

The urea compounds (I) can be synthesized as above by reacting amino compounds (III) with isocyanate compounds (II).

The compounds (II) are commercially available or can be synthesized according to methods commonly known to those skilled in the art [e.g. from treatment of an amine with phosgene or a phosgene equivalent such as trichloromethyl chloroformate (diphosgene), bis(trichloromethyl)carbonate (triphosgene), or N,N'-carbonyldiimidazole (CDI); or, alternatively by a Curtius-type rearrangement of an amide, or a carboxylic acid derivative, such as an ester, an acid halide or an anhydride]. The compounds (III) can be synthesized according methods commonly known to those skilled in the art.

In addition, specific preparations of diaryl ureas of Formula (I) are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy)phenyl]ureas as raf kinase inhibitors" PCT Int. Appl., WO O2 62763, Dumas, J. et al. "Inhibition of raf kinase using quinolyl, isoquinolyl or pyridyl ureas" PCT Int. Appl., WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394, Carter, C. A. et al. "Aryl urea compounds in combination with other cytostatic or cytotoxic agents for treating human cancers and other raf kinase-mediated diseases" PCT Int. Appl., WO 03 47579, Riedl, B. et al. "Omega-carboxyaryl substituted diphenyl ureas as raf kinase inhibitors" U.S. Pat. Appl. Publ. US 20030144278, Dumas, J. et al. "Aryl ureas with raf kinase and angiogenesis inhibiting activity" PCT Int. Appl., WO 03 68223, Dumas, J. et al. "Aryl ureas with angiogenesis inhibiting activity" PCT Int. Appl., WO 03 68228, Dumas, J. et al. "Pyridine, quinoline, and isoquinoline N-oxides as kinase inhibitors" PCT Int. Appl., WO 03 68229, Dumas, J. et al. "Aryl ureas as kinase inhibitors" PCT Int. Appl., WO 03 68746; U.S. Provisional Application Nos. 60/540,326, 60/489,102, and 536,734.

The reaction of the compounds (II) with (III) is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The compounds (III) are generally employed in an amount of from 1 to 3 mol per mol of compounds (II); an equimolar amount or slight excess of compounds (III) is preferred.

The reaction of the compounds (II) with (III) is generally carried out within a relatively wide temperature range. In general, they are carried out in a range of from −20 to 200° C., preferably from 0 to 100° C., and more preferably from 25 to 50° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

Synthetic transformations that may be employed in the synthesis of compounds of Formula I and in the synthesis of intermediates involved in the synthesis of compounds of Formula I are known by or accessible to one skilled in the art. Collections of synthetic transformations may be found in compilations, such as:

J. March. *Advanced Organic Chemistry*, 4th ed.; John Wiley: New York (1992)

R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

Compounds of the invention may also be administrated transdermally using methods ("patches") known to those skilled in the art (see, for example: Chien; "Transdermal Controlled Systemic Medications"; Marcel Dekker, Inc.; 1987. Lipp et al. WO94/04157). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents. For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Controlled release formulations for parenteral administration include liposomal, polymeric microsphere and polymeric gel formulations, which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA J. Pharmaceut. Sci. Tech.* 1998, 52(5), 238-311; Strickley, R. G "Parenteral Formulations of Small Molecule Therapeutics Marketed in the United States (1999)-Part-1" *PDA J. Phar-*

*maceut. Sci. Tech.* 1999, 53(6), 324-349; and Nema, S. et al, "Excipients and Their Use in Injectable Products" *PDA J. Pharmaceut. Sci. Tech.* 1997, 51(4), 166-171.

This invention also relates to administering pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound, or salt thereof, of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, otically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent.

Various other materials may be present as coatings or to otherwise modify the physical form of the dosage unit. For instance tablets, pills or capsules may be coated with shellac, sugar or both.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to camauba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

The total amount of the active ingredient to be administered will generally range from about 0.001 mg/kg to about 200 mg/kg, and preferably from about 0.01 mg/kg to about 20 mg/kg body weight per day. A unit dosage may contain from about 0.5 mg to about 1500 mg of active ingredient, and can be administered one or more times per day. For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regime will preferably be from 0.01 to 200 mg/Kg of total body weight. The daily vaginal dosage regime will preferably be from 0.01 to 200 mg/Kg of total body weight. The daily topical dosage regime will preferably be from 0.1 to 200 mg administered between one to four times daily. The transdermal concentration will preferably be that required to maintain a daily dose of from 0.01 to 200 mg/Kg. The daily inhalation dosage regime will preferably be from 0.01 to 100 mg/Kg of total body weight. These dosages regimes can be achieved with multiple dosages within a single day or extended dosages, such as those given on a weekly or monthly basis.

Based upon standard laboratory techniques known to evaluate compounds, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and gender of the patient treated, and the nature and extent of the condition treated.

It will be appreciated by those skilled in the art that the particular method of administration will depend on a variety of factors, all of which are considered routinely when administering therapeutics. It will also be appreciated by one skilled in the art that the specific dose level for a given patient depends on a variety of factors, including specific activity of the compound administered, age, body weight, health, sex, diet, time and route of administration, rate of excretion, etc. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

It will be further appreciated by one skilled in the art that the optimal course of treatment, i.e., the mode of treatment and the daily number of doses of a compound of this invention given for a defined number of days, can be ascertained by those skilled in the art using conventional treatment tests.

Dosages and compound efficacy can also be determined routinely using in vitro and in vivo animal models. For example, murine models have been developed using mice deficent in apolipoprotein E (Leidenfrost et al., Am. J. Pathol., 163:773-778, 2003). See, also Bayes-Genis et al, Curr. Intv. Cardio. Rep., 2:303-308, 200, for reviews of rat, rabbit, canine, baboon, and procine models.

Pharmaceutical compositions according to the present invention can be illustrated as follows:

Sterile IV Solution:

A 5 mg/ml solution of the desired compound of this invention is made using sterile, injectable water, and the pH is adjusted if necessary. The solution is diluted for administration to 1-2 mg/ml with sterile 5% dextrose and is administered as an IV infusion over 60 minutes.

Lyophilized Powder for IV Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular Suspension:

The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety, U.S. Provisional Application No. 60/556,062, filed Mar. 25, 2004, 60/520,399, filed Nov. 17, 2003, and 60/471,735, filed May 20, 2003, each of which are hereby incorporated by reference in their entirety.

EXAMPLES

Murine PDGFR FRET Biochemical Assay

This assay was formatted in a 96-well black plate (Costar 3915). The following reagents (and their sources) are used: Europium-labeled anti-phosphotyrosine antibody pY20 and streptavidin-APC; poly GT-biotin, and mouse PDGFR within DRT. The reaction conditions are as follows: 1 nM mouse PDGFR is combined with 20 µM ATP, 7 nM poly GT-biotin, 1 nM pY20 antibody, 5 nM streptavidin-APC, and 1% DMSO in assay buffer (50 mM HEPES pH 7.5, 10 mM $MgCl_2$, 0.1 mM EDTA, 0.015% BRIJ 35, 0.1 mg/mL BSA, 0.1% mercaptoethanol). Reaction is initiated upon addition of enzyme. Final reaction volume in each well is 100 µL. After 90 minutes, the reaction is stopped by addition of 10 µL/well of 5 µM staurosporine. Plates are read at both 615 and 665 nm on a Perkin Elmer VictorV Multilabel counter at about 1 hour after the reaction is stopped. Signal is calculated as a ratio: (665 nm/615 nm)*10000 for each well.

For $IC_{50}$ generation for PDGFR beta, compounds were added prior to the enzyme initiation. A 50-fold stock plate was made with compounds serially diluted 1:3 in a 50% DMSO/50% $dH_2O$ solution. A 2 µL addition of the stock to the assay gave final compound concentrations ranging from 110 µM-4.56 nM in 1% DMSO. The data were expressed as percent inhibition: % inhibition=100−((Signal with inhibitor−background)/(Signal without inhibitor−background))*100

The following compounds show an $IC_{50}$ of less than 10 micromolar in this biochemical assay, which represents a marked inhibition of PDGFR:

N-(4-chloro-3-(trifluoromethyl)phenyl)-N'-(4-(2-(N-methylcarbamoyl)-4-pyridyl oxy)phenyl) urea, N-(4-bromo-3-(trifluoromethyl)phenyl)-N'-(4-(2-(N-methylcarbamoyl)-4-pyridyl oxy)phenyl) urea, N-(4-bromo-3-(trifluoromethyl)phenyl)-N'-(4-(2-(N-methylcarbamoyl)-4-pyridyl oxy)-2-chlorophenyl) urea, N-(4-chloro-3-(trifluoromethyl)phenyl)-N'-(4-(2-carbamoyl-4-pyridyloxy)phenyl) urea, N-(4-chloro-3-(trifluoromethyl)phenyl)-N'-(4-(1-hydroxy-2-carbamoyl-4-pyridyl oxy)phenyl) urea, N-(4-chloro-3-(trifluoromethyl)phenyl)-N'-(4-(1-hydroxy-2-(N-methylcarbamoyl)-4-pyridyl oxy)phenyl) urea, N-(4-chloro-3-(trifluoromethyl)phenyl)-N'-(4-(2-(N-methylcarbamoyl)-4-pyridyl oxy)-2-fluorophenyl) urea, N-(4-bromo-3-(trifluoromethyl)phenyl)-N'-(4-(2-(N-methylcarbamoyl)-4-pyridyl oxy)-2-fluorophenyl) urea, N-(4-fluoro-3-(trifluoromethyl)phenyl)-N'-(4-(2-(N-methylcarbamoyl)-4-pyridyl oxy)-2-fluorophenyl) urea, N-(4-chloro-3-(trifluoromethyl)phenyl)-N'-(4-(2-(N-methylcarbamoyl)-4-pyridyl oxy)-2-chlorophenyl) urea, N-(6-(2,2,4,4-tetrafluoro-4H-benzo[1,3]dioxinyl))-N'-(4-(2-cyano-4-pyridyloxy) phenyl) urea, and N-(6-(2,2,4,4-tetrafluoro-4H-benzo[1,3]dioxinyl))-N'-(4-(2-cyano-4-pyridyloxy)-2-fluorophenyl) urea.

pPDGFR-Beta Sandwich ELISA in AoSMC Cells

100K P3-P6 Aortic SMC were plated in each well of 12-well cluster in 1000 uL volume/well of SGM-2 using standard cell culture techniques. Next day, cells were rinsed with 1000 uL D-PBS (Gibco) once, then serum starved in 500 uL SBM (smooth muscle cell basal media) with 0.1% BSA (Sigma, Cat A9576) overnight. Compounds were diluted at a dose range from (10 uM to 1 nM in 10-fold dilution steps in DMSO. Final DMSO concentration 0.1%). Remove old media by inversion into the sink quickly then add 100 ul of each dilution to corresponding well of cells for 1 hr at 37° C. Cells were then stimulated with 10 ng/mL PDGF BB ligand for 7 minutes at 37° C. The media is decanted and 150 uL of isotonic lysis buffer with protease inhibitor tablet (Complete; EDTA-free) and 0.2 mM Na vanadate is added. Cells are lysed for 15 min at 4° C. on shaker in cold room. Lysates are put in eppendorf tubes to which 15 uL of agarose-conjugated anti-PDGFR-b antibody is added (Santa Cruz, sc-339) and incubated at 4° C. overnight. Next day, beads are rinsed in 50-volumes of PBS three times and boiled in 1×LDS sample buffer (Invitrogen) for 5 minutes. Samples were run on 3-8% gradient Tris-Acetate gels (Invitrogen) and transferred onto Nitrocellulose. Membranes were blocked in 1% BSA/TBS-T for 1 hr. before incubation in anti-phospho-PDGFR-b (Tyr-857) antibody in blocking buffer (1:1000 dilution) for 1 hour. After three washes in TBS-T, membranes were incubated in Goat anti-rabbit HRP IgG (Amersham, 1:25000 dilution) for 1 hr. Three more washes followed before addition of ECL substrate. Membranes were exposed to Hyperfilm-ECL. Subsequently, membranes were stripped and reprobed with anti-PDGFR-beta antibody (Santa Cruz, SC-339) for total PDGFR-beta.

The following compounds show an $IC_{50}$ of less than 10 micromolar in this bioassay of PDGFR inhibition in cells:

N-(4-chloro-3-(trifluoromethyl)phenyl)-N'-(4-(2-(N-methylcarbamoyl)-4-pyridyl oxy)phenyl) urea, N-(4-chloro-3-(trifluoromethyl)phenyl)-N'-(4-(2-(N-methylcarbamoyl)-4-pyridyl oxy)-2-fluorophenyl) urea, and N-(4-chloro-3-(trifluoromethyl)phenyl)-N'-(4-(2-(N-methylcarbamoyl)-4-pyridyl oxy)-2-chlorophenyl) urea.

What is claimed:

1. A method for treating a disease or condition in mammal, or a mammalian cell thereof, which is a tumor, chronic myeloid leukemia, inflammation, renal disease, diabetic nephropathy, mesangial proliferative glomerulonephritis, atherosclerosis, restenosis, hypertension-related arteriosclerosis, venous bypass graft arterosclerosis, scleroderma, interstitial pulmonary disease, a synovial disorder, arthritis, leukemia or lymphoma mediated by platelet-derived growth factor receptor-beta, where a defect in the receptor itself is involved in "causing" the disease; or functional activity of PDGFR results in the disease symptom and/or phenotype when inappropriately expressed, said method comprising:

administering to a subject in need thereof, an effective amount of an aryl urea compound of formula I, a salt form of a compound of Formula I, an isolated or mixed stereoisomer of a compound of Formula I,

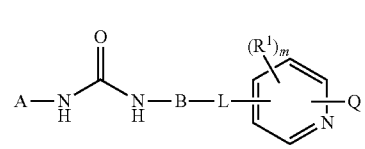

wherein:

A is phenyl, optionally substituted 1, 2 or 3 times by $R^3$, wherein each $R^3$ is independently $C_1$-$C_5$ alkyl, $C_1$-$C_5$ haloalkyl, up to per-haloalkyl, $C_1$-$C_5$ alkoxy, $C_1$-$C_5$ haloalkoxy, up to per-haloalkoxy, halogen, cyano, or nitro; or A is a group of the formula:

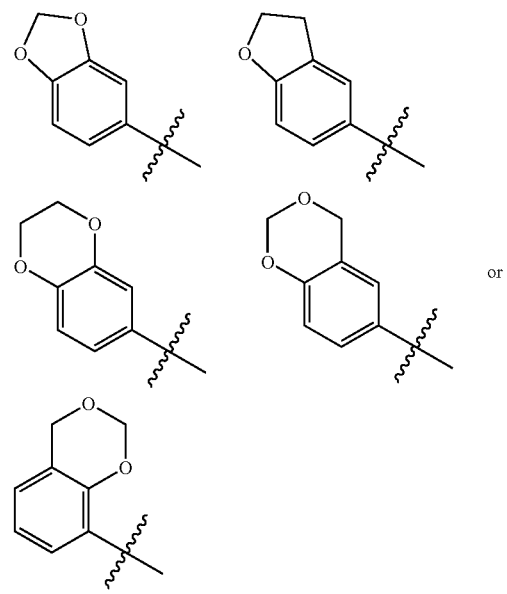

optionally substituted 1, 2, 3, 4, 5 or 6 times with $R^4$ wherein each $R^4$ is independently $C_1$-$C_5$ alkyl or halogen;

B is phenylene, optionally substituted 1, 2 or 3 times by $R^2$, or naphthylene, optionally substituted optionally substituted 1, 2 or 3 times by $R^2$, wherein each $R^2$ is independently $C_1$-$C_5$ alkyl, $C_1$-$C_5$ haloalkyl, up to per-haloalkyl, $C_1$-$C_5$ alkoxy, $C_1$-$C_5$ haloalkoxy up to per-haloalkoxyl, halogen, cyano or nitro;

Q is cyano, —C(O)—$R^a$, or —C(O)—$NR^bR^c$, where each $R^a$, $R^b$ and $R^c$ is independently H or $C_1$-$C_5$ alkyl, L is —O— or —S—, m is an integer 0, 1, 2 or 3, and each $R^1$ is independently halogen, $C_{1-5}$ alkyl, $C_{1-5}$ haloalkyl, up to per-haloalkyl, $C_{1-5}$ alkoxy, $C_{1-5}$ haloalkoxy, up to per-haloalkoxy, N-oxo or N-hydroxy.

2. A method of claim 1 wherein for the compound of formula (I), each $R^2$ is independently methyl, ethyl, propyl, butyl, isopropyl, tert-butyl, trifluoromethyl, methoxy, CN or $NO_2$.

3. A method of claim 1 wherein for the compound of formula (I), each $R^3$ is independently fluorine, chorine, bromine, methyl, ethyl, propyl, butyl, pentyl, isopropyl, isobutyl, sec-butyl, tert-butyl, trifluoromethyl, methoxy, ethoxy, trifluoromethoxy, CN or NO₂ and each R⁴ is independently fluorine, chorine, bromine or methyl.

4. A method of claim 1 wherein for the compound of formula (I), each R¹ is independently methyl, ethyl, propyl, oxygen, cyano, n-oxo or n-hydroxy and each Rᵃ, Rᵇ and Rᶜ is independently H or methyl.

5. A method of claim 1 wherein for the compound of formula (I),
- each Rᵃ, Rᵇ and Rᶜ is independently H or methyl;
- each R¹ is independently methyl, ethyl, propyl, oxygen, cyano, n-oxo or n-hydroxy;
- each R² is independently methyl, ethyl, propyl, butyl, isopropyl, tert-butyl, trifluoromethyl, methoxy, CN or NO₂;
- each R³ is independently fluorine, chorine, bromine, methyl, ethyl, propyl, butyl, pentyl, isopropyl, iso-butyl, sec-butyl, tert-butyl, trifluoromethyl, methoxy, ethoxy, trifluoromethoxy, CN or NO₂; and
- each R⁴ is independently fluorine, chorine, bromine or methyl.

6. A method of claim 1 wherein for the compound of formula (I), A is substituted phenyl.

7. A method of claim 1 wherein for the compound of formula (I), A is substituted phenyl;
- each Rᵃ, Rᵇ and Rᶜ is independently H or methyl;
- each R¹ is independently methyl, ethyl, propyl, oxygen, cyano, n-oxo or n-hydroxy;
- each R² is independently methyl, ethyl, propyl, butyl, isopropyl, tert-butyl, trifluoromethyl, methoxy, CN or NO₂; and
- each R³ is independently fluorine, chorine, bromine, methyl, ethyl, propyl, butyl, pentyl, isopropyl, iso-butyl, sec-butyl, tert-butyl, trifluoromethyl, methoxy, ethoxy, trifluoromethoxy, CN or NO₂.

8. A method of claim 1 wherein for the compound of formula (I), A is a group of the formula:

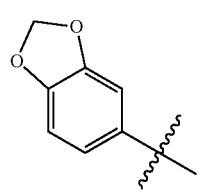 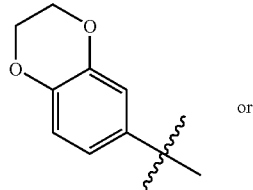 or

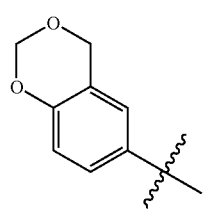

optionally substituted 1, 2, 3 or 4 times with R⁴, wherein each R⁴ is independently chlorine or fluorine.

9. A method of claim 1 wherein for the compound of formula (I), A is a group of the formula:

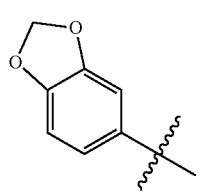 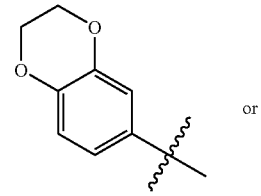 or

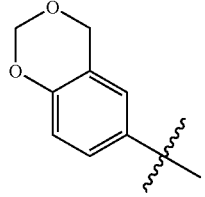

optionally substituted 1, 2, 3 or 4 times with R⁴, and wherein
- each Rᵃ, Rᵇ and Rᶜ is independently H or methyl;
- each R¹ is independently methyl, ethyl, propyl, oxygen, cyano, n-oxo or n-hydroxy;
- each R² is independently methyl, ethyl, propyl, butyl, isopropyl, tert-butyl, trifluoromethyl, methoxy, CN or NO₂; and
- each R⁴ is independently fluorine or chorine.

10. A method of claim 1 wherein for the compound of formula (I), B is phenylene.

11. A method of claim 5 wherein for the compound of formula (I), B is phenylene.

12. A method of claim 1 wherein for the compound of formula (I), B is naphthylene.

13. A method of claim 5 wherein for the compound of formula (I), B is naphthylene.

14. A method of claim 1 wherein for the compound of formula (I), A is substituted phenyl and B is phenylene.

15. A method of claim 1 wherein for the compound of formula (I), A is substituted phenyl; B is phenylene,
- each Rᵃ, Rᵇ and Rᶜ is independently H or methyl;
- each R¹ is independently methyl, ethyl, propyl, oxygen, cyano, n-oxo or n-hydroxy;
- each R² is independently methyl, ethyl, propyl, butyl, isopropyl, tert-butyl, trifluoromethyl, methoxy, CN or NO₂ and
- each R³ is independently fluorine, chorine, bromine, methyl, ethyl, propyl, butyl, pentyl, isopropyl, iso-butyl, sec-butyl, tert-butyl, trifluoromethyl, methoxy, ethoxy, trifluoromethoxy, CN or NO₂.

16. A method of claim 1 wherein for the compound of formula (I),
A is a group of the formula:

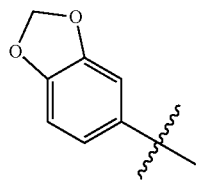 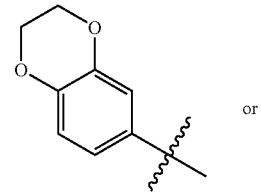 or

-continued

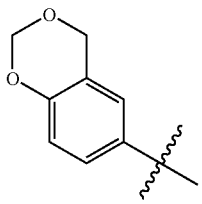

optionally substituted 1, 2, 3 or 4 times with R⁴, wherein each R⁴ is independently chlorine or fluorine and B is phenylene.

17. A method of claim 1 wherein for the compound of formula (I),

A is a group of the formula:

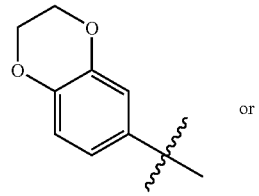

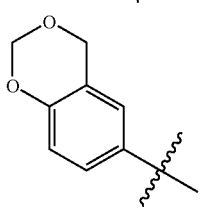

optionally substituted 1, 2, 3 or 4 times with R⁴;
B is phenylene;
each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or NO₂; and
each $R^4$ is independently fluorine or chlorine.

18. A method of claim 1 wherein for the compound of formula (I), L is oxygen.

19. A method of claim 5, wherein for the compound of formula (I), L is oxygen.

20. A method of claim 1, wherein for the compound of formula (I), A is substituted phenyl, and L is oxygen.

21. A method of claim 1, wherein for the compound of formula (I), B is phenylene and L is oxygen.

22. A method of claim 1, wherein for the compound of formula (I), B is naphthylene and L is oxygen.

23. A method of claim 1, wherein for the compound of formula (I), A is substituted phenyl; B is phenylene and L is oxygen.

24. A method of claim 23, wherein for the compound of formula (I), each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or NO₂; and
each $R^3$ is independently fluorine, chorine, bromine, methyl, ethyl, propyl, butyl, pentyl, isopropyl, iso-butyl, sec-butyl, tert-butyl, trifluoromethyl, methoxy, ethoxy, trifluoromethoxy, CN or NO₂.

25. A method of claim 1, wherein for the compound of formula (I), A is substituted phenyl; B is naphthylene and L is oxygen.

26. A method of claim 25, wherein for the compound of formula (I), each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or NO₂; and
each $R^3$ is independently fluorine, chorine, bromine, methyl, ethyl, propyl, butyl, pentyl, isopropyl, iso-butyl, sec-butyl, tert-butyl, trifluoromethyl, methoxy, ethoxy, trifluoromethoxy, CN or NO₂.

27. A method of claim 1, wherein for the compound of formula (I), A is a group of the formula:

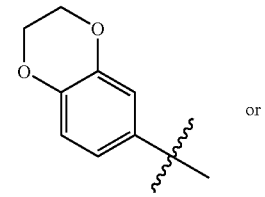

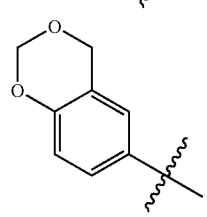

optionally substituted 1, 2, 3 or 4 times with R⁴, B is phenylene and L is oxygen, wherein each R⁴ is independently chlorine or fluorine.

28. A method of claim 27 wherein for the compound of formula (I),
each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or NO₂; and
each $R^4$ is independently fluorine or chorine.

29. A method of claim 1 wherein for the compound of formula (I), L is oxygen; B is naphthylene, A is a group of the formula:

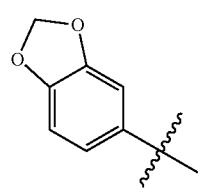 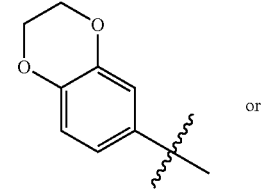 or

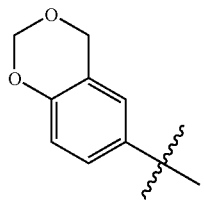

optionally substituted 1, 2, 3 or 4 times with $R^4$;
each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or $NO_2$; and
each $R^4$ is independently fluorine or chorine.

30. A method of claim 29 wherein for the compound of formula (I),
each $R^a$, $R^b$ and $R^c$ is independently H or methyl;
each $R^1$ is independently methyl, ethyl, propyl, oxygen, cyano, n-oxo or n-hydroxy;
each $R^2$ is independently methyl, ethyl, propyl, butyl, isopropyl, tert-butyl, trifluoromethyl, methoxy, CN or $NO_2$; and
each $R^4$ is independently fluorine or chorine.

31. A method of claim 15 wherein for the compound of formula (I), each $R^3$ is chlorine, bromine, tert-butyl, trifluoromethyl or methoxy.

32. A method of claim 24 wherein for the compound of formula (I), each $R^3$ is chlorine, bromine, tert-butyl, trifluoromethyl or methoxy.

33. A method of claim 26 wherein for the compound of formula (I), each $R^3$ is chlorine, bromine, tert-butyl, trifluoromethyl or methoxy.

34. A method for treating a disease or condition in mammal, or a mammalian cell thereof, which is a tumor, chronic myeloid leukemia, inflammation, renal disease, diabetic nephropathy, mesangial proliferative glomerulonephritis, atherosclerosis, restenosis, hypertension-related arterosclerosis, venous bypass graft arterosclerosis, scleroderma, interstitial pulmonary disease, a synovial disorder, arthritis, leukemia or lymphoma mediated by platelet-derived growth factor receptor-beta where a defect in the receptor itself is involved in "causing" the disease or functional activity of PDGFR results in the disease symptom and/or phenotype when inappropriately expressed, said method comprising:
administering to a subject in need thereof, an effective amount of
an aryl urea compound of formulae X, Y, ZA, ZB, or ZD,
a salt form of a compound of formulae X, Y, ZA, ZB, or ZD, or
an isolated or mixed stereoisomer of a compound of formulae X, Y, ZA, ZB, or ZD,

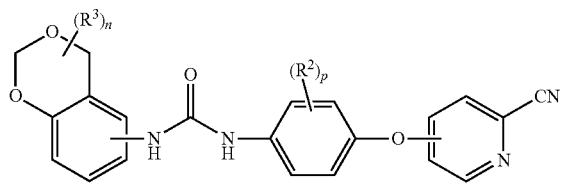

X

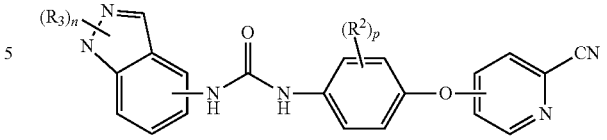

Y

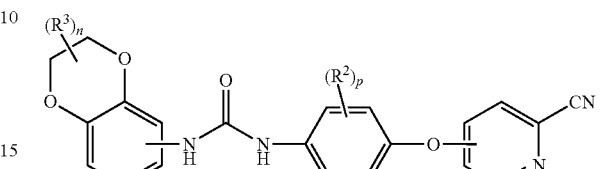

ZA

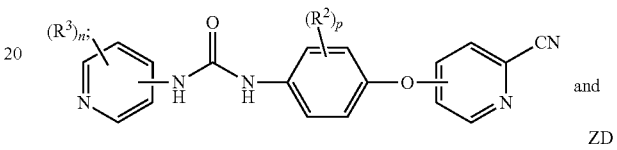

ZB

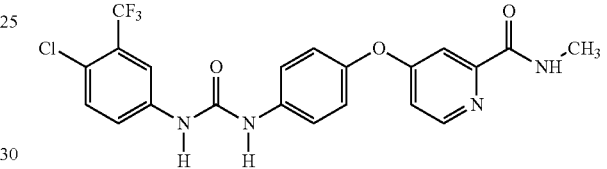

ZD wherein
each $R^3$ is independently halogen or trifluoromethyl and
each $R^2$ is independently
methyl, trifluoromethyl, methoxy, CN or $NO_2$
the variable n is 0, 1, 2, 3 or 4 and
the variable p is 0, 1 or 2.

35. A method of claim 1 wherein a pharmaceutically acceptable basic salt of an organic acid of formula (I) is administered.

36. A method of claim 34 wherein a pharmaceutically acceptable basic salt of an organic acid of formula (I) is administered.

37. A method of claim 1 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

38. A method of claim 34 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

39. A method of claim 15 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

40. A method of claim 24 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

41. A method of claim 26 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

42. A method of claim 28 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

43. A method of claim 34 wherein a pharmaceutically acceptable basic salt of an organic acid of formula (I) is administered, selected from hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

44. A method of claim 1 wherein the compound of formula I, is a hydrochloride, benzenesulfonate, or methanesulfonate salt of N-(4-chloro-3-(trifluoromethyl)phenyl)-N'-(4-(2-(N-methylcarbamoyl)-4-pyridyloxy)phenyl)urea.

45. The method of claim 1 wherein the compound of formula (I), is a tosylate salt of N-(4-chloro-3-(trifluoromethyl)phenyl-N'-(4-(2-(N-methylcarbamoyl)-4-pyridyloxy)phenyl)urea.

46. A method of claim 1 wherein for the compound of formula (I),
A is 4-chloro-3-trifluoromethylphenyl, 4-fluoro-3-trifluoromethylphenyl, 4-bromo-3-trifluoromethylphenyl, or 2,2,4,4-tetrafluoro-4H-benzo[1,3]dioxin-6-yl;
B is phenylene;
L is —O—;
and
Q is cyano, C(O)—NH$_2$, or C(O)—NHMe.

47. A method of claim 1 wherein the compound of formula (I), is:
N-(4-chloro-3-(trifluoromethyl)phenyl)-N'-(4-(2-(N-methylcarbamoyl)-4-pyridyloxy)phenyl)urea,
N-(4-bromo-3-(trifluoromethyl)phenyl)-N'-(4-(2-(N-methylcarbamoyl)-4-pyridyloxy)phenyl)urea,
N-(4-chloro-3-(trifluoromethyl)phenyl)-N'-(4-(2-carbamoyl-4-pyridyloxy)phenyl)urea,
N-(4-chloro-3-(trifluoromethyl)phenyl)-N'-(4-(1-hydroxy-2-carbamoyl-4-pyridyloxy) phenyl)urea,
N-(4-chloro-3-(trifluoromethyl)phenyl)-N'-(4-(1-hydroxy-2-(N-methylcarbamoyl)-4-pyridyloxy)phenyl) urea, or
N-(6-(2,2,4,4-tetrafluoro-4H-bezo[1,3]dioxinyl))-N'-(4-(2-cyano-4-pyridyloxy)phenyl)urea.

48. A method of claim 1 comprising administering an additional pharmaceutical agent with the compound of formula (I) to a patient in need thereof.

49. A method of claim 1 wherein said compound of formula (I) is administered to a patient in need thereof at an oral, intramuscular, intravenous, subcutaneous, or parenteral dosage which can range from about 0.1 to about 300 mg/kg of total body weight.

50. A method of claim 1, wherein said disease or condition is chronic myeloid leukemia, renal disease, diabetic nephropathy, mesangial proliferative glomerulonephritis, atherosclerosis, hypertension-related arterosclerosis, venous bypass graft arterosclerosis, scleroderma, interstitial pulmonary disease, a synovial disorder, arthritis, leukemia, lymphoma or restenosis following angioplasty.

51. A method of claim 1, wherein said disease or condition is graft rejection following transplantation of a donor tissue into a host.

52. A method of claim 5, wherein said disease or condition is chronic myeloid leukemia, renal disease, diabetic nephropathy, mesangial proliferative glomerulonephritis, atherosclerosis, hypertension-related arterosclerosis, venous bypass graft arterosclerosis, scleroderma, interstitial pulmonary disease, a synovial disorder, arthritis, leukemia, lymphoma or restenosis following angioplasty.

53. A method of claim 5, wherein said disease or condition is graft rejection following transplantation of a donor tissue into a host.

54. A method of claim 34, wherein said disease or condition is a tumor, chronic myeloid leukemia, renal disease, diabetic nephropathy, mesangial proliferative glomerulonephritis, atherosclerosis, hypertension-related arterosclerosis, venous bypass graft arterosclerosis, scleroderma, interstitial pulmonary disease, a synovial disorder, arthritis, leukemia, lymphoma or restenosis following angioplasty.

55. A method of claim 34, wherein said disease or condition is graft rejection following transplantation of a donor tissue into a host.

* * * * *

UNITED STATES PATENT AND TRADEMARK OFFICE
CERTIFICATE OF CORRECTION

| | | |
|---|---|---|
| PATENT NO. | : 8,796,250 B2 | Page 1 of 1 |
| APPLICATION NO. | : 10/848567 | |
| DATED | : August 5, 2014 | |
| INVENTOR(S) | : Wilhelm et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2267 days.

Signed and Sealed this
Twenty-fifth Day of August, 2015

Michelle K. Lee
*Director of the United States Patent and Trademark Office*